(12) United States Patent
Low et al.

(10) Patent No.: US 11,883,498 B2
(45) Date of Patent: Jan. 30, 2024

(54) LUTEINIZING HORMONE-RELEASING HORMONE RECEPTOR (LHRH-R) CONJUGATES AND USES THEREOF

(71) Applicant: PURDUE RESEARCH FOUNDATION, West Lafayette, IN (US)

(72) Inventors: Philip Stewart Low, West Lafayette, IN (US); Jyoti Roy, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 94 days.

(21) Appl. No.: 17/065,737

(22) Filed: Oct. 8, 2020

(65) Prior Publication Data

US 2021/0290767 A1   Sep. 23, 2021

Related U.S. Application Data

(63) Continuation of application No. 16/469,906, filed as application No. PCT/US2017/065996 on Dec. 13, 2017, now Pat. No. 10,821,188.

(60) Provisional application No. 62/434,383, filed on Dec. 14, 2016, provisional application No. 62/467,297, filed on Mar. 6, 2017.

(51) Int. Cl.
| | |
|---|---|
| *A61K 47/65* | (2017.01) |
| *A61K 45/06* | (2006.01) |
| *A61P 35/00* | (2006.01) |
| *A61K 38/09* | (2006.01) |
| *A61K 47/54* | (2017.01) |
| *A61K 49/00* | (2006.01) |

(52) U.S. Cl.
CPC ............ *A61K 47/545* (2017.08); *A61K 38/09* (2013.01); *A61K 45/06* (2013.01); *A61K 47/65* (2017.08); *A61K 49/0021* (2013.01); *A61P 35/00* (2018.01)

(58) Field of Classification Search
CPC ...... A61K 47/545; A61K 47/65; A61K 38/09; A61K 45/06; A61K 49/0021; A61P 35/00
See application file for complete search history.

(56) References Cited

U.S. PATENT DOCUMENTS

| | | | |
|---|---|---|---|
| 6,211,153 B1 | 4/2001 | Garnick | |
| 8,273,716 B2 | 9/2012 | Engel | |
| 10,821,188 B2* | 11/2020 | Low | A61K 9/0019 |
| 2006/0122202 A1 | 6/2006 | Guo | |
| 2006/0247177 A1 | 11/2006 | Millar | |
| 2009/0221569 A1 | 9/2009 | Engel | |

OTHER PUBLICATIONS

PCT International Search Report for PCT/US2017/065996, dated Feb. 13, 2018.
Extended European Search Report for 17880496.9, completed Apr. 20, 2020.
Deng, X., et al. "Synthesis and in vitro anti-cancer evaluation of luteinizing hormone-releasing hormone-conjugated peptide." Amino Acids, 47, 2015, pp. 2359-2366.
Struthers, S.R., et al. "Pharmacological Characterization of a Novel Nonpeptide Antagonist of the Human Gonadotropin-Releasing Hormone Receptor, NBI-42902." Endocrinology, 148, 2, 2007, pp. 857-867.
Olberg, D.E., et al. "Synthesis and in vitro evaluation of small-molecule [18F] labeled gonadotropin-releasing hormone (GnRH) receptor antagonists as potential PET imaging agents for GnRH receptor expression." Bioorganic & Medicinal Chemistry Letters, 24, 7, 2014, pp. 1846-1850.

* cited by examiner

*Primary Examiner* — Erich A Leeser
(74) *Attorney, Agent, or Firm* — Barnes & Thornburg LLP

(57) ABSTRACT

The present teachings relate generally to conjugates and methods for imaging a tumor microenvironment in a patient, and to conjugates and methods for treating LHRH-R expressing cancer in a patient. The present teachings relate generally to method of making conjugates comprising an LHRH-R antagonist.

19 Claims, 31 Drawing Sheets

JR-L3-S0456

JR-L2-Rhodamine

JR-L3

JR-L3-TubH

LUTEINIZING HORMONE-RELEASING HORMONE RECEPTOR (LHRH-R) CONJUGATES AND USES THEREOF

CROSS-REFERENCE TO RELATED APPLICATIONS

This application is a continuation of U.S. application Ser. No. 16/469,906 filed on Jun. 14, 2019, which is a U.S. national stage application under 35 U.S.C. § 371(b) of International Application No. PCT/US2017/065996 filed Dec. 13, 2017, which claims priority under 35 U.S.C. § 119(e) to U.S. Provisional Application Ser. No. 62/434,383, filed Dec. 14, 2016 and U.S. Provisional Application Ser. No. 62/467,297, filed Mar. 6, 2017, all of which are incorporated herein by reference in their entirety.

TECHNICAL FIELD

The present teachings relate generally to conjugates and methods for imaging a tumor microenvironment in a patient, and to conjugates and methods for treating LHRH-R expressing cancer in a patient. The present teachings relate generally to method of making conjugates comprising an LHRH-R antagonist.

BACKGROUND

Conventional cancer therapeutic drugs lack the ability to differentiate between cancer cells and healthy cells, which results in mild to severe adverse effects such as nausea, hair loss, myelosuppression, and cardiotoxicity. A strategy to overcome these side effects involves direct targeting of cancers through receptors or proteins which are overexpressed in cancers but have restricted expression in healthy cells. This allows delivery of cytotoxic drugs specifically to cancer cells while sparing the healthy cells.

Also, radioactive imaging techniques have gained popularity in identifying, staging and monitoring the disease progression. Targeting molecules including small-molecule, peptides, and antibodies have been radiolabeled to develop imaging agents for various receptors or proteins overexpressed in cancers. Fluorescence-guided surgery is an effective way to improve the surgical outcome and patient survival. Currently, there are multiple NIR dye conjugates targeted towards various receptors such as folate, PSMA, CAIX, CCK2R, and NK1R, etc. Despite the availability of these targeted NIR dye conjugates many cancers cannot be imaged either due to the presence or very low number of these receptors or complete absence. Thus, there is a need of more targeted dye conjugates.

Luteinizing hormone releasing hormone receptor (LHRH-R), which is also known as gonadotropin-releasing hormone receptor, has been accepted as a target to specifically deliver payloads such as cytotoxic drugs and imaging agents to the tumors expressing this receptor. LHRH-R belongs to the family of G-protein coupled receptor and has the binding site exposed to the extracellular space. LHRH-R is expressed in pituitary glands and regulates the production and release of the luteinizing hormone releasing hormone (LHRH) and follicle stimulating hormone (FSH). LHRH-R is also present in extra-hypothalamic tissues of ovary, endometrium, testis and prostate. There are also reports suggesting expression of the receptor in kidneys.

Expression of LHRH-R is not only reported on hormone-dependent cancers but also on hormone-independent cancers of the prostate, breast, ovary, endometrium, kidney, pancreas, brain, skin. LHRH-R receptors in cancer play a role in the growth and proliferation of cancers. Currently, both agonists and antagonists of LHRH-R are used to impair tumor growth. The expression of LHRH-R on healthy tissues is generally limited to pituitary and reproductive organs.

Currently, the natural peptide ligand, LHRH or its analogs are used to target LHRH-R. Even though LHRH-R targeted imaging agents have been developed, such studies have either used LHRH peptide or its analog or antibody to develop the LHRH-R targeted imaging agents. However, these peptide agents are limited by their propensity to non-specific uptake by liver and kidneys. The liver and kidney are important organs involved in recovering the peptides. For this reason, these organs express peptide scavenger receptors which result in non-specific uptake of the peptide-based cytotoxic drug conjugate and cause damage to these organs.

SUMMARY

The scope of the present invention is defined solely by the appended claims, and is not affected to any degree by the statements within this summary.

In one aspect, the present disclosure provides a conjugate of the formula B-L-A, wherein B is an LHRH-R binding antagonist of the formula

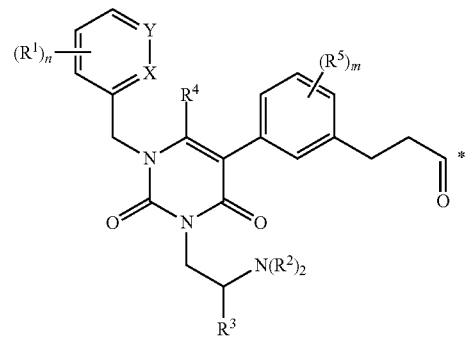

wherein each $R^1$ is independently halogen, $C_1$-$C_6$ alkyl or —$OC_1$-$C_6$ alkyl; each $R^2$ is independently H, $C_1$-$C_6$ alkyl or $C_3$-$C_6$ cycloalkyl; $R^3$ is $C_1$-$C_6$ alkyl, $C_3$-$C_6$ cycloalkyl, $C_6$-$C_{10}$ aryl or $C_1$-$C_6$ alkyl-($C_6$-$C_{10}$ aryl); $R^4$ is $C_1$-$C_6$ alkyl; each $R^5$ is independently selected from the group consisting of halogen, $C_1$-$C_6$ alkyl, —$OC_1$-$C_6$ alkyl, —$SC_1$-$C_6$ alkyl and —$OC_6$-$C_{10}$ aryl; X and Y are each independently N, CH or $CR^1$; provided that when X is N, Y is CH or $CR^1$, and when Y is N, X is CH or $CR^1$; m is an integer from 0 to 4; n is an integer from 0 to 3; and * represents a covalent bond to L; L is a linker; and A is a drug or an imaging agent; or a pharmaceutically acceptable salt thereof.

In another aspect, the present disclosure provides a pharmaceutical composition comprising a conjugate as described herein, or a pharmaceutically acceptable salt thereof, and optionally at least one pharmaceutically acceptable excipient.

In another aspect, the present disclosure provides a method of treating cancer in a subject, comprising, a. administering to the subject an effective amount of a conjugate as described herein; or a pharmaceutically acceptable salt thereof.

In another aspect, the present disclosure provides a conjugate as described herein, or a pharmaceutically acceptable salt thereof, for use in a method of treating LHRH-R expressing cancer in a subject.

In another aspect, the present disclosure provides use of a conjugate as described herein, or a pharmaceutically acceptable salt thereof, in the preparation of a medicament useful for treating LHRH-R expressing cancer in a subject.

In another aspect, the present disclosure provides a method of imaging a population of cells in vitro, comprising a. contacting the cells with a conjugate as described herein, to provide labelled cells, and b. visualizing the labelled cells.

In another aspect, the present disclosure provides a conjugate as described herein, for use in a method of imaging a population of cells in vitro.

In another aspect, the present disclosure provides a method of imaging a population of cells in vivo, comprising a. administering to a patient an effective amount of a conjugate as described herein, or a pharmaceutically acceptable salt thereof, to provide labelled cells; and b. visualizing the labelled cells by imaging.

In another aspect, the present disclosure provides a conjugate as described herein, for use in a method of imaging a population of cells in vitro.

Several embodiments of the invention are described in the following enumerated clauses:

1. A conjugate of the formula B-L-A, wherein B is an LHRH-R binding antagonist of the formula

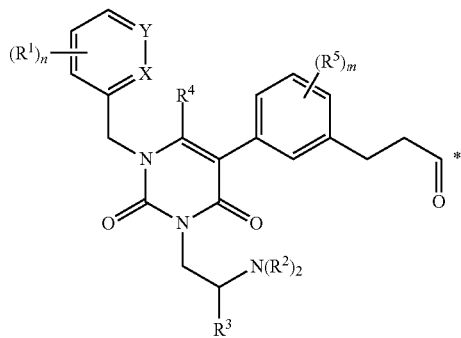

wherein
each $R^1$ is independently halogen, $C_1$-$C_6$ alkyl or —$OC_1$-$C_6$ alkyl,
each $R^2$ is independently H, $C_1$-$C_6$ alkyl or $C_3$-$C_6$ cycloalkyl;
$R^3$ is $C_1$-$C_6$ alkyl, $C_3$-$C_6$ cycloalkyl, $C_6$-$C_{10}$ aryl or $C_1$-$C_6$ alkyl-($C_6$-$C_{10}$ aryl);
$R^4$ is $C_1$-$C_6$ alkyl;
each $R^5$ is independently selected from the group consisting of halogen, $C_1$-$C_6$ alkyl, —$OC_1$-$C_6$ alkyl, —$SC_1$-$C_6$ alkyl and —$OC_6$-$C_{10}$ aryl;
X and Y are each independently N, CH or $CR^1$; provided that when X is N, Y is CH or $CR^1$, and when Y is N, X is CH or $CR^1$;

m is an integer from 0 to 4;
n is an integer from 0 to 3; and
represents a covalent bond to L;
L is a linker; and
A is a drug or an imaging agent;
or a pharmaceutically acceptable salt thereof.

2. The conjugate of clause 1 of the formula

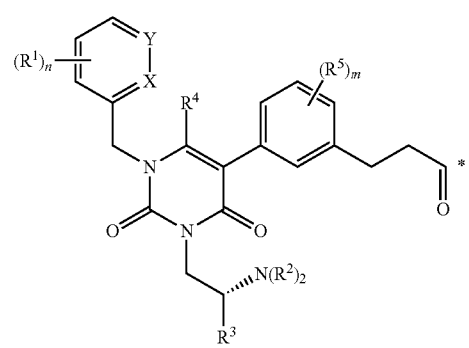

or a pharmaceutically acceptable salt thereof.

3. The conjugate of clause 1 or 2, or a pharmaceutically acceptable salt thereof, wherein n is 2.

4. The conjugate of clause 1, 2 or 3, or a pharmaceutically acceptable salt thereof, wherein m is 0.

5. The conjugate of any one of the preceding clauses, or a pharmaceutically acceptable salt thereof, wherein each $R^1$, if present, is F.

6. The conjugate of any one of the preceding clauses, or a pharmaceutically acceptable salt thereof, wherein each $R^1$, if present, is F in the 2- and 6-position of the ring to which each $R^1$ is attached.

7. The conjugate of any one of the preceding clauses, or a pharmaceutically acceptable salt thereof, wherein each $R^2$ is H.

8. The conjugate of any one of the preceding clauses, or a pharmaceutically acceptable salt thereof, wherein $R^3$ is $C_1$-$C_6$ alkyl-($C_6$-$C_{10}$ aryl).

9. The conjugate of any one of the preceding clauses, or a pharmaceutically acceptable salt thereof, wherein $R^3$—$CH_2$—$C_6H_5$.

10. The conjugate of any one of the preceding clauses, or a pharmaceutically acceptable salt thereof, wherein $R^4$ is methyl.

11. The conjugate of any one of the preceding clauses, or a pharmaceutically acceptable salt thereof, wherein each $R^5$, when present, is F, Cl, —$CH_3$, —$OCH_3$, —$OC_6H_5$ or —$SC_6H5$.

12. The conjugate of clause 1, or a pharmaceutically acceptable salt thereof, wherein X is N and Y is CH.

13. The conjugate of clause 1, or a pharmaceutically acceptable salt thereof, wherein Y is N and X is CH.

14. The conjugate of any one of the clauses 1 to 11, or a pharmaceutically acceptable salt thereof, wherein X is $CR^1$ and Y is CH or $CR^1$.

15. The conjugate of clause 14, wherein X is —CF and Y is CH.

16. The conjugate of clause 1, or a pharmaceutically acceptable salt thereof, wherein B is of the formula

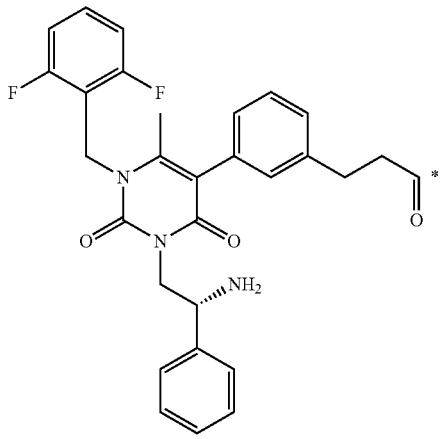 [SMILES: Cc1c(-c2cccc(CCC=O)c2)c(=O)n(C[C@H](N)c2ccccc2)c(=O)n1Cc1c(F)cccc1F]

wherein * represents a covalent bond to L.

17. The conjugate of any one of the preceding clauses, or a pharmaceutically acceptable salt thereof, wherein the linker comprises at least one amino acid.

18. The conjugate of any one of the preceding clauses, or a pharmaceutically acceptable salt thereof, wherein the linker comprises at least one amino acid selected from the group consisting of Lys, Asn, Thr, Ser, Ile, Met, Pro, His, Gln, Arg, Gly, Asp, Glu, Ala, Val, Phe, Leu, Tyr, Cys, and Trp.

19. The conjugate of any one of the preceding clauses, or a pharmaceutically acceptable salt thereof, wherein the linker comprises at least two amino acids independently selected from the group consisting of Glu and Cys.

20. The conjugate of any one of the preceding clauses, or a pharmaceutically acceptable salt thereof, wherein the linker comprises an amino acid portion of the formula Glu-Glu, wherein the glutamic acids are covalently bonded to each other through the carboxylic acid side chains.

21. The conjugate of any one of the preceding clauses, or a pharmaceutically acceptable salt thereof, wherein the linker comprises one or more hydrophilic spacer linkers comprising a plurality of hydroxyl functional groups.

22. The conjugate of any one of the preceding clauses, or a pharmaceutically acceptable salt thereof, wherein the linker comprises a moiety of the formula

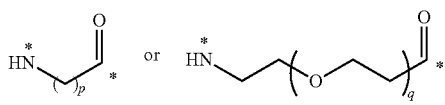

wherein p is an integer from 3 to 10, q is an integer from 3 to 100; and each * represents a covalent bond to the rest of the conjugate.

23. The conjugate of any one of the preceding clauses, or a pharmaceutically acceptable salt thereof, wherein the linker comprises a portion selected from the group consisting of

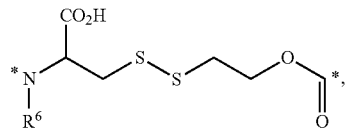

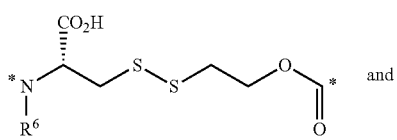

and

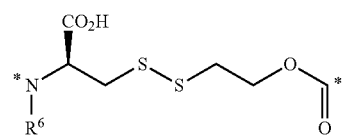

wherein $R^6$ is H or $C_1$-$C_6$ alkyl; and
each * represents a covalent bond to the rest of the conjugate.

24. The conjugate of clause 23, or a pharmaceutically acceptable salt thereof, wherein the linker is of the formula

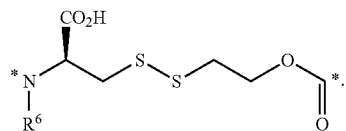

25. The conjugate of any one of the clauses 1 to 22, or a pharmaceutically acceptable salt thereof, wherein the linker comprises a portion selected from the group consisting of

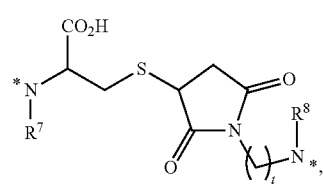

-continued

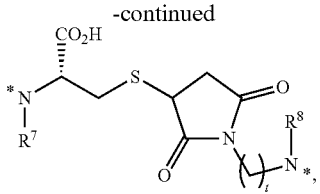

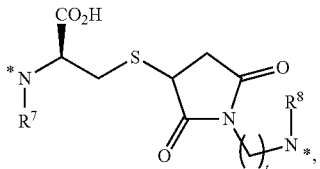

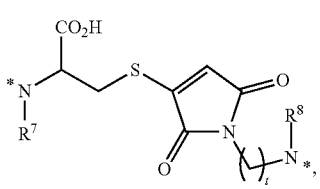

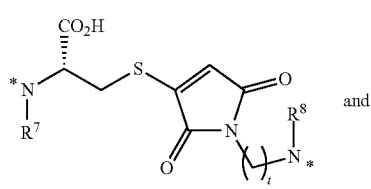

and

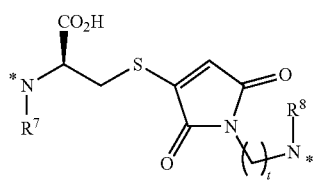

wherein
each of $R^7$ and $R^8$ is independently H or $C_1$-$C_6$ alkyl;
t is an integer from 1 to 8; and
each * represents a covalent bond to the rest of the conjugate.

26. The conjugate of clause 25, or a pharmaceutically acceptable salt thereof, wherein the linker is of the formula

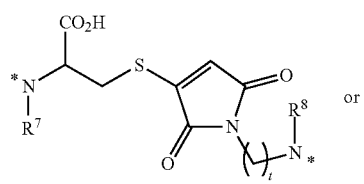

or

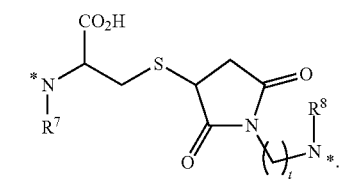

27. The conjugate of clause 25 or 26, or a pharmaceutically acceptable salt thereof, wherein $R^7$ and $R^8$ are H; and t is 2.

28. The conjugate of any one of the preceding clauses, or a pharmaceutically acceptable salt thereof, wherein the linker comprises a hydrazine.

29. The conjugate of clause 1, or a pharmaceutically acceptable salt thereof, comprising the formula

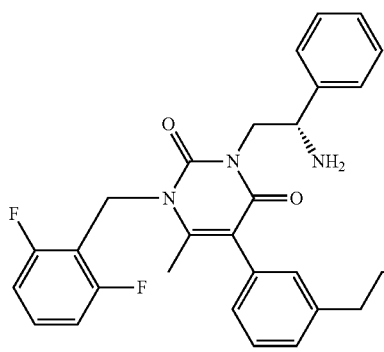
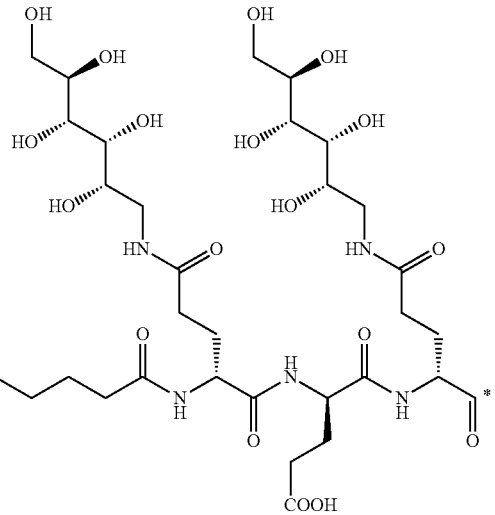

wherein * represents a covalent bond to the rest of the conjugate.
30. The conjugate of clause 1, or a pharmaceutically acceptable salt thereof, comprising the formula
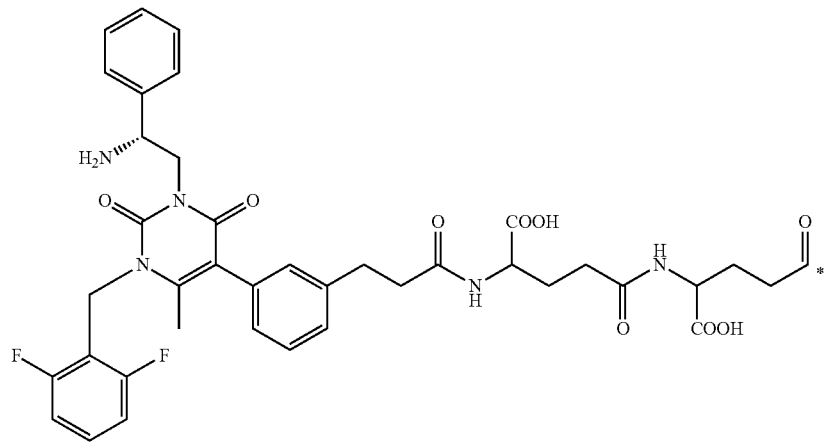 [SMILES: Cc1c(-c2cccc(CCC(=O)NC(CCC(=O)NC(CCC=O)C(=O)O)C(=O)O)c2)c(=O)n(C[C@H](N)c2ccccc2)c(=O)n1Cc1c(F)cccc1F]
wherein * represents a covalent bond to the rest of the conjugate.
31. The conjugate of clause 1, or a pharmaceutically acceptable salt thereof, comprising the formula
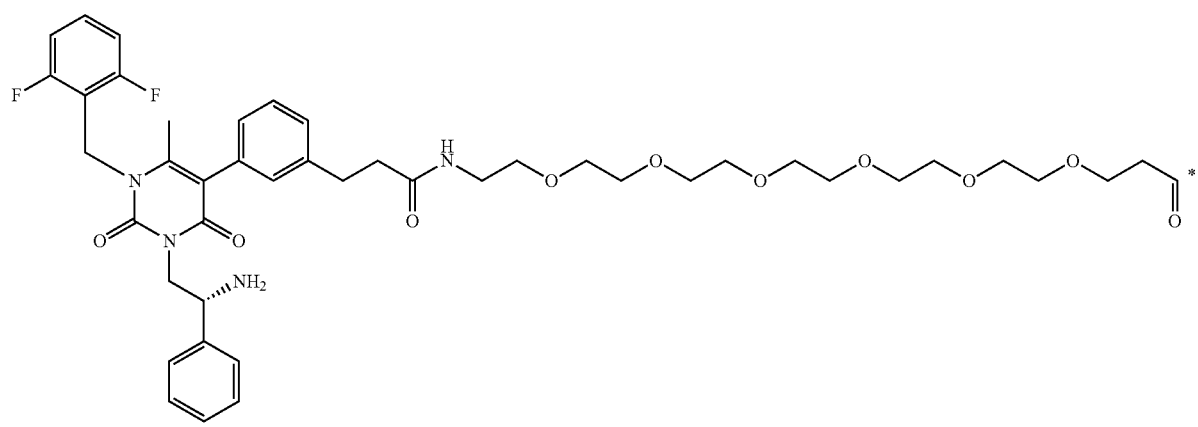 [SMILES: Cc1c(-c2cccc(CCC(=O)NCCOCCOCCOCCOCCOCCOCCC=O)c2)c(=O)n(C[C@H](N)c2ccccc2)c(=O)n1Cc1c(F)cccc1F]

wherein * represents a covalent bond to the rest of the conjugate.
32. The conjugate of clause 1, or a pharmaceutically acceptable salt thereof, comprising the formula
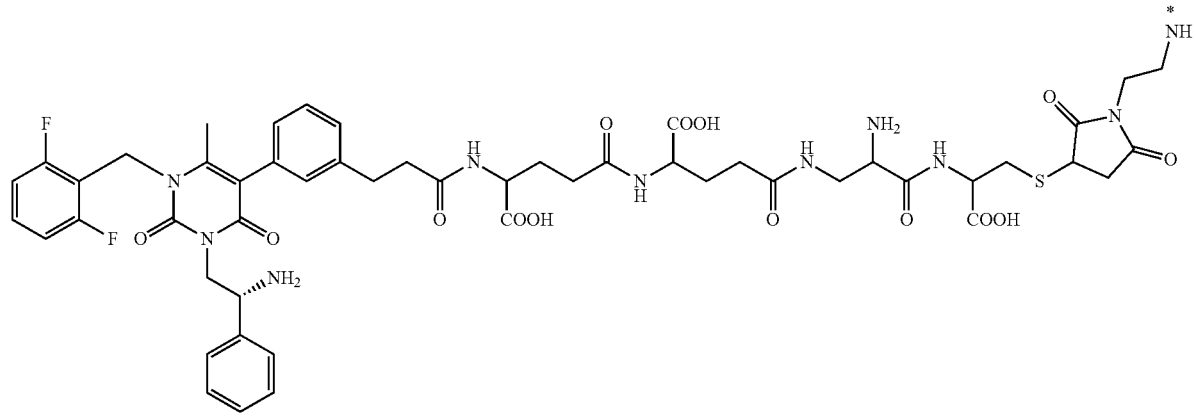 [SMILES: Cc1c(-c2cccc(CCC(=O)NC(CCC(=O)NC(CCC(=O)NCC(N)C(=O)NC(CSC3CC(=O)N(CCN)C3=O)C(=O)O)C(=O)O)C(=O)O)c2)c(=O)n(C[C@H](N)c2ccccc2)c(=O)n1Cc1c(F)cccc1F]
wherein * represents a covalent bond to the rest of the conjugate.
33. The conjugate of clause 1, or a pharmaceutically acceptable salt thereof, comprising the formula
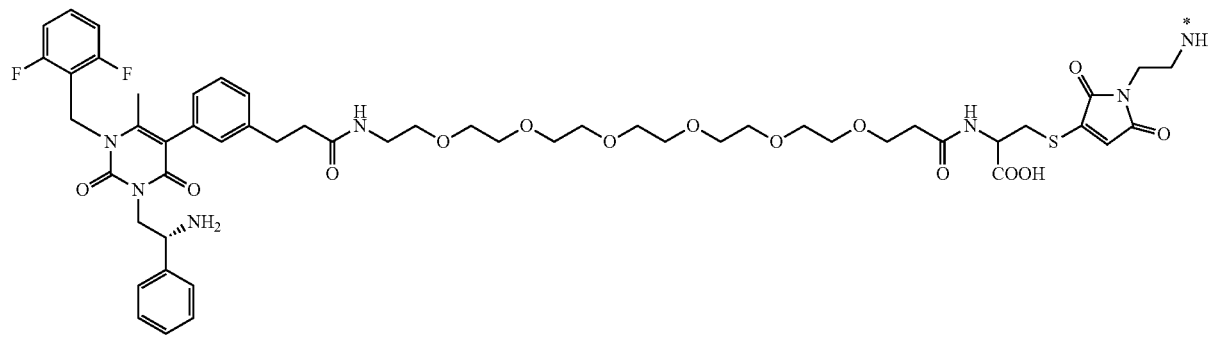 [SMILES: Cc1c(-c2cccc(CCC(=O)NCCOCCOCCOCCOCCOCCOCCC(=O)NC(CSC3=CC(=O)N(CCN)C3=O)C(=O)O)c2)c(=O)n(C[C@H](N)c2ccccc2)c(=O)n1Cc1c(F)cccc1F]
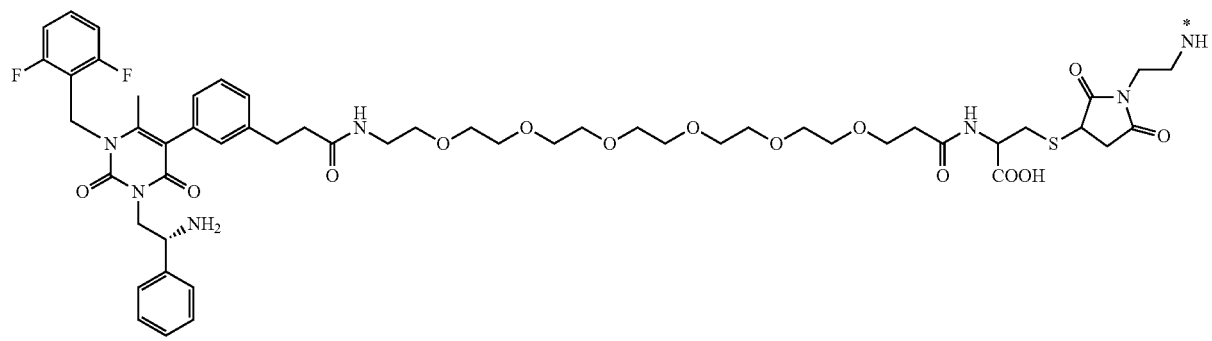 [SMILES: Cc1c(-c2cccc(CCC(=O)NCCOCCOCCOCCOCCOCCOCCC(=O)NC(CSC3CC(=O)N(CCN)C3=O)C(=O)O)c2)c(=O)n(C[C@H](N)c2ccccc2)c(=O)n1Cc1c(F)cccc1F]

wherein * represents a covalent bond to the rest of the conjugate.
34. The conjugate of clause 1, or a pharmaceutically acceptable salt thereof, comprising the formula
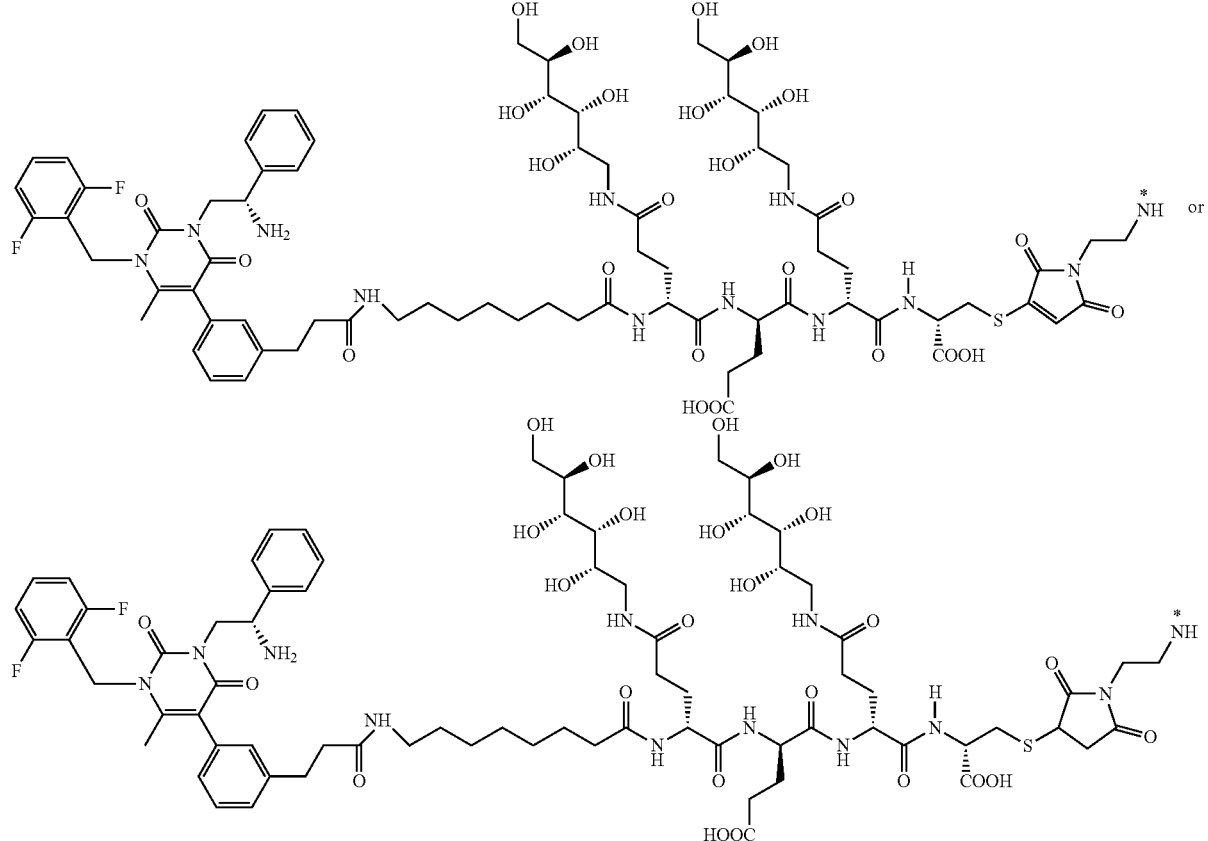
wherein * represents a covalent bond to the rest of the conjugate.
35. The conjugate of clause 1, or a pharmaceutically acceptable salt thereof, comprising the formula
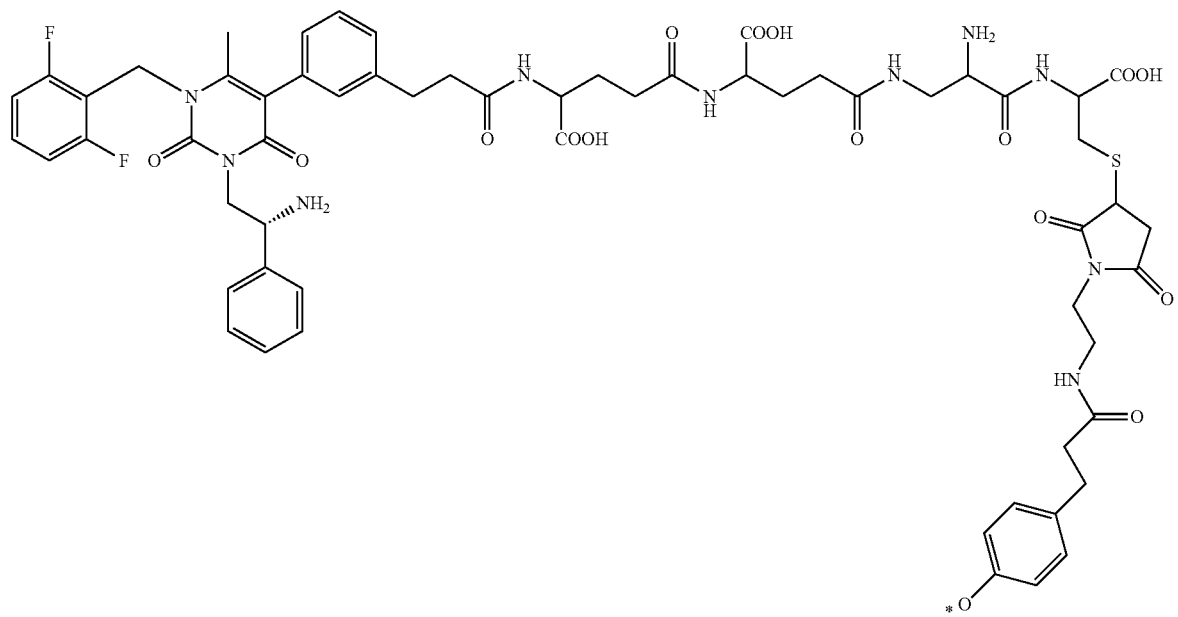 [SMILES: Cc1c(-c2cccc(CCC(=O)NC(CCC(=O)NC(CCC(=O)NCC(N)C(=O)NC(CSC3CC(=O)N(CCNC(=O)CCc4ccc(O)cc4)C3=O)C(=O)O)C(=O)O)C(=O)O)c2)c(=O)n(C[C@H](N)c2ccccc2)c(=O)n1Cc1c(F)cccc1F]

wherein * represents a covalent bond to the rest of the conjugate.
36. The conjugate of clause 1, or a pharmaceutically acceptable salt thereof, comprising the formula
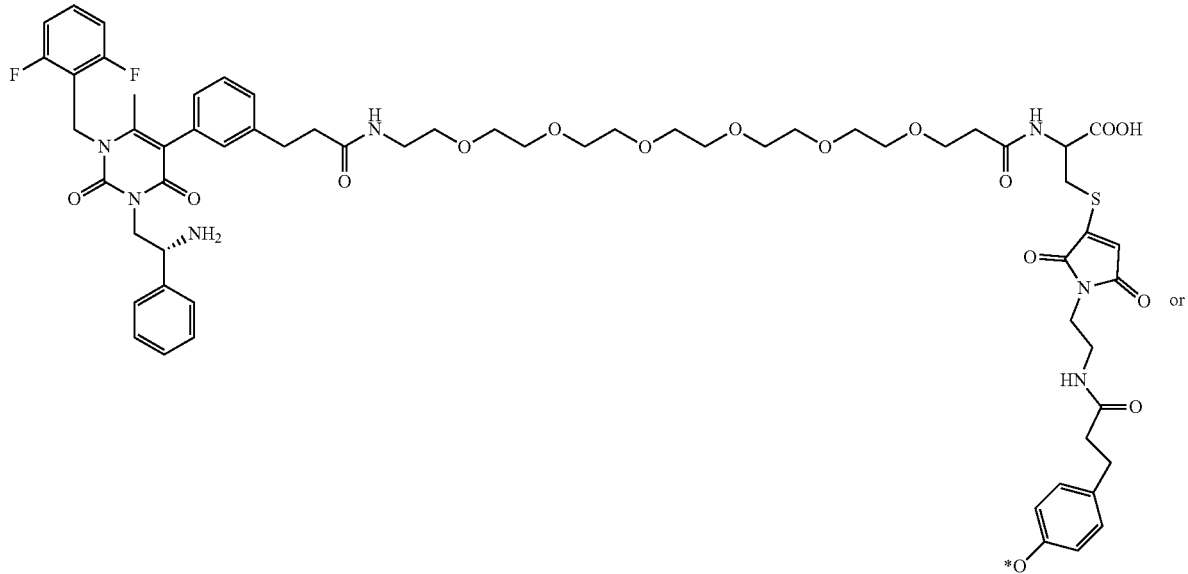
or
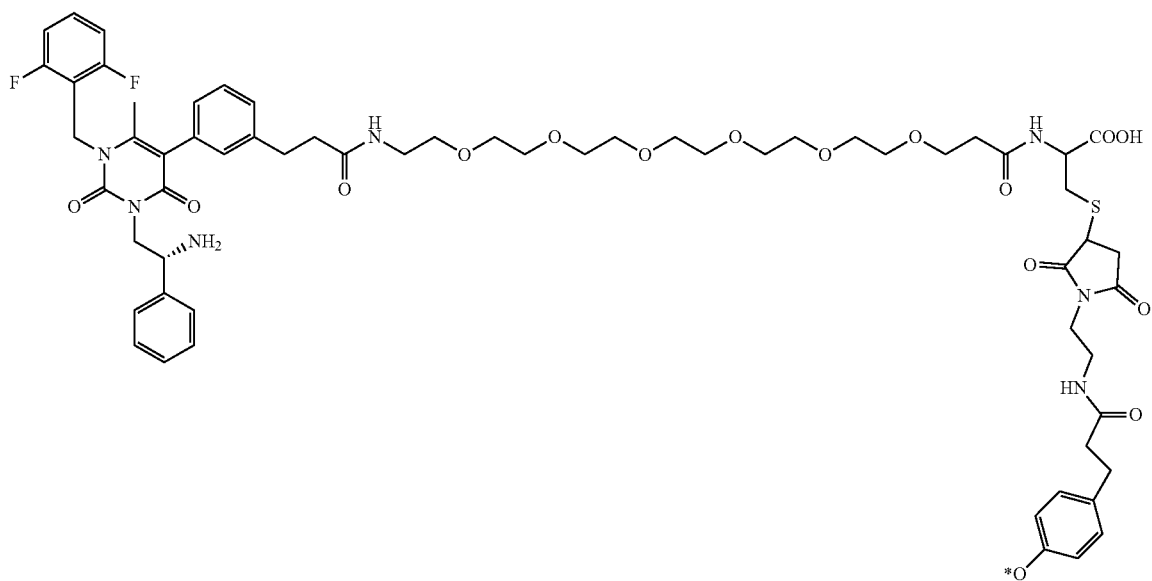

wherein * represents a covalent bond to the rest of the conjugate.

37. The conjugate of clause 1, or a pharmaceutically acceptable salt thereof, comprising the formula vinca alkaloid, a cryptophycin, bortezomib, thiobortezomib, a tubulysin, aminopterin, rapamycin, paclitaxel, docetaxel, doxorubicin, daunorubicin, everolimus, α-amanatin, verucarin, didemnin B, geldanomycin, purvalanol A, ispinesib,

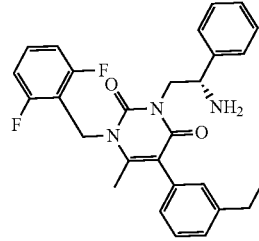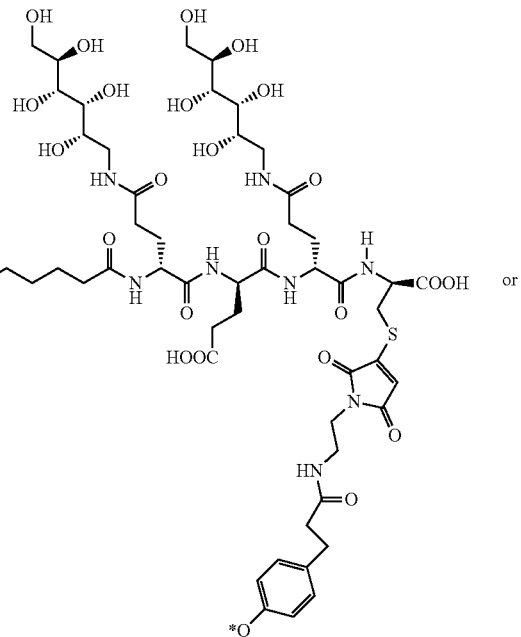

or

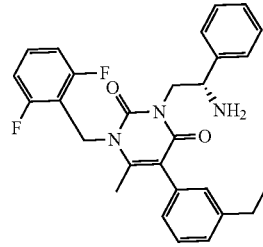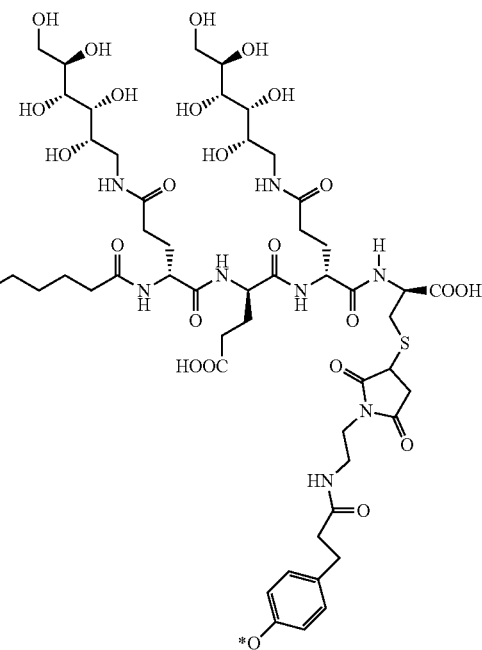

wherein * represents a covalent bond to the rest of the conjugate.

38. The conjugate of any one of the preceding clauses, wherein A is a drug selected from the group consisting of a budesonide, dasatinib, an epothilone, a maytansine, and a tyrosine kinase inhibitor.

39. The conjugate of any one of the preceding clauses, or a pharmaceutically acceptable salt thereof, wherein the drug is a tubulysin.

40. The conjugate of any one of the preceding clauses, or a pharmaceutically acceptable salt thereof, wherein the drug is a tetrapeptide of the formula

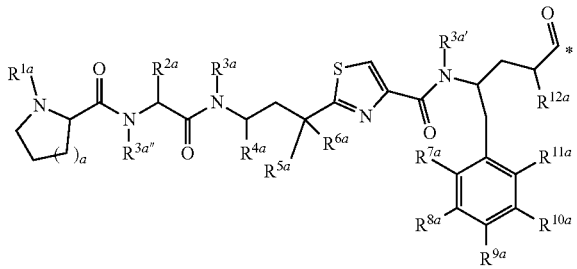

wherein $R^{1a}$, $R^{3a}$, $R^{3a'}$ and $R^{3a''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, $-OR^{13a}$, $-OC(O)R^{13a}$, $-OC(O)NR^{13a}R^{13a'}$, $-OS(O)R^{13a}$, $-OS(O)_2R^{13a}$, $-SR^{13a}$, $-SC(O)R^{13a}$, $-S(O)R^{13a}$, $-S(O)_2R^{13a}$, $-S(O)_2OR^{13a}$, $-S(O)NR^{13a}R^{13a'}$, $-S(O)_2NR^{13a}R^{13a'}$, $-OS(O)NR^{13a}R^{13a'}$, $-OS(O)_2NR^{13a}R^{13a'}$, $-NR^{13a}R^{13a'}$, $-NR^{13a}C(O)R^{14a}$, $-NR^{13a}C(O)OR^{14a}$, $-NR^{13a}C(O)NR^{14a}R^{14a'}$, $-NR^{13a}S(O)R^{14a}$, $-NR^{13a}S(O)_2R^{14a}$, $-NR^{13a}S(O)NR^{13a}R^{14a'}$, $-NR^{13a}S(O)_2NR^{14a}R^{14a'}$, $-P(O)(OR^{13a})_2$, $-C(O)R^{13a}$, $-C(O)OR^{13a}$ or $-C(O)NR^{13a}R^{13a'}$;

$R^{2a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ and $R^{6a}$ are each independently selected from the group consisting of H, halogen, $C_1$-$C_6$ alkyl, $C_2$-$C_6$ alkenyl, $C_2$-$C_6$ alkynyl, $-OR^{15a}$, $-SR^{15a}$ and $-NR^{15a}R^{15a'}$, wherein each hydrogen atom in $C_1$-$C_6$ alkyl, $C_2$-$C_6$ alkenyl and $C_2$-$C_6$ alkynyl is independently optionally substituted by halogen, $-OR^{16a}$, $-SR^{16a}$, $-NR^{16a}R^{16a'}$, $-C(O)R^{16a}$, $-C(O)OR^{16a}$ or $-C(O)NR^{16a}R^{16a'}$; or $R^{5a}$ and $R^{6a}$ taken together with the carbon atom to which they are attached form a $-C(O)-$;

each $R^{7a}$, $R^{8a}$, $R^{9a}$, $R^{10a}$ and $R^{11a}$ is independently selected from the group consisting of H, halogen, $C_1$-$C_6$ alkyl, $C_2$-$C_6$ alkenyl, $C_2$-$C_6$ alkynyl, $-CN$, $-NO_2$, $-NCO$, $-OR^{17a}$, $-SR^{17a}$, $-S(O)_2OR^{17a}$, $-NR^{17a}R^{17a'}$, $-P(O)(OR^{17}a)_2$, $-C(O)R^{17a}$, $-C(O)OR^{17a}$ and $-C(O)NR^{17a}R^{17a'}$, wherein each hydrogen atom in $C_1$-$C_6$ alkyl, $C_2$-$C_6$ alkenyl and $C_2$-$C_6$ alkynyl is independently optionally substituted by halogen, $-OR^{18a}$, $-SR^{18a}$, $-NR^{18a}R^{8a'}$, $-C(O)R^{18a}$, $-C(O)OR^{18a}$ or $-C(O)NR^{18a}R^{18a'}$;

each $R^{13a}$, $R^{13a'}$, $R^{14a}$, $R^{14a'}$, $R^{15a}$, $R^{15a'}$, $R^{16a}$, $R^{16a'}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, $-OH$, $-SH$, $-NH_2$ or $-CO_2H$;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl $-C(O)R^{19a}$, $-P(O)(OR^{19a})_2$, and $-S(O)_2OR^{19a}$, each $R^{19a}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

a is 1, 2 or 3; and

* represents a covalent bond to the rest of the conjugate.

41. The conjugate of any one of the preceding clauses, or a pharmaceutically acceptable salt thereof, wherein D is a tetrapeptide of the formula

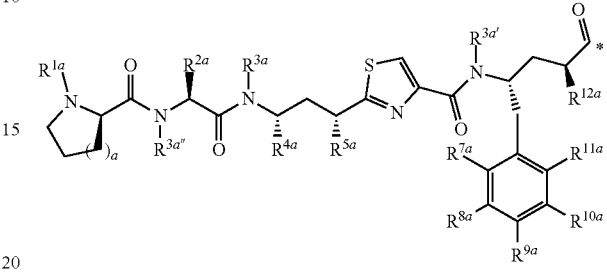

wherein $R^{1a}$, $R^{3a}$, $R^{3a'}$ and $R^{3a'}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, $-OR^{13a}$, $-OC(O)R^{13a}$, $-OC(O)NR^{13a}R^{13a'}$, $-OS(O)R^{13a}$, $-OS(O)_2R^{13a}$, $-SR^{13a}$, $-SC(O)R^{13a}$, $-S(O)R^{13a}$, $-S(O)_2R^{13a}$, $-S(O)_2OR^{13a}$, $-S(O)NR^{13a}R^{13a'}$, $-S(O)_2NR^{13a}R^{13a'}$, $-OS(O)NR^{13a}R^{13a'}$, $-OS(O)_2NR^{13a}R^{13a'}$, $-NR^{13a}R^{13a'}$, $-NR^{13a}C(O)R^{14a}$, $-NR^{13a}C(O)OR^{14a}$, $-NR^{13a}C(O)NR^{14a}R^{14a'}$, $-NR^{13a}S(O)R^{14a}$, $-NR^{13a}S(O)_2R^{14a}$, $-NR^{13a}S(O)NR^{13a}R^{14a'}$, $-NR^{13a}S(O)_2NR^{14a}R^{14a'}$, $-P(O)(OR^{13}a)_2$, $-C(O)R^{13a}$, $-C(O)OR^{13a}$ or $-C(O)NR^{13a}R^{13a'}$;

$R^{2a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ is selected from the group consisting of H, halogen, $C_1$-$C_6$ alkyl, $C_2$-$C_6$ alkenyl, $C_2$-$C_6$ alkynyl, $-OR^{15a}$, $-SR^{15a}$ and $-NR^{15a}R^{15a'}$, wherein each hydrogen atom in $C_1$-$C_6$ alkyl, $C_2$-$C_6$ alkenyl and $C_2$-$C_6$ alkynyl is independently optionally substituted by halogen, $-OR^{16a}$, $-SR^{16a}$, $-NR^{16a}R^{16a'}$, $-C(O)R^{16a}$, $-C(O)OR^{16a}$ or $-C(O)NR^{16a}R^{16a'}$;

each $R^{7a}$, $R^{8a}$, $R^{9a}$, $R^{10a}$ and $R^{11a}$ is independently selected from the group consisting of H, halogen, $C_1$-$C_6$ alkyl, $C_2$-$C_6$ alkenyl, $C_2$-$C_6$ alkynyl, $-CN$, $-NO_2$, $-NCO$, $-OR^{17a}$, $-SR^{17a}$, $-S(O)_2OR^{17a}$, $-NR^{17a}R^{17a'}$, $-P(O)(OR^{17}a)_2$, $-C(O)R^{17a}$, $-C(O)OR^{17a}$ and $-C(O)NR^{17a}R^{17a'}$ wherein each hydrogen atom in $C_1$-$C_6$ alkyl, $C_2$-$C_6$ alkenyl and $C_2$-$C_6$ alkynyl is independently optionally substituted by halogen, $-OR^{18a}$, $-SR^{18a}$, $-NR^{18a}R^{8a'}$, $-C(O)R^{18a}$, $-C(O)OR^{18a}$ or $-C(O)NR^{18a}R^{18a'}$;

each $R^{13a}$, $R^{13a'}$, $R^{14a}$, $R^{14a'}$, $R^{15a}$, $R^{15a'}$, $R^{16a}$, $R^{16a'}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, $-OH$, $-SH$, $-NH_2$ or $-CO_2H$;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —C(O)$R^{19a}$, —P(O)(O$R^{19a}$)$_2$, and —S(O)$_2$O$R^{19a}$, each $R^{19a}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

a is 1, 2 or 3; and

* represents a covalent bond to the rest of the conjugate.

42. The conjugate of any one of the preceding clauses, or a pharmaceutically acceptable salt thereof, wherein D is a tetrapeptide of the formula

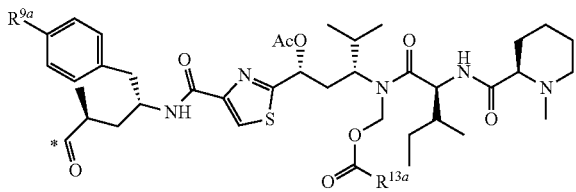

wherein $R^{9a}$ is selected from the group consisting of H, halogen, $C_1$-$C_6$ alkyl, $C_2$-$C_6$ alkenyl, $C_2$-$C_6$ alkynyl, —CN, —NO$_2$, —NCO, —O$R^{17a}$, —S$R^{17a}$, —S(O)$_2$O$R^{17a}$, —N$R^{17a}R^{17a'}$, —P(O)(O$R^{17a}$)$_2$, —C(O)$R^{17a}$, —C(O)O$R^{17a}$ and —C(O)N$R^{17a}R^{17a'}$, wherein each hydrogen atom in $C_1$-$C_6$ alkyl, $C_2$-$C_6$ alkenyl and $C_2$-$C_6$ alkynyl is independently optionally substituted by halogen, —O$R^{18a}$, —S$R^{18a}$, —N$R^{18a}R^{18a'}$, —C(O)$R^{18a}$, —C(O)O$R^{18a}$ or —C(O)N$R^{18a}R^{18a'}$;

each $R^{13a}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —NH$_2$ or —CO$_2$H;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —C(O)$R^{19a}$, —P(O)(O$R^{19a}$)$_2$, and —S(O)$_2$O$R^{19a}$, each $R^{19a}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and

* represents a covalent bond to the rest of the conjugate.

43. The conjugate of any one of the preceding clauses, or a pharmaceutically acceptable salt thereof, wherein A is a naturally occurring tubulysin.

44. The conjugate of clause 43, or a pharmaceutically acceptable salt thereof, wherein A is selected from the group consisting of tubulysin A, tubulysin B, tubulysin C, tubulysin D, tubulysin E, tubulysin F, tubulysin G, tubulysin H and tubulysin I.

45. The conjugate of any one of the preceding clauses, or a pharmaceutically acceptable salt thereof, wherein the drug is tubulysin B.

46. The conjugate of any one of the preceding clauses, or a pharmaceutically acceptable salt thereof, wherein A is of the formula

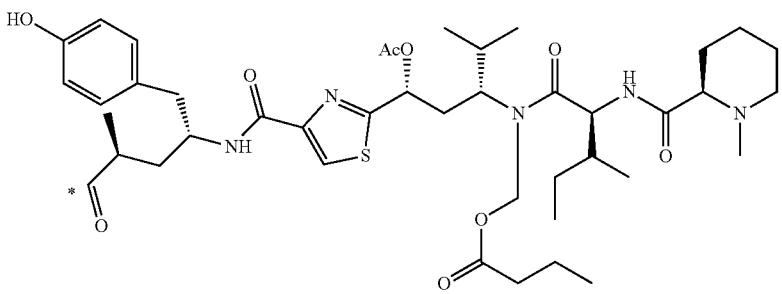 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C=O)cs1)C(C)C]

wherein * represents a covalent bond to the rest of the conjugate.

47. The conjugate of any one of the preceding clauses, or a pharmaceutically acceptable salt thereof, wherein A is of the formula

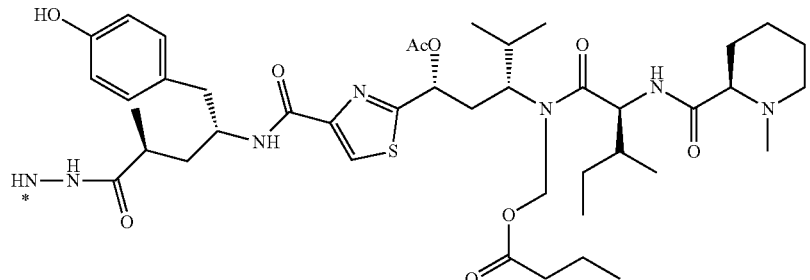

wherein * represents a covalent bond to the rest of the conjugate.

48. The conjugate of any one of clauses 1 to 34, or a pharmaceutically acceptable salt thereof, wherein A is an imaging agent.

49. The conjugate of any one of clauses 1 to 34, or a pharmaceutically acceptable salt thereof, wherein A is an imaging agent selected from the group consisting of a rhodamine dye, a fluorescein dye, a PET imaging agent, or a radiolabeled agent.

50. The conjugate of clause 48 or 49, or a pharmaceutically acceptable salt thereof, wherein A is selected from the group consisting of S0456, 5-carboxytetramethylrhodamine (5-TAMRA), rhodamine B, rhodamine 6G, TRITC, Texas Red, rhodamine 123, sulforhodamine 101, fluorescein, 5-amino-fluorescein, 6-amino-fluorescein, fluorescein isocyanate (FITC), NHS-fluorescein, Oregon Green, Tokyo Green, Singapore Green, and Philadelphia Green.

51. The conjugate of any one of clauses 1 to 34, or a pharmaceutically acceptable salt thereof, wherein A is a radioactive isotope, such as a radioactive isotope of a metal, coordinated to a chelating group.

52. The conjugate of clause 51, or a pharmaceutically acceptable salt thereof, wherein the chelating group of the formula

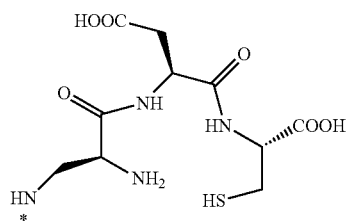

wherein * represents a covalent bond to the rest of the conjugate.

53. The conjugate of clause 51, or a pharmaceutically acceptable salt thereof, wherein the chelating group comprises a radioactive metal isotope selected from the group consisting of an isotope of technetium, rhenium, gallium, gadolinium, indium and copper coordinated thereto.

54. The conjugate of clause 51, or a pharmaceutically acceptable salt thereof, wherein the chelating group comprises a radioactive metal isotope selected from the group consisting of $^{111}$In, $^{99m}$Tc, $^{64}$Cu, $^{67}$Cu, $^{67}$Ga and $^{68}$Ga coordinated thereto.

55. The conjugate of clause 1, selected from the group consisting of

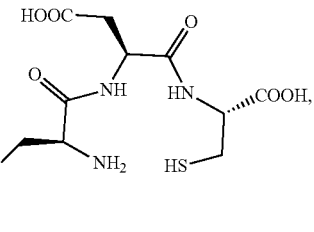

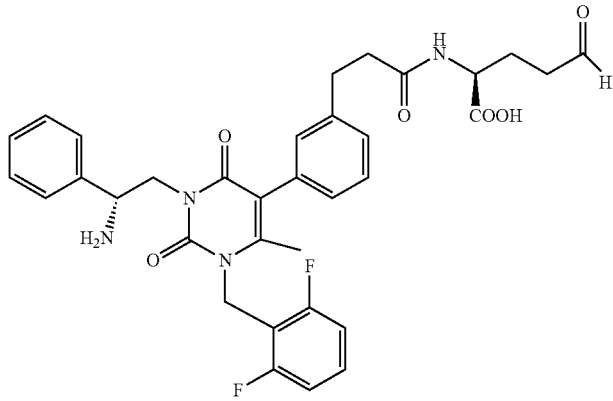

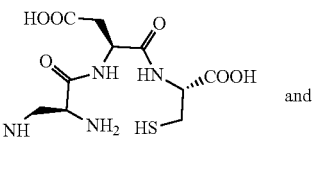

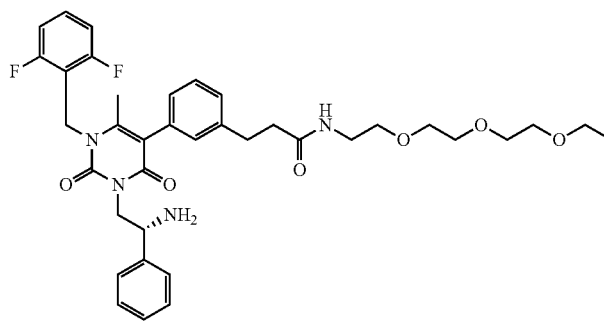

25

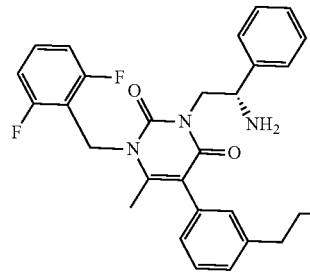

26

-continued

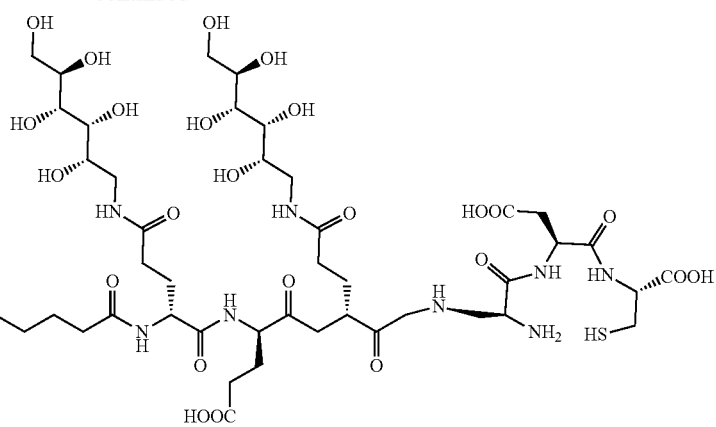

or a pharmaceutically acceptable salt thereof

56. The conjugate of clause 55, or a pharmaceutically acceptable salt thereof, wherein the conjugate comprises a radioactive metal isotope selected from the group consisting of $^{111}$In, $^{99m}$Tc, $^{64}$Cu, $^{67}$Cu, $^{67}$Ga and $^{68}$Ga coordinated thereto.

57. The conjugate of clause 56, or a pharmaceutically acceptable salt thereof, wherein the radioactive metal isotope is $^{99m}$Tc.

58. The conjugate of clause 1, selected from the group consisting of

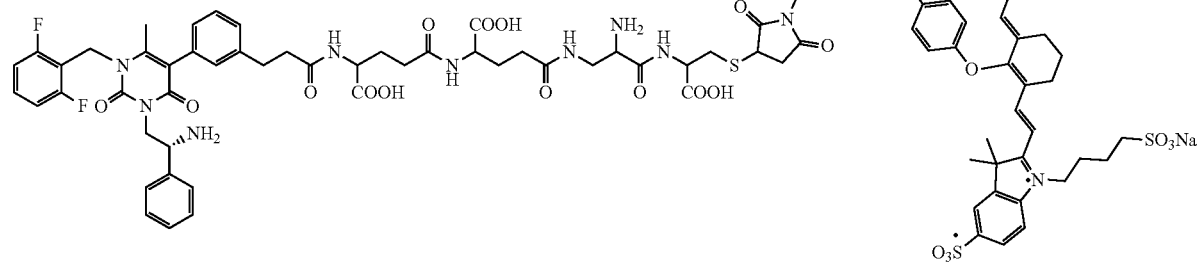

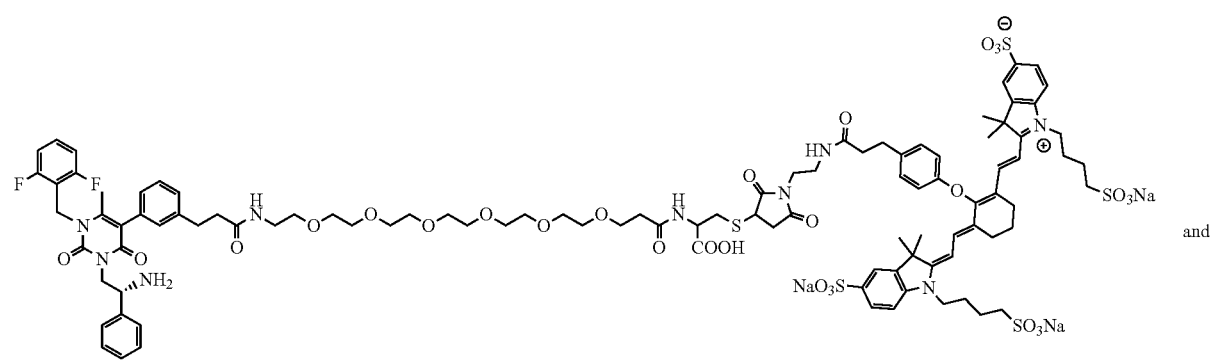

and

-continued

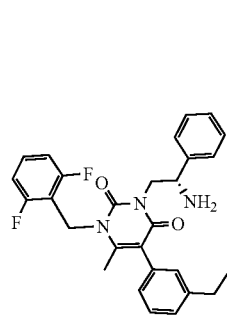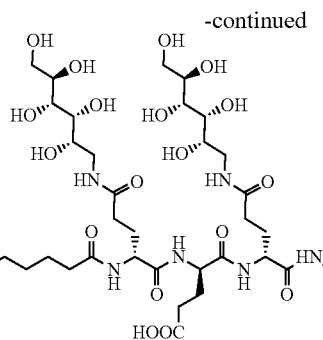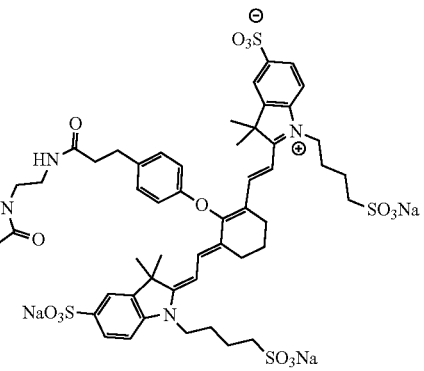

or a pharmaceutically acceptable salt thereof.

59. The conjugate of clause 1, of the formula

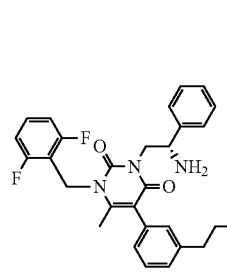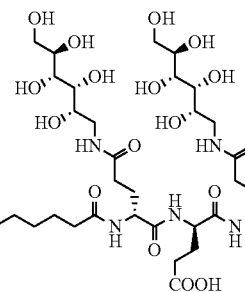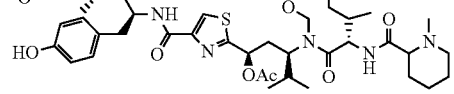

or a pharmaceutically acceptable salt thereof.

60. A pharmaceutical composition comprising a conjugate of any of the preceding clauses, or a pharmaceutically acceptable salt thereof, and optionally at least one pharmaceutically acceptable excipient.

61. A method of treating cancer in a subject, comprising,
a. administering to the subject an effective amount of a conjugate or composition according to any one of clauses 1 to 47 or 59; or a pharmaceutically acceptable salt thereof.

62. The method of clause 61, wherein the subject has a LHRH-R expressing cancer.

63. The method of clause 61 or 62, wherein LHRH-R expressing cancer is primary or metastatic.

64. The method of any one of clauses 61 to 63, wherein the cancer is selected from the group consisting of prostate, endometrial, skin, pancreatic, breast, kidney, ovarian and brain cancer.

65. A conjugate according to any one of clause 1 to 47 or 59, or a pharmaceutically acceptable salt thereof, for use in a method of treating LHRH-R expressing cancer in a subject.

66. The conjugate of clause 65, wherein the method comprises administering to the subject an amount of the conjugate effective for treating the LHRH-R expressing cancer.

67. The conjugate of clause 65 or 66, wherein the LHRH-R expressing cancer is selected from the group consisting of prostate, endometrial, skin, pancreatic, breast, kidney, ovarian and brain cancer.

68. Use of a conjugate according to any one of clauses 1 to 47 or 59, or a pharmaceutically acceptable salt thereof, in the preparation of a medicament useful for treating LHRH-R expressing cancer in a subject.

69. The use of clause 68, wherein the LHRH-R expressing cancer is selected from the group consisting of prostate, endometrial, skin, pancreatic, breast, kidney, ovarian and brain cancer.

70. A method of imaging a population of cells in vitro, comprising
a. contacting the cells with a conjugate according to any one of clauses 1 to 37 or 48 to 58, to provide labelled cells, and b. visualizing the labelled cells.

71. A conjugate according to any one of clauses 1 to 37 or 48 to 58, for use in a method of imaging a population of cells in vitro.

72. The conjugate of clause 71, wherein the method comprises
a. contacting the cells with a conjugate according to any one of clauses 1 to 37 or 48 to 58, to provide labelled cells, and b. visualizing the labelled cells.

73. A method of imaging a population of cells in vivo, comprising
a. administering to a patient an effective amount of a conjugate according to any one of clauses 1 to 37 or 48 to 58, or a pharmaceutically acceptable salt thereof, to provide labelled cells; and b. visualizing the labelled cells by imaging.

74. A conjugate according to any one of clauses 1 to 37 or 48 to 58, for use in a method of imaging a population of cells in vitro.

75. The conjugate of clause 74, wherein the method comprises a. administering to a patient an effective amount of a conjugate according to any one of clauses 1 to 37 or 48 to 58, or a pharmaceutically acceptable salt thereof, to provide labelled cells; and b. visualizing the labelled cells by imaging.

DEFINITIONS

Figure 1A:
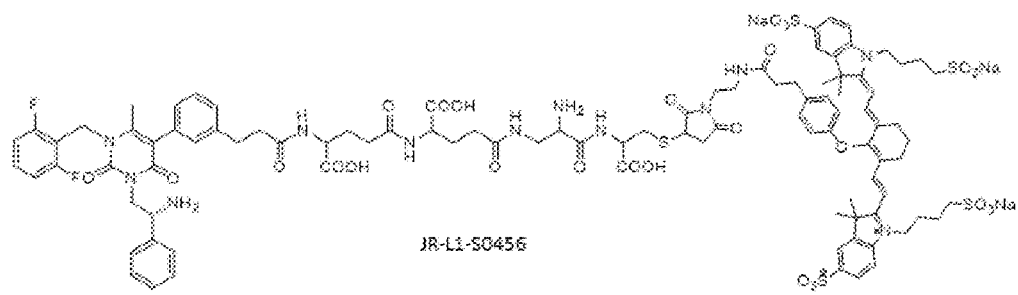
FIGS. 1A-1C show the chemical structure (FIG. 1A) and an LC/MS trace (FIGS. 1B and 1C) for JR-L1-S0456.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$, Illustratively, such particularly limited length alkyl groups, including $C_1$-$C_5$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like. In other embodiments, an "alkyl" group can be combined with another group, such as an aryl group, for example $C_6$-$C_{10}$ aryl-($C_1$-$C_6$ alkyl), which provides for a group such as benzyl (i.e. $C_6H_5$—$CH_2$—).

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_5$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_5$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic group of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, an all-carbon 5-member/6-member or 6-member/6-member fused bicyclic ring, or a multicyclic fused ring (a "fused" ring system means that each ring in the system shares an adjacent pair of carbon atoms with each other ring in the system) group where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_6$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like.

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1,2,3,4-tetrahydropyridinyl, and the like.

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like.

As used herein, "hydroxy" or ""hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "trihalomethyl" refers to a methyl group having three halo substituents, such as a trifluoromethyl group.

As used herein, "cyano" refers to a —CN group.

As used herein, "sulfinyl" refers to a —S(O)R" group, where R" is any R group as described in the various embodiments provided herein, or R" may be a hydroxyl group.

As used herein, "sulfonyl" refers to a —S(O)₂R" group, where R" is any R group as described in the various embodiments provided herein, or R" may be a hydroxyl group.

As used herein, "S-sulfonamido" refers to a —S(O)₂NR"R" group, where R" is any R group as described in the various embodiments provided herein.

As used herein, "N-sulfonamido" refers to a —NR"S(O)₂R" group, where R" is any R group as described in the various embodiments provided herein.

As used herein, "O-carbamyl" refers to a —OC(O)NR"R" group, where R" is any R group as described in the various embodiments provided herein.

As used herein, "N-carbamyl" refers to an R"OC(O)NR"— group, where R" is any R group as described in the various embodiments provided herein.

As used herein, "O-thiocarbamyl" refers to a —OC(S)NR"R" group, where R" is any R group as described in the various embodiments provided herein.

As used herein, "N-thiocarbamyl" refers to a R"OC(S)NR"— group, where R" is any R group as described in the various embodiments provided herein.

As used herein, "amino" refers to an —NR"R" group, where R" is any R group as described in the various embodiments provided herein.

As used herein, "C-amido" refers to a —C(O)NR"R" group, where R" is any R group as described in the various embodiments provided herein.

As used herein, "N-amido" refers to a R"C(O)NR"— group, where R" is any R group as described in the various embodiments provided herein.

As used herein, "nitro" refers to a —NO₂ group.

As used herein, "bond" refers to a covalent bond.

As used herein, "optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, "amino acid" (a.k.a. "AA") means any molecule that includes an alpha-carbon atom covalently bonded to an amino group and an acid group. The acid group may include a carboxyl group. "Amino acid" may include molecules having one of the formulas:

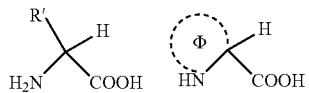

wherein R' is a side group and Φ includes at least 3 carbon atoms. "Amino acid" includes stereoisomers such as the D-amino acid and L-amino acid forms. Illustrative amino acid groups include, but are not limited to, the twenty endogenous human amino acids and their derivatives, such as lysine (Lys), asparagine (Asn), threonine (Thr), serine (Ser), isoleucine (Ile), methionine (Met), proline (Pro), histidine (His), glutamine (Gln), arginine (Arg), glycine (Gly), aspartic acid (Asp), glutamic acid (Glu), alanine (Ala), valine (Val), phenylalanine (Phe), leucine (Leu), tyrosine (Tyr), cysteine (Cys), tryptophan (Trp), phosphos-erine (PSER), sulfo-cysteine, arginosuccinic acid (ASA), hydroxyproline, phosphoethanolamine (PEA), sarcosine (SARC), taurine (TAU), carnosine (CARN), citrulline (CIT), anserine (ANS), 1,3-methyl-histidine (ME-HIS), alpha-amino-adipic acid (AAA), beta-alanine (BALA), ethanolamine (ETN), gamma-amino-butyric acid (GABA), beta-amino-isobutyric acid (BAIA), alpha-amino-butyric acid (BABA), L-allo-cystathionine (cystathionine-A; CYSTA-A), L-cystathionine (cystathionine-B; CYSTA-B), cystine, allo-isoleucine (ALLO-ILE), DL-hydroxylysine (hydroxylysine (I)), DL-allo-hydroxylysine (hydroxylysine (2)), ornithine (ORN), homocystine (HCY), and derivatives thereof. In connection with the embodiments described herein, amino acids can be covalently attached to other portions of the conjugates described herein through their alpha-amino and carboxy functional groups (i.e. in a peptide bond configuration), or through their side chain functional groups (such as the side chain carboxy group in glutamic acid) and either their alpha-amino or carboxy functional groups. It will be understood that amino acids, when used in connection with the conjugates described herein, may exist as zwitterions in a conjugate in which they are incorporated.

As used herein, "prodrug" refers to a compound that can be administered to a subject in a pharmacologically inactive form which then can be converted to a pharmacologically active form through a normal metabolic process, such as hydrolysis of an oxazolidine. It will be understood that the metabolic processes through which a prodrug can be converted to an active drug include, but are not limited to, one or more spontaneous chemical reaction(s), enzyme-catalyzed chemical reaction(s), and/or other metabolic chemical reaction(s), or a combination thereof. It will be appreciated that understood that a variety of metabolic processes are known in the art, and the metabolic processes through which the prodrugs described herein are converted to active drugs are non-limiting. A prodrug can be a precursor chemical compound of a drug that has a therapeutic effect on a subject.

As used herein, the term "therapeutically effective amount" refers to an amount of a drug or pharmaceutical agent that elicits the biological or medicinal response in a subject (i.e. a tissue system, animal or human) that is being sought by a researcher, veterinarian, medical doctor or other clinician, which includes, but is not limited to, alleviation of the symptoms of the disease or disorder being treated. In one aspect, the therapeutically effective amount is that amount of an active which may treat or alleviate the disease or symptoms of the disease at a reasonable benefit/risk ratio applicable to any medical treatment. In another aspect, the therapeutically effective amount is that amount of an inactive prodrug which when converted through normal metabolic processes to produce an amount of active drug capable of eliciting the biological or medicinal response in a subject that is being sought.

It is also appreciated that the dose, whether referring to monotherapy or combination therapy, is advantageously selected with reference to any toxicity, or other undesirable side effect, that might occur during administration of one or more of the conjugates described herein. Further, it is appreciated that the co-therapies described herein may allow for the administration of lower doses of conjugates that show such toxicity, or other undesirable side effect, where those lower doses are below thresholds of toxicity or lower in the therapeutic window than would otherwise be administered in the absence of a cotherapy.

As used herein, "administering" includes all means of introducing the conjugates and compositions described herein to the host animal, including, but are not limited to, oral (po), intravenous (iv), intramuscular (im), subcutaneous (sc), transdermal, inhalation, buccal, ocular, sublingual, vaginal, rectal, and the like. The conjugates and compositions described herein may be administered in unit dosage forms and/or formulations containing conventional nontoxic pharmaceutically-acceptable carriers, adjuvants, and/or vehicles.

As used herein "pharmaceutical composition" or "composition" refers to a mixture of one or more of the conjugates described herein, or pharmaceutically acceptable salts, solvates, hydrates thereof, with other chemical components, such as pharmaceutically acceptable excipients. The purpose of a pharmaceutical composition is to facilitate administration of a conjugate to a subject. Pharmaceutical compositions suitable for the delivery of conjugates described and methods for their preparation will be readily apparent to those skilled in the art. Such compositions and methods for their preparation may be found, for example, in 'Remington's Pharmaceutical Sciences', 19th Edition (Mack Publishing Company, 1995).

As used herein and in the appended claims, the singular forms "a," "an," and "the" include plural reference unless the context clearly indicates otherwise.

Unless defined otherwise, all technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

DETAILED DESCRIPTION

Several embodiments of the invention are described by the following enumerated clauses and any combination of these embodiments with the embodiments described in this Detailed Description section is contemplated. It is to be understood that elements and features of the various representative embodiments described below may be combined in different ways to produce new embodiments that likewise fall within the scope of the present teachings.

In each of the foregoing and each of the following embodiments, it is to be understood that the formulae include and represent not only all pharmaceutically acceptable salts of the conjugates, but also include any and all hydrates and/or solvates of the conjugate formulae. It is appreciated that certain functional groups, such as the hydroxy, amino, and like groups form complexes and/or coordination conjugates with water and/or various solvents, in the various physical forms of the conjugates. Accordingly, the above formulae are to be understood to include and represent those various hydrates and/or solvates. It is also to be understood that the non-hydrates and/or non-solvates of the conjugate formulae are described by such formula, as well as the hydrates and/or solvates of the conjugate formulae.

It will be appreciated that LHRH-R antagonists useful in connection with the present disclosure are not particularly limited by structure. Useful LHRH-R antagonists can be any drug or compound that shows binding affinity for LHRH-R.

In some embodiments, the LHRH-R antagonist is of the formula

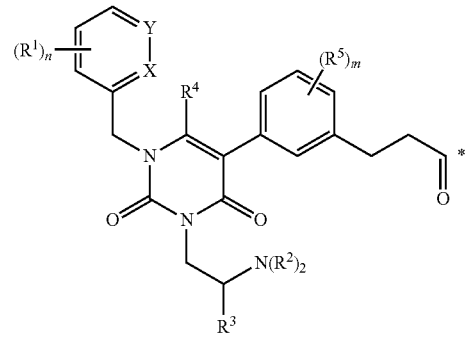

wherein
each $R^1$ is independently halogen, $C_1$-$C_6$ alkyl or —$OC_1$-$C_6$ alkyl; each $R^2$ is independently H, $C_1$-$C_6$ alkyl or $C_3$-$C_6$ cycloalkyl; $R^3$ is $C_1$-$C_6$ alkyl, $C_3$-$C_6$ cycloalkyl, $C_6$-$C_{10}$ aryl or $C_1$-$C_6$ alkyl-($C_6$-$C_{10}$ aryl); $R^4$ is $C_1$-$C_6$ alkyl; each $R^5$ is independently selected from the group consisting of halogen, $C_1$-$C_6$ alkyl, —$OC_1$-$C_6$ alkyl, —$SC_1$-$C_6$ alkyl and —$OC_6$-$C_{10}$ aryl; X and Y are each independently N, CH or $CR^1$; provided that when X is N, Y is CH or $CR^1$, and when Y is N, X is CH or $CR^1$; m is an integer from 0 to 4; n is an integer from 0 to 3; and * represents a covalent bond to L; L is a linker; and A is a drug or an imaging agent; or a pharmaceutically acceptable salt thereof.

In some embodiments, n is 0. In some embodiments, n is 1. In some embodiments, n is 2. In some embodiments, n is 3. In some embodiments, m is 0. In some embodiments, m is 1. In some embodiments, m is 2.

In some embodiments, $R^1$, when present, is halogen. In some embodiments, $R^1$, when present, is F. In some embodiments, $R^1$, when present, is Cl. In some embodiments, $R^1$, when present, is $CH_3$. In some embodiments, $R^1$, when present, is —$OCH_3$. In some embodiments, each $R^1$, when present, is F in the 2- and 6-position of the ring to which each $R^1$ is attached. In some embodiments, each $R^1$, when present, is F in a substitution pattern to provide a 2,6-difluorophenyl.

In some embodiments, $R^2$ is H. In some embodiments, $R^2$ is —$CH_3$. In some embodiments, $R^3$ is $C_1$-$C_6$ alkyl-($C_6$-$C_{10}$ aryl). In some embodiments, $R^3$—$CH_2$—$C_6H_5$. In some embodiments, $R^3$ is $C_1$-$C_6$ alkyl. In some embodiments, $R^3$ is $C_3$-$C_6$ cycloalkyl. In some embodiments, $R^4$ is methyl. In some embodiments, each $R^5$, when present, is F, Cl, —$CH_3$, —$OCH_3$, —$OC_6H_5$ or —$SC_6H_5$. In some embodiments, X is N and Y is CH. In some embodiments, Y is N and X is CH. In some embodiments, X is $CR^1$ and Y is CH or $CR^1$. In some embodiments, X is —CF and Y is CH.

In some embodiments, B is of the formula

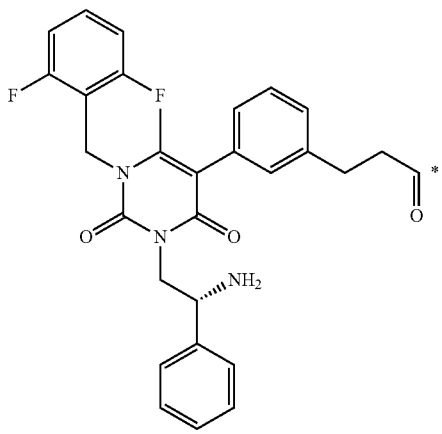 [SMILES: Cc1c(-c2cccc(CCC=O)c2)c(=O)n(C[C@H](N)c2ccccc2)c(=O)n1Cc1c(F)cccc1F]

wherein * represents a covalent bond to L.

It will be appreciated that linkers useful in connection with the present disclosure are not particularly limited by structure. Useful linkers can be of a wide range of structures and of any combination of the linker parts described herein.

In some embodiments, the linker comprises a releasable linker where the term "releasable linker" refers to a linker that includes at least one bond that can be broken under physiological conditions, such as a pH-labile, acid-labile, base-labile, oxidatively labile, metabolically labile, biochemically labile, or enzyme-labile bond. It is appreciated that such physiological conditions resulting in bond breaking do not necessarily include a biological or metabolic process, and instead may include a standard chemical reaction, such as a hydrolysis reaction, for example, at physiological pH, or as a result of compartmentalization into a cellular organelle such as an endosome having a lower pH than cytosolic pH. In some embodiments, the releasable linker comprises a disulfide bond.

In some embodiments, the linker comprises a portion selected from the group consisting of

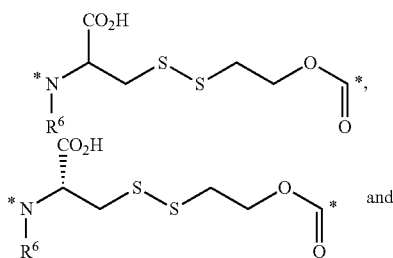

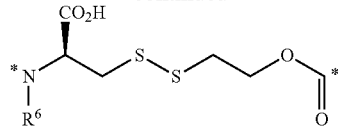

wherein $R^6$ is H or $C_1$-$C_6$ alkyl; and each * represents a covalent bond to the rest of the conjugate.

In some embodiments, the linker comprises a moiety of the formula

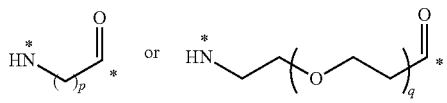

wherein p is an integer from 3 to 10, q is an integer from 3 to 100; and each * represents a covalent bond to the rest of the conjugate.

In some embodiments, the linker comprises a portion selected from the group consisting of

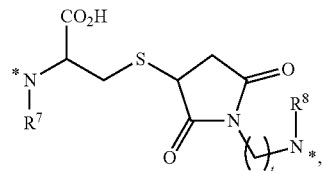

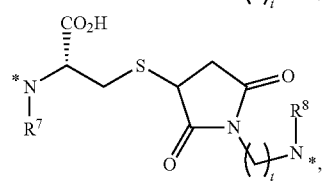

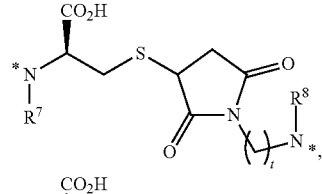

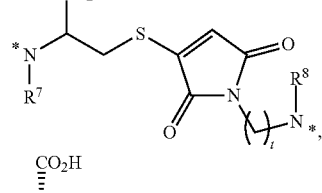

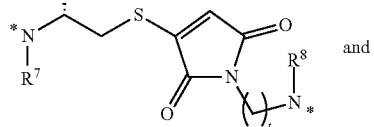 and

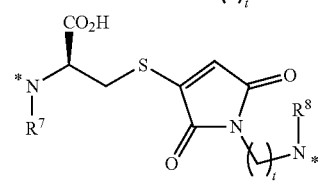

wherein
each of $R^7$ and $R^8$ is independently H or $C_1$-$C_6$ alkyl;
t is an integer from 1 to 8; and
each * represents a covalent bond to the rest of the conjugate.

In some embodiments, a conjugate in accordance with the present teachings includes an imaging agent, such as a near infrared (NIR) dye or a radioactive imaging agent. Representative compounds that may be used as imaging agents in accordance with the present teachings include but are not limited to dyes (e.g., rhodamine dyes, cyanine dyes, fluorescein dyes, etc.), PET imaging agents, radiolabeled agents, and the like. Representative examples of rhodamine dyes include but are not limited to 5-carboxytetramethylrhodamine (5-TAMRA), rhodamine B, rhodamine 6G, TRITC, Texas Red, rhodamine 123, sulforhodamine 101, and the like. Examples of fluorescein dyes include but are not limited to fluorescein, 5-amino-fluorescein, 6-amino-fluorescein, fluorescein isocyanate (FITC), NHS-fluorescein, Oregon Green, Tokyo Green, Singapore Green, Philadelphia Green, and the like. Representative near infrared dyes that may be used in accordance with the present teachings include but are not limited to LS288, IR800, SP054, S0121, KODAK, IRD28, S2076, S0456, and derivatives thereof.

In some embodiments, a radiolabeled agent may be used as an imaging agent in accordance with the present teachings. In some embodiments, a rhodamine dye or fluorescein dye may be isotopically labelled. Examples of isotopes suitable for inclusion in the conjugates include isotopes of hydrogen (e.g., $^2$H and $^3$H), carbon (e.g., $^{11}$C, $^{13}$C, and $^{14}$C), chlorine (e.g., $^{36}$Cl), fluorine (e.g., $^{18}$F), iodine (e.g., $^{123}$I and $^{125}$I), nitrogen (e.g., $^{13}$N and $^{15}$N), oxygen (e.g., $^{15}$O, $^{17}$O, and $^{18}$O), phosphorus (e.g., $^{32}$P), and sulfur (e.g., $^{35}$S).

Certain isotopically-labelled conjugates, for example, those incorporating a radioactive isotope, may be useful in drug and/or substrate tissue distribution studies. The radioactive isotopes tritium (i.e., $^3$H), and carbon-14 (i.e., $^{14}$C) are particularly useful for this purpose in view of their ease of incorporation and ready means of detection.

Substitution with positron emitting isotopes, such as $^{11}$C, $^{18}$F, and $^{13}$N, may be useful in Positron Emission Topography (PET) studies for examining substrate receptor occupancy. Isotopically-labeled conjugates may generally be prepared by conventional techniques known to those skilled in the art or by processes analogous to those described in the accompanying Examples using an appropriate isotopically-labeled reagents in place of the non-labeled reagent previously employed.

In some embodiments, A is a radioactive isotope, such as a radioactive isotope of a metal, coordinated to a chelating group. In some embodiments, the chelating group of the formula

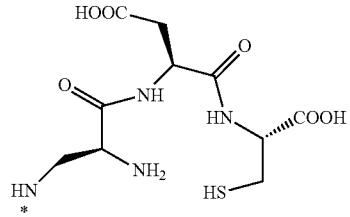 [SMILES: NC[C@H](N)C(=O)N[C@@H](CC(=O)O)C(=O)N[C@@H](CS)C(=O)O]

wherein * represents a covalent bond to the rest of the conjugate.

In some embodiments, the chelating group comprises a radioactive metal isotope selected from the group consisting of an isotope of technetium, rhenium, gallium, gadolinium, indium and copper coordinated thereto. In some embodiments, the chelating group comprises a radioactive metal isotope selected from the group consisting of $^{111}$In, $^{99m}$Tc, $^{64}$Cu, $^{67}$Cu, $^{67}$Ga and $^{68}$Ga coordinated thereto.

In some embodiments, the present disclosure provides methods for imaging a population of cell or tissue, either in vitro or in vivo. It will be appreciated that such in vitro methods may be carried out by any method known in the art. In some embodiments, in vitro imaging methods described herein may include (a) contacting a population of cells with a conjugate in accordance with the present teachings that is suitable for imaging to provide the conjugate bound to cells expressing a LHRH-R protein, and (b) visualizing the conjugate bound to cells by irradiation with light. It will be appreciated that visualizing the conjugate bound to cells by irradiation with light may include irradiation at an excitation wavelength and detection at an emission wavelength. Thus, in some embodiments, in vitro imaging methods described herein may include (a) contacting a population of cells with a conjugate in accordance with the present teachings that is suitable for imaging to provide the conjugate bound to cells expressing a LHRH-R protein, (b) irradiating the conjugate bound to cells expressing a LHRH-R protein with an excitation wavelength light, and (c) detecting light emitted from the cancer cells at an emission wavelength.

In some embodiments, tissues, such as cancerous tumors, may be imaged according to the methods described herein. For example, in some embodiments, in vivo imaging methods in accordance with the present teachings may include (a) administering to the patient a conjugate in accordance with the present teachings that is suitable for imaging; or a pharmaceutically acceptable salt thereof, to provide the conjugate bound to cells expressing a LHRH-R protein; and (b) visualizing the conjugate bound to cells expressing a LHRH-R protein by irradiation with light. It will be appreciated that visualizing the conjugate bound to cells by irradiation with light may include irradiation at an excitation wavelength and detection at an emission wavelength. Thus, in some embodiments, in vivo imaging methods described herein may include (a) administering to the patient a conjugate as described herein that is suitable for imaging; or a pharmaceutically acceptable salt thereof, to provide the conjugate bound to cells expressing a LHRH-R protein; (b) irradiating the conjugate bound to cells expressing a LHRH-R protein with an excitation wavelength light; and (c) detecting light emitted from the cancer cells at an emission wavelength. It will be appreciated that visualizing the conjugate bound to cells by irradiation with light may be carried out using any known imaging techniques (diagnostic or otherwise) or instrumentation known in the art.

In some embodiments, a conjugate in accordance with the present teachings includes a therapeutic agent which, in some embodiments, is therapeutically effective against cancer cells and/or cancer-associated fibroblast (CAFs). The therapeutic agent used in accordance with the present teachings may be any molecule capable of modulating or otherwise modifying cell function, including pharmaceutically active compounds (e.g., a therapeutic agent), or any molecule capable of providing a measurable signal for imaging or visualized cells or tissues (e.g., an imaging agent).

Suitable molecules that may be useful as therapeutic agents include but are not limited to peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; anti-Parkinson agents; expectorants; cough suppressants; mucolytics; and mineral and nutritional additives.

In some embodiments, the therapeutic agent may be a tubulysin. Natural tubulysins are generally linear tetrapeptides consisting of N-methyl pipecolic acid (Mep), isoleucine (Ile), an unnatural aminoacid called tubuvaline (Tuv), and either an unnatural aminoacid called tubutyrosine (Tut, an analog of tyrosine) or an unnatural aminoacid called tubuphenylalanine (Tup, an analog of phenylalanine).

In some embodiments, the therapeutic agent is a tetrapeptide of the formula

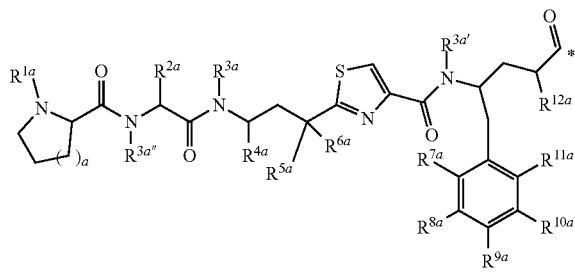

wherein $R^{1a}$, $R^{3a}$, $R^{3a'}$ and $R^{3a''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{13a}$, —OC(O)$R^{13a}$, —OC(O)NR$^{13a}$R$^{13a'}$, —OS(O)R$^{13a}$, —OS(O)$_2$R$^{13a}$, —SR$^{13a}$, —SC(O)R$^{13a}$, —S(O)R$^{13a}$, —S(O)$_2$R$^{13a}$, —S(O)$_2$OR$^{13a}$, —S(O)NR$^{13a}$R$^{13a'}$, —S(O)$_2$NR$^{13a}$R$^{13a'}$, —OS(O)NR$^{13a}$R$^{13a'}$, —OS(O)$_2$NR$^{13a}$R$^{13a'}$, —NR$^{13a}$R$^{13a'}$, —NR$^{13a}$C(O)R$^{14a}$, —NR$^{13a}$C(O)OR$^{14a}$, —NR$^{13a}$C(O)NR$^{14a}$R$^{14a'}$, —NR$^{13a}$S(O)R$^{14a}$, —NR$^{13a}$S(O)$_2$R$^{14a}$, —NR$^{13a}$S(O)NR$^{13a}$R$^{14a'}$, —NR$^{13a}$S(O)$_2$NR$^{14a}$R$^{14a'}$, —P(O)(OR$^{13}$a)$_2$, —C(O)R$^{13a}$, —C(O)OR$^{13a}$ or —C(O)NR$^{13a}$R$^{13a'}$;

$R^{2a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ and $R^{6a}$ are each independently selected from the group consisting of H, halogen, $C_1$-$C_6$ alkyl, $C_2$-$C_6$ alkenyl, $C_2$-$C_6$ alkynyl, —OR$^{15a}$, —SR$^{15a}$ and —NR$^{15a}$R$^{15a'}$, wherein each hydrogen atom in $C_1$-$C_6$ alkyl, $C_2$-$C_6$ alkenyl and $C_2$-$C_6$ alkynyl is independently optionally substituted by halogen, —OR$^{16a}$, —SR$^{16a}$, —NR$^{16a}$R$^{16a'}$, —C(O)R$^{16a}$, —C(O)OR$^{16a}$ or —C(O)NR$^{16a}$R$^{16a'}$; or $R^{5a}$ and $R^{6a}$ taken together with the carbon atom to which they are attached form a —C(O)—;

each $R^{7a}$, $R^{8a}$, $R^{9a}$, $R^{10a}$ and $R^{11a}$ is independently selected from the group consisting of H, halogen, $C_1$-$C_6$ alkyl, $C_2$-$C_6$ alkenyl, $C_2$-$C_6$ alkynyl, —CN, —NO$_2$, —NCO, —OR$^{17a}$, —SR$^{17a}$, —S(O)$_2$OR$^{17a}$, —NR$^{17a}$R$^{17a'}$, —P(O)(OR$^{17}$a)$_2$, —C(O)R$^{17a}$, —C(O)OR$^{17a}$ and —C(O)NR$^{17a}$R$^{17a'}$ wherein each hydrogen atom in $C_1$-$C_6$ alkyl, $C_2$-$C_6$ alkenyl and $C_2$-$C_6$ alkynyl is independently optionally substituted by halogen, —OR$^{18a}$, —SR$^{18a}$, —NR$^{18a}$R$^{18a'}$, —C(O)R$^{18a}$, —C(O)OR$^{18a}$ or —C(O)NR$^{18a}$R$^{18a'}$;

each $R^{13a}$, $R^{13a'}$, $R^{14a}$, $R^{14a'}$, $R^{15a}$, $R^{15a'}$, $R^{16a}$, $R^{16a'}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —NH$_2$ or —CO$_2$H;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —C(O)R$^{19a}$, —P(O)(OR$^{19a}$)$_2$, and —S(O)$_2$OR$^{19a}$, each $R^{19}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

a is 1, 2 or 3; and

* represents a covalent bond to the rest of the conjugate.

In some embodiments, the therapeutic agent is of the formula

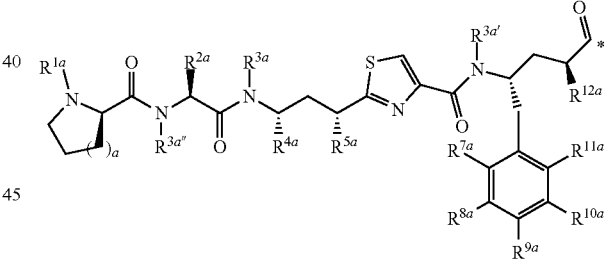

wherein $R^{1a}$, $R^{2a}$, $R^{3a}$, $R^{3a'}$, $R^{3a''}$, $R^{4a}$, $R^{5a}$, $R^{7a}$, $R^{8a}$, $R^{9a}$, $R^{10a}$, $R^{11a}$ and $R^{12a}$ are as described herein, and * represents a covalent bond to the rest of the conjugate.

In another embodiment, the therapeutic agent may be a naturally occurring tubulysin, or analog or derivative thereof, of the following general formula

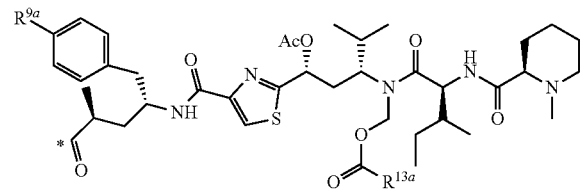

wherein $R^{9a}$ and $R^{13a}$ are as described herein, and * represents a covalent bond to the rest of the conjugate.

Conjugates of each of the foregoing tubulysins are described herein.

In some embodiments, the therapeutic agent may be a naturally occurring tubulysin of the following general formula

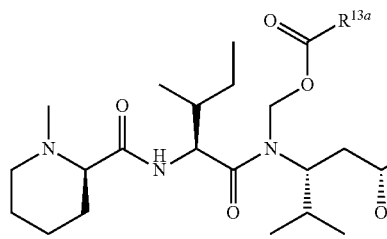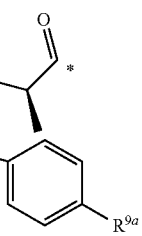

| Factor | $R^{13a}$ | $R^{9a}$ |
|---|---|---|
| A | $(CH_3)_2CHCH_2$ | OH |
| B | $CH_3(CH_2)_2$ | OH |
| C | $CH_3CH_2$ | OH |
| D | $(CH_3)_2CHCH_2$ | H |
| E | $CH_3(CH_2)_2$ | H |
| F | $CH_2CH_3$ | H |
| G | $(CH_3)_2C\!\!=\!\!CH$ | OH |
| H | $CH_3$ | H |
| I | $CH_3$ | OH | and * represents a covalent bond to the rest of the conjugate

In some embodiments, the methods in accordance with the present teachings may be used for both human clinical medicine and veterinary applications as a "subject". Thus, a "subject" may be administered the conjugates in accordance with the present teachings, and may be human ("patient") or, in the case of veterinary applications, may be a laboratory, agricultural, domestic, or wild animal. In some embodiments, the subject may be a human patient, a laboratory animal such as a rodent (e.g., mice, rats, hamsters, etc.), a rabbit, a monkey, a chimpanzee, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

In some embodiments, the cancers described herein may be a cancer cell population that is tumorigenic, including benign tumors and malignant tumors, or the cancer may be non-tumorigenic. The cancer may arise spontaneously or by such processes as mutations present in the germline of the patient or somatic mutations, or the cancer may be chemically-, virally-, or radiation-induced. Cancers applicable to the present teachings include but are not limited to a carcinoma, a sarcoma, a lymphoma, a melanoma, a mesothelioma, a nasopharyngeal carcinoma, a leukemia, an adenocarcinoma, and a myeloma.

In some embodiments, the cancers may be lung cancer, bone cancer, pancreatic cancer, skin cancer, cancer of the head, cancer of the neck, cutaneous melanoma, intraocular melanoma uterine cancer, ovarian cancer, endometrial cancer, leiomyosarcoma, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, small cell lung cancer, cancer of the adrenal gland, sarcoma of soft tissue, cancer of the urethra, cancer of the penis, prostate cancer, chronic leukemia, acute leukemia, lymphocytic lymphomas, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, cholangiocarcinoma, Hurthle cell thyroid cancer or adenocarcinoma of the gastroesophageal junction.

In some embodiments of the methods described herein, pharmaceutically acceptable salts of conjugates in accordance with the present teachings are provided. Pharmaceutically acceptable salts of conjugates in accordance with the present teachings include acid addition and base salts thereof.

Suitable acid addition salts are formed from acids which form non-toxic salts. Illustrative examples include but are not limited to the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts of the conjugates described herein are formed from bases which form non-toxic salts. Illustrative examples include but are not limited to the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In some embodiments, conjugates in accordance with the present teachings may be administered as a formulation in association with one or more pharmaceutically acceptable carriers. The carriers may be excipients. The choice of carrier may depend on factors such as the particular mode of administration, the effect of the carrier on solubility and stability, and the nature of the dosage form. Pharmaceutical compositions suitable for the delivery of conjugates as described herein and methods for their preparation will be readily apparent to those skilled in the art. Such compositions and methods for their preparation may be found, for example, in Remington: The Science & Practice of Pharmacy, 21th Edition (Lippincott Williams & Wilkins, 2005).

In some embodiments, a pharmaceutically acceptable carrier includes any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions and sterile powders for the extemporaneous preparation of sterile injectable solutions or dispersions. Supplementary active compounds may also be incorporated into compositions of the invention.

In some embodiments, liquid formulations may include suspensions and solutions. Such formulations may comprise a carrier, for example, water, ethanol, polyethylene glycol, propylene glycol, methylcellulose or a suitable oil, and one or more emulsifying agents and/or suspending agents. Liquid formulations may also be prepared by the reconstitution of a solid.

In some embodiments, an aqueous suspension may contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ascorbic acid, ethyl, n-propyl, or p-hydroxybenzoate; or one or more coloring agents.

In some embodiments, dispersible powders and granules suitable for preparation of an aqueous suspension by the addition of water provide the active ingredient in admixture with a dispersing or wetting agent, suspending agent and one or more preservatives. Additional excipients, for example, coloring agents, may also be present.

Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate.

In some embodiments, isotonic agents, for example, sugars, polyalcohols such as mannitol, sorbitol, or sodium chloride may be included in the composition. Prolonged absorption of injectable compositions may be brought about by including in the composition an agent which delays absorption, for example, monostearate salts and gelatin.

Illustrative formats for oral administration include but are not limited to tablets, capsules, elixirs, syrups, and the like.

Depending upon the cancer type as described herein, the route of administration and/or whether the conjugates are administered locally or systemically, a wide range of permissible dosages are contemplated herein, including doses falling in the range from about 1 µg/kg to about 1 g/kg. The dosages may be single or divided, and may administered according to a wide variety of protocols, including q.d., b.i.d., t.i.d., or even every other day, biweekly (b.i.w.), once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In some embodiments, a conjugate in accordance with the present teachings may be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. Suitable means for parenteral administration include needle (including microneedle) injectors, needle-free injectors and infusion techniques.

In some embodiments, parenteral formulations are typically aqueous solutions which may contain carriers or excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water. In other embodiments, any of the liquid formulations described herein may be adapted for parenteral administration of the conjugates described herein. The preparation of parenteral formulations under sterile conditions, for example, by lyophilization under sterile conditions, may readily be accomplished using standard pharmaceutical techniques well known to those skilled in the art. In some embodiments, the solubility of a conjugate as described herein used in the preparation of a parenteral formulation may be increased by the use of appropriate formulation techniques, such as the incorporation of solubility-enhancing agents.

In some embodiments, formulations for parenteral administration may be formulated for immediate and/or modified release. In some embodiments, active agents in accordance with the present teachings (i.e., the conjugates described herein) may be administered in a time release formulation, for example in a composition which includes a slow release polymer. The active agents may be prepared with carriers that will protect the conjugate against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PGLA). Methods for the preparation of such formulations are generally known to those skilled in the art. In other embodiments, the conjugates in accordance with the present teachings or compositions comprising the conjugates may be continuously administered, where appropriate.

In some embodiments, a kit is provided. If a combination of active conjugates as described herein is to be administered, two or more pharmaceutical compositions may be combined in the form of a kit suitable for sequential administration or co-administration of the compositions. Such a kit may include two or more separate pharmaceutical compositions, at least one of which contains a conjugate in accordance with the present teachings, and means for separately retaining the compositions, such as a container, divided bottle, or divided foil packet. In some embodiments, compositions comprising one or more conjugates as described herein, in containers having labels that provide instructions for use of the conjugates as described herein for patient selection and/or treatment are provided.

As used herein, the term "kit" refers to an assembly of materials that are used in performing a method in accordance with the present teachings. The components of the kit may be provided in packaged combination in the same or in separate containers, depending on their cross-reactivities and stabilities, and in liquid or in solid form. The amounts and proportions of components provided in the kit may be selected so as to provide optimum results for a particular application. While in some embodiments, the components to be administered (e.g., to a patient) may be provided in separate physical forms (e.g., a kit containing one or more compositions and one or more fluids), it is to be understood that in other embodiments, all of the components that are to be introduced to the patient may be provided together in one common physical form (e.g., one composition or one fluid).

The components included in kits in accordance with the present teachings may be supplied in all manner of containers such that the activities of the different components are substantially preserved, while the components themselves are not substantially adsorbed or altered by the materials of the container. Suitable containers include but are not limited to ampoules, bottles, test tubes, vials, flasks, syringes, bags and envelopes (e.g., foil-lined), and the like. The containers may be formed of any suitable material including but not limited to glass, organic polymers (e.g., polycarbonate, polystyrene, polyethylene, polypropylene, etc.), ceramic, metal (e.g., aluminum), metal alloys (e.g., steel), cork, and the like. In addition, the containers may contain one or more access ports (e.g., for access via a needle), such as may be provided by a septum. Preferred materials for septa include rubber and polymers including but not limited to, for example, polytetrafluoroethylene of the type sold under the trade name TEFLON by DuPont (Wilmington, Del.). In addition, the containers may contain two or more compartments separated by partitions or membranes that can be removed to allow mixing of the components.

Kits in accordance with the present teachings may also be supplied with other items known in the art and/or which may be desirable from a commercial and user standpoint, including but not limited to instructions for adding the components of the kit to a heat exchange system.

Instructional materials provided with kits in accordance with the present invention may be printed (e.g., on paper) and/or supplied in an electronic-readable medium (e.g., floppy disc, CD-ROM, DVD-ROM, zip disc, videotape, audio tape, etc.). Alternatively, instructions may be provided by directing a user to an Internet web site (e.g., specified by the manufacturer or distributor of the kit) and/or via electronic mail, text message, social media, and/or the like, and combinations thereof.

In some embodiments, sterile injectable solutions may be prepared by incorporating the active agent in the required amount in an appropriate solvent with one or a combination of ingredients described above, as required, followed by filtered sterilization. Typically, dispersions are prepared by incorporating the conjugate into a sterile vehicle which contains a dispersion medium and any additional ingredients of those described above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof, or the ingredients may be sterile-filtered together.

The composition may be formulated as a solution, microemulsion, liposome, or other ordered structure suitable to high drug concentration. The carrier may be a solvent or dispersion medium containing, for example, water, ethanol, polyol (e.g., glycerol, propylene glycol, and liquid polyethylene glycol, and the like), and suitable mixtures thereof. In some embodiments, the proper fluidity may be maintained, for example, by the use of a coating such as lecithin, by the maintenance of the required particle size in the case of dispersion and by the use of surfactants.

Any effective regimen for administering the conjugates described herein may be used. For example, conjugates described herein may be administered as single doses, or the doses may be divided and administered as a multiple-dose daily regimen. Further, a staggered regimen, for example, one to five days per week may be used as an alternative to daily treatment, and for the purpose of the methods described herein, such intermittent or staggered daily regimen is considered to be equivalent to every day treatment and is contemplated. In some embodiments, the patient is treated with multiple injections of a conjugate in accordance with the present teachings to treat the cancer. In some embodiments, the patient is injected multiple times (e.g., about 2 up to about 50 times) with a conjugate in accordance with the present teachings, for example, at 12-72 hour intervals or at 48-72 hour intervals. Additional injections of a conjugate in accordance with the present teachings may be administered to the patient at an interval of days or months after the initial injections(s) and the additional injections may prevent recurrence of the cancer.

Any suitable course of therapy with the conjugates in accordance with the present teachings may be used. In some embodiments, individual doses and dosage regimens are selected to provide a total dose administered during a month of about 15 mg. In some examples, a conjugate in accordance with the present teachings is administered in a single daily dose administered five days a week, in weeks 1, 2, and 3 of each 4 week cycle, with no dose administered in week 4. In an alternative example, a conjugate in accordance with the present teachings is administered in a single daily dose administered three days a week, of weeks 1, and 3 of each 4 week cycle, with no dose administered in weeks 2 and 4. In an alternative example, a conjugate in accordance with the present teachings is administered biweekly on weeks 1 and 2 (i.e., on days 1, 4, 8, 11, of a 3-week cycle). In an alternative example, a conjugate described herein is administered and once weekly on weeks 1 and 2 (i.e., days 1 and 8 of a 3-week cycle).

The unitary daily dosage of the conjugates in accordance with the present teachings may vary significantly depending on the patient condition, the cancer being treated, the route of administration of the conjugates described herein and tissue distribution, and the possibility of co-usage of other therapeutic treatments, such as radiation therapy or additional drugs in combination therapies. The effective amount to be administered to a patient is based on body surface area, mass, and physician assessment of patient condition. Therapeutically effective doses (also referred to herein as "therapeutically effective amounts") may range, for example, from about 0.5 mg/m$^2$ to about 20.0 mg/m$^2$.

The conjugates in accordance with the present teachings may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The conjugates in accordance with the present teachings may be capable of existing as geometric isomers. Accordingly, it is to be understood that the present invention includes pure geometric isomers or mixtures of geometric isomers.

It is appreciated that the conjugates in accordance with the present teachings may exist in unsolvated forms as well as solvated forms, including hydrated forms. In general, the solvated forms are equivalent to unsolvated forms and are encompassed within the scope of the present invention. The conjugates described herein may exist in multiple crystalline or amorphous forms. In general, all physical forms are equivalent for the uses contemplated by the present invention and are intended to be within the scope of the present invention.

In some embodiments, compositions and/or dosage forms for administration of a conjugate in accordance with the present teachings are prepared from a conjugate with a purity of at least about 90%, or about 95%, or about 96%, or about 97%, or about 98%, or about 99%, or about 99.5%. In other embodiments, compositions and or dosage forms for administration of a conjugate in accordance with the present teachings are prepared from a conjugate with a purity of at least 90%, or at least 95%, or at least 96%, or at least 97%, or at least 98%, or at least 99%, or at least 99.5%.

In some embodiments the drug may be cisplatin, disorazol, an ERK inhibitors, a PI3K/ERK inhibitor, or gemcitabine.

Small molecule targeting ligands may possess several advantages when compared to peptides and antibodies including but not limited to: i) stability over a broad range of pH and temperature which makes them more feasible for site-specific radiolabeling, ii) high tumor penetration and favorable pharmacokinetics, iii) rapid clearance, and iv) non-immunogenicity. The use of a non-peptidic small molecule antagonist for LHRH-R to develop LHRH-R targeted near-infrared dye conjugates can overcome drawbacks of using a peptide targeting ligands such as non-specific uptake by the scavenger receptors in the liver and kidney, instability of the peptides in circulation, etc.

The following examples and representative procedures illustrate features in accordance with the present teachings, and are provided solely by way of illustration. They are not intended to limit the scope of the appended claims or their equivalents.

Materials. benzotriazol-1-yl-oxytripyrrolidinophosphonium hexafluorophosphate (PyBop), N,N-Dimethylmethanamide (DMF), -(1H-7-Azabenzotriazole-1-yl)-1,1,3,3-tetramethyl uronium hexafluorophosphate methanaminium (HATU), N-ethyl-N-isopropylpropan-2-amine (DIPEA), isopropyl alcohol (IPA,) dichloromethane (DCM) and trifluoroacetic acid (TFA), 1,2-ethanedithiol, triisopropylsilane (TIPS), piperidine, dmithelysulfoxide (DMSO) and all other chemical reagents were purchased from Sigma-Aldrich. Cell culture reagents such as rosewell park memorial institute medium 1640 (RPMI 1640) and fetalbovine serum (FBS) was purchased from GIBCO (Grand Island, N.Y.) whereas 1% penicillin-streptomycin, 2 Mm glutamine were purchased from Life Technologies. $^{99m}$Tc-Sodium pertechnetate was supplied by Syncor. H-Cys(Trt)-2-Cl-Trt resin and protected amino acids were purchased from Chem-Impex Intl. (Chicago, Ill.). Tubulysin B hydrazide and its activated derivative was a kind gift from Endocyte Inc. (West Lafayette, Ind.). Glutamine, penicillin-streptomycin and trypsin were procured from BD Biosciences (San Jose, Calif.).

COMPOUND EXAMPLES

Compound Example 1. JL-L1-S0456, JL-L2-S0456, JL-L3-S0456

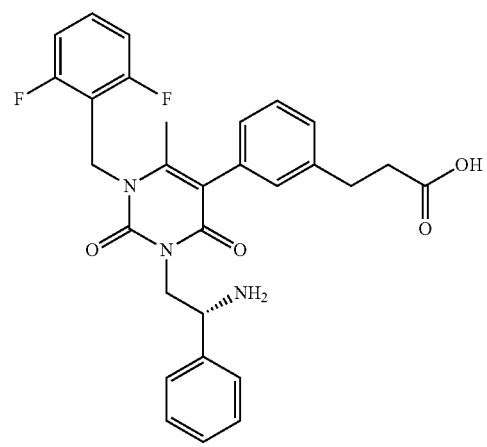

JL

51
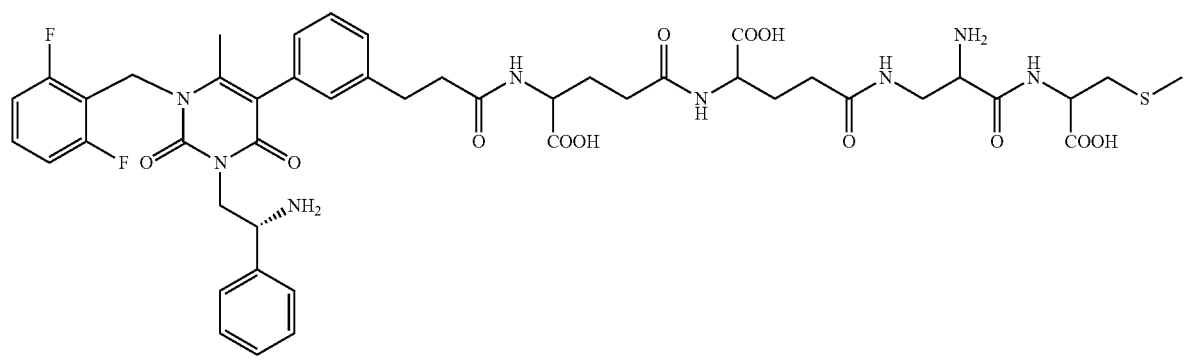
52
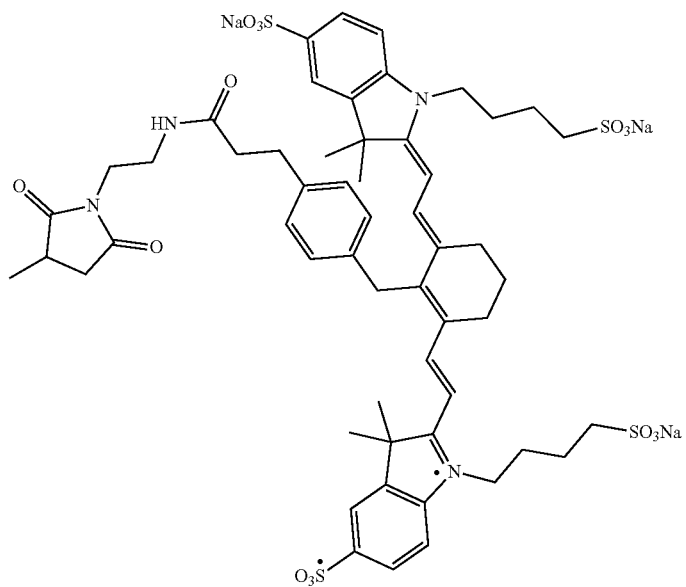
JL-L1-S0456
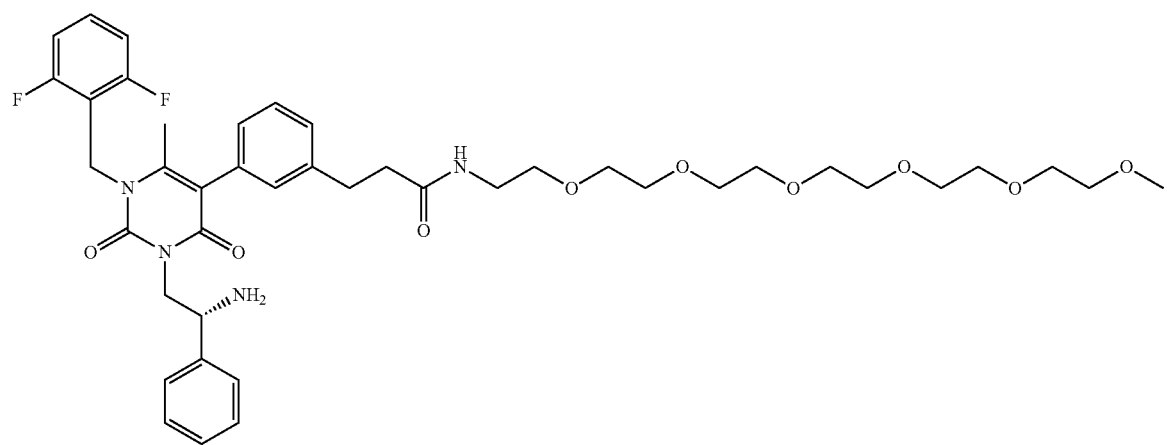

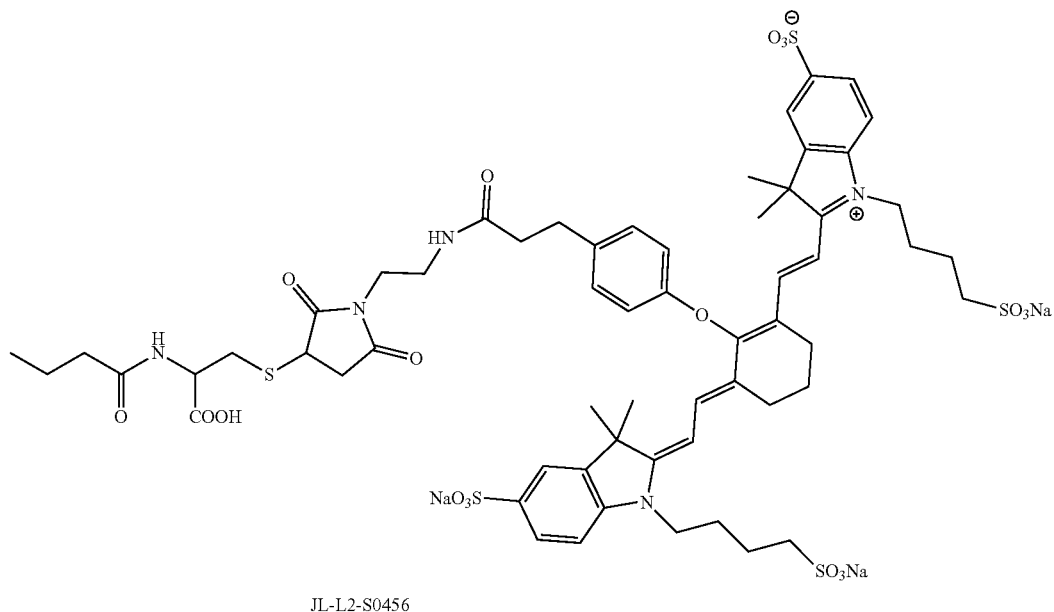
JL-L2-S0456
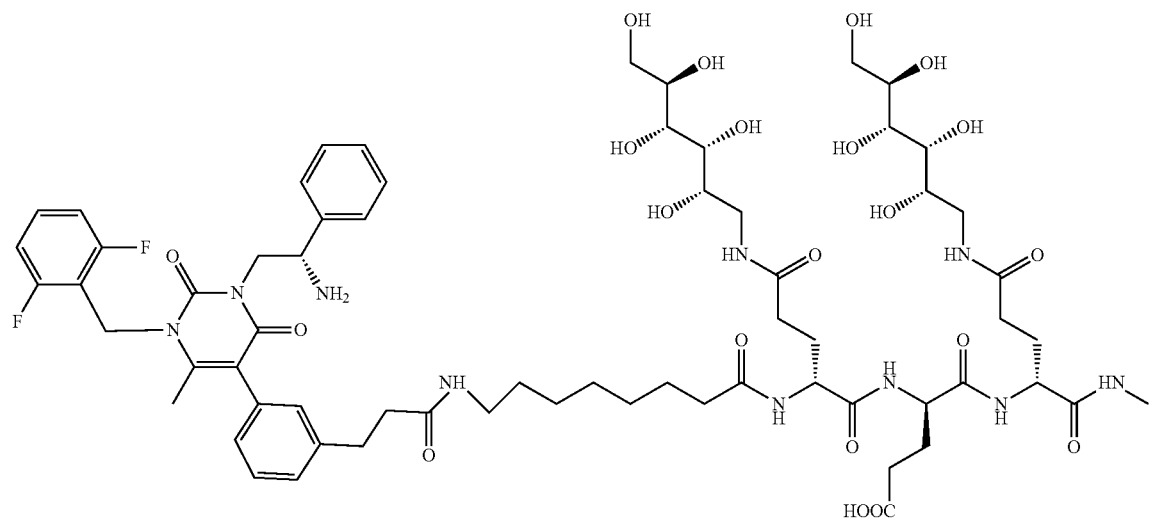

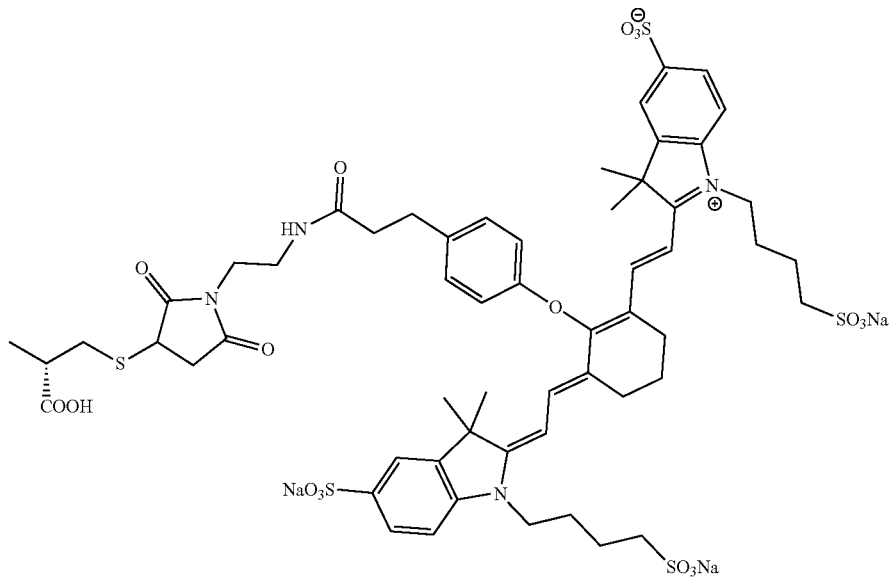
JL-L3-S0456
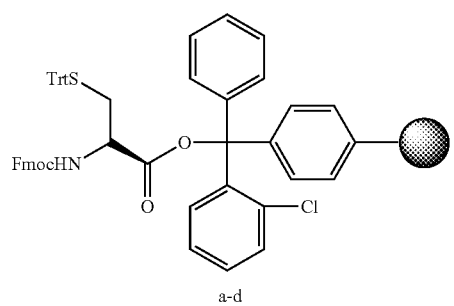
a-d

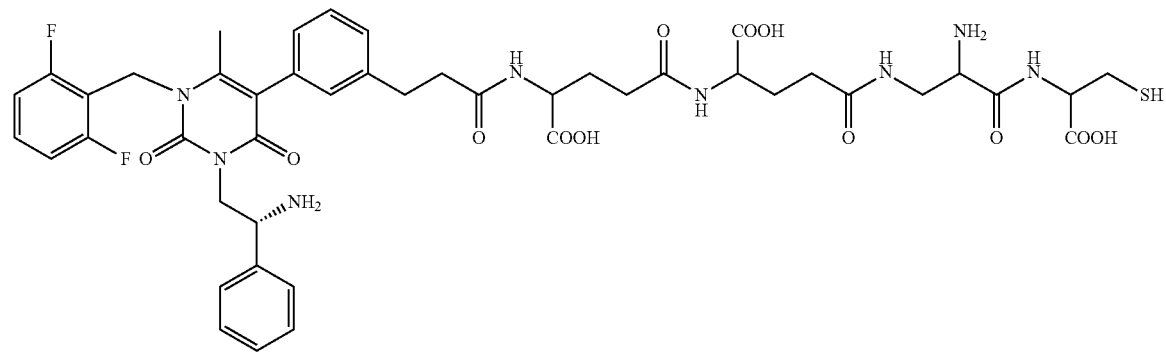
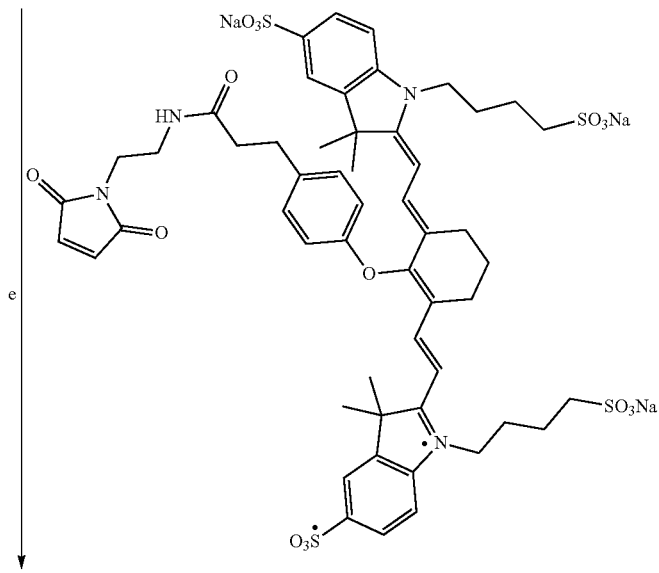
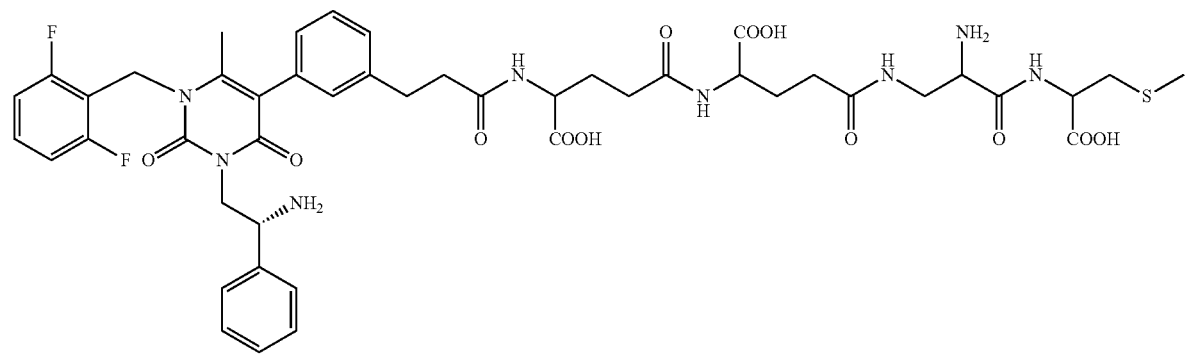

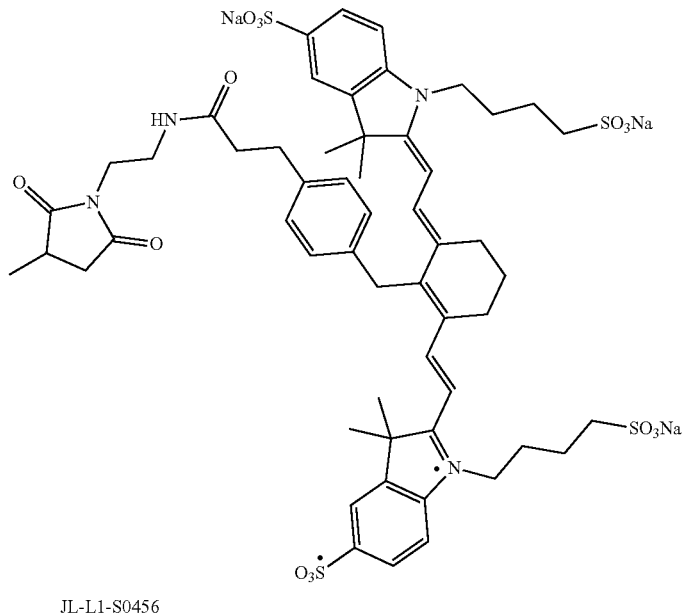

JL-L1-S0456

Scheme 1. Synthesis of JR-L1-S0456, Reagents and conditions: (a) (i) 20% piperidine/DMF, rt, (ii) Fmoc-diaminopropionic (DAP) acid, PyBop, DMF, DIPEA, (b) (i) 20% piperidine/DMF, rt, 10 min (ii) N-Fmoc-L-glutamic acid alpha-tert-butyl ester, PyBop, DMF, DIPEA, (c) (i) 20% piperidine/DMF, rt, 10 min (ii) N-Fmoc-L-glutamic acid alpha-tert-butyl ester, PyBop, DMF, DIPEA, (d) (i) 20% piperidine/DMF, rt, 10 min (ii) JL, PyBop, DMF, DIPEA, (iii) TFA/H$_2$O/TIPS/EDT (92.5:2.5:2.5:2.5), 1 h, (e) JL-L1, S0456 maleimide, anhydrous DMSO, DIPEA, rt.

Synthesis of JL-L1: LHRH-R ligand was synthesized according to the methods described in Tucci, F. C., et al. (2005). Journal of medicinal chemistry, 48(4), 1169-1178 and Struthers, R. S., et al. (2007). Endocrinology, 148(2), 857-867, each of which is incorporated by reference herein. For the simplicity of conjugation, ether group present on the published molecule was modified to have carboxylic acid group. The modified LHRH-R ligand is referred to as JL. As described in Scheme 1, the linker was prepared by the standard solid phase peptide synthesis. JL was then coupled to the linker on the solid phase. The final product was cleaved from the H-Cys(Trt)2-chlorotrityl resin using the standard cocktail solution of TFA:Water:TIPS: Ethanedithiol (95%: 2.5%: 2.5%: 2.5%). Crude JL-L1 was purified by using RP-HPLC [A=2 Mm ammonium acetate buffer (pH 5.0), B=acetonitrile, solvent gradient 0% B to 80% B in 35 min] to yield the requisite product. LRMS-LC/MS (m/z): [M+H]$^+$ calcd for $C_{15}H_{56}F_2N_8O_{13}$, 1027; found 1028.

Figure 1B:
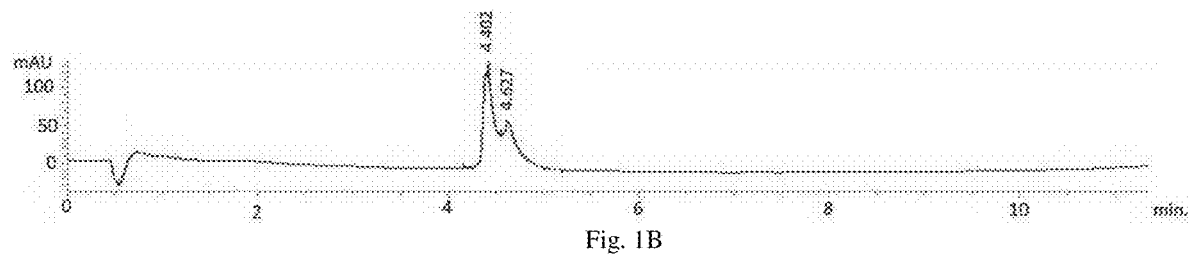
Figure 1C:
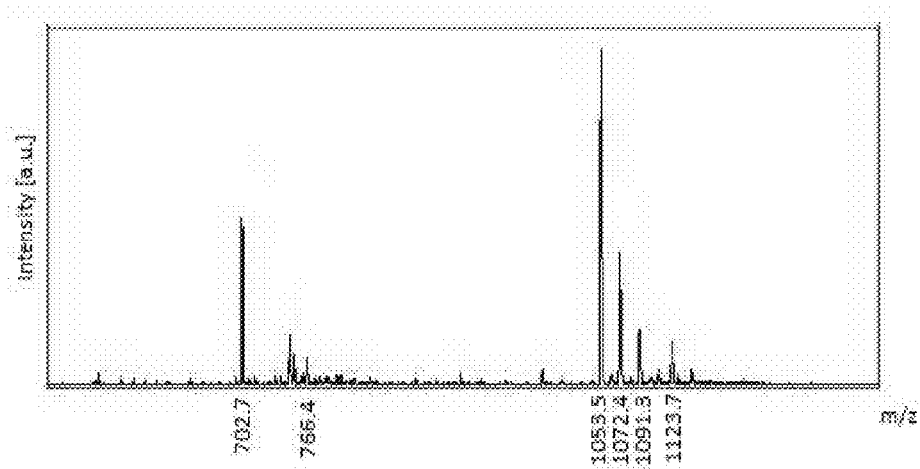
Figure 2A:
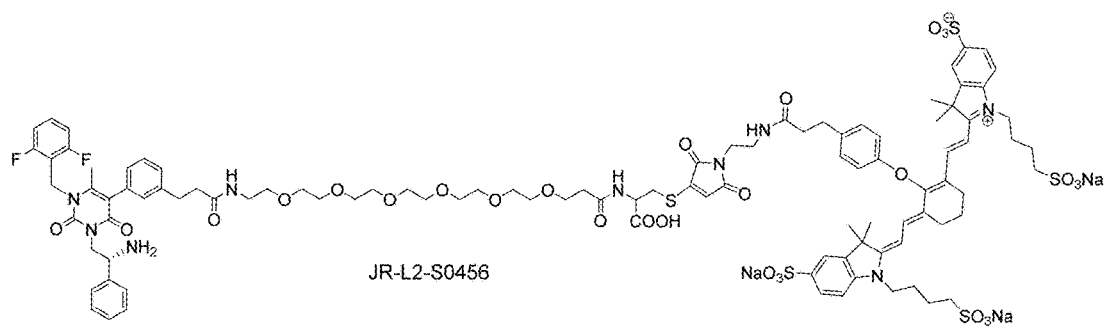
FIGS. 2A-2D show the chemical structure (FIG. 2A) and an LC/MS trace (FIGS. 2B-2D) for JR-L2-S0456.
Figure 2B:
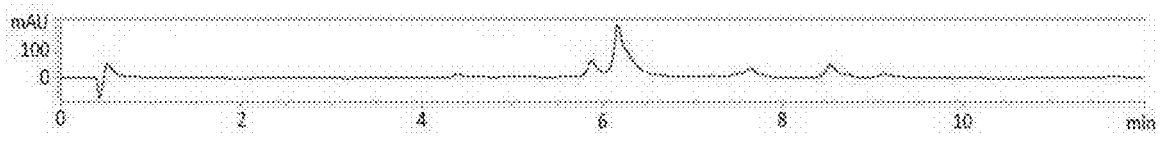
Figure 2C:
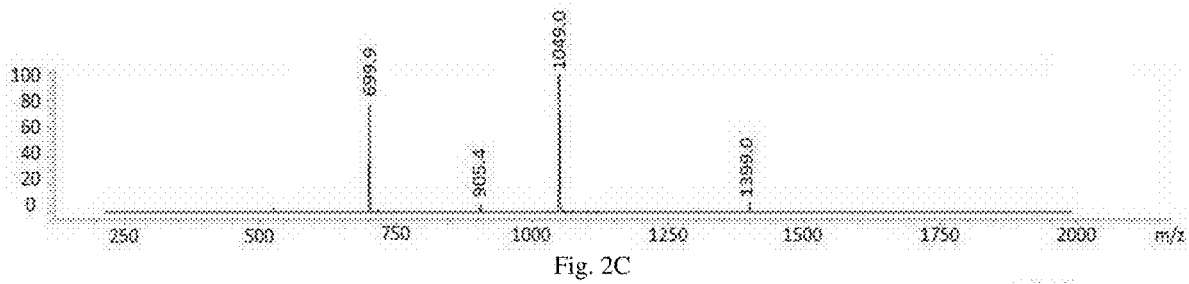
Figure 2D:
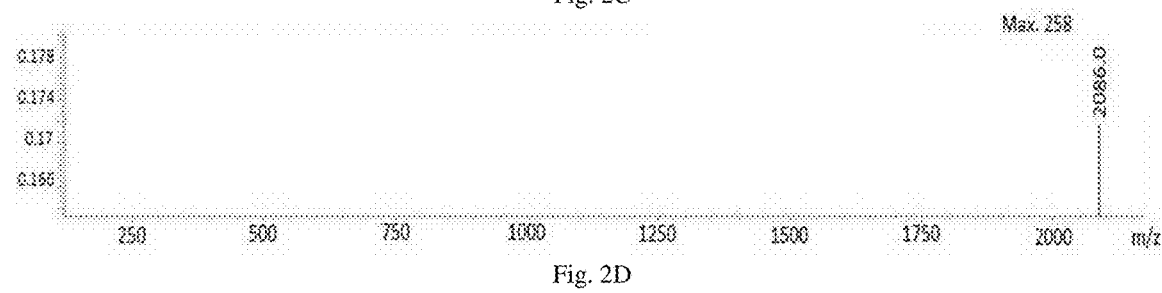
Figure 3A:
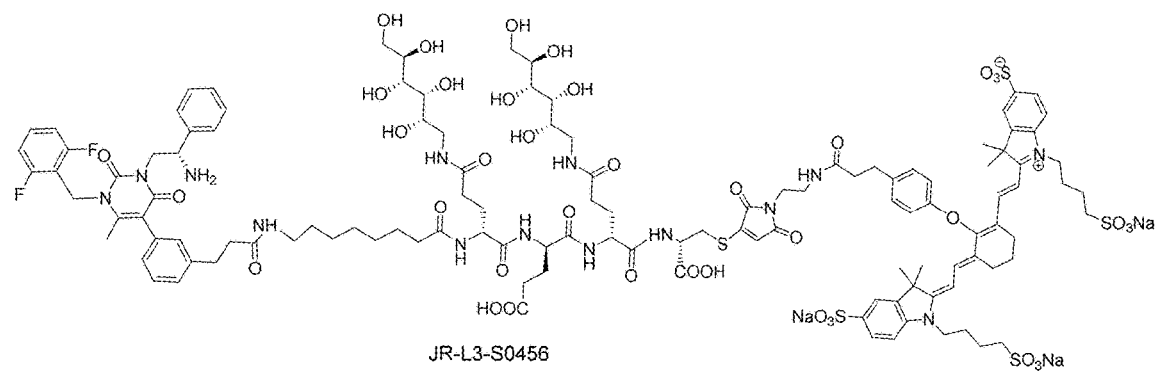
FIGS. 3A-3D show the chemical structure (FIG. 3A) and an LC/MS trace (FIGS. 3B-3D) for JR-L2-S0456.
Figure 3B:
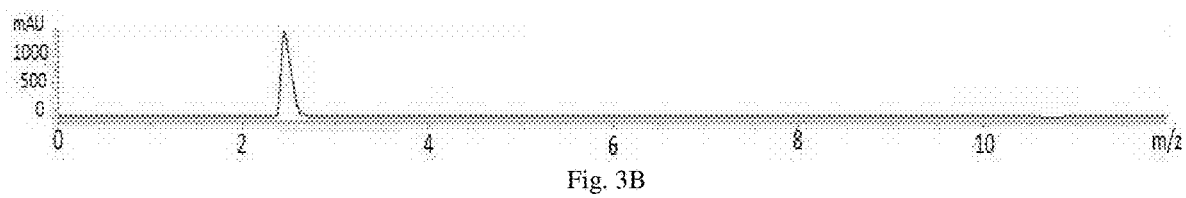
Figure 3C:
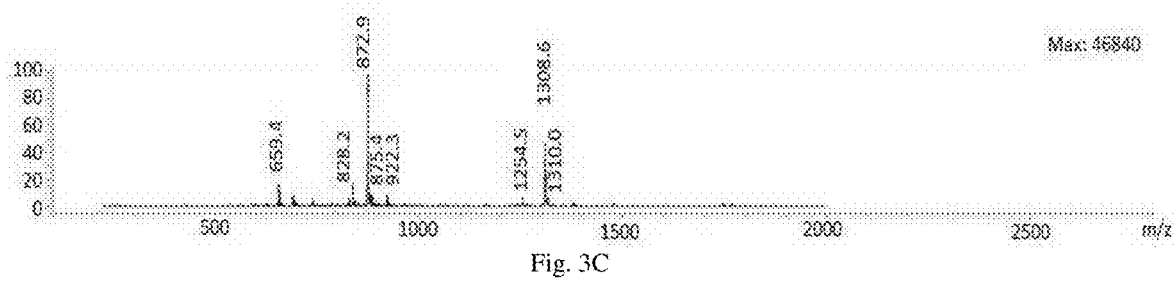
Figure 3D:
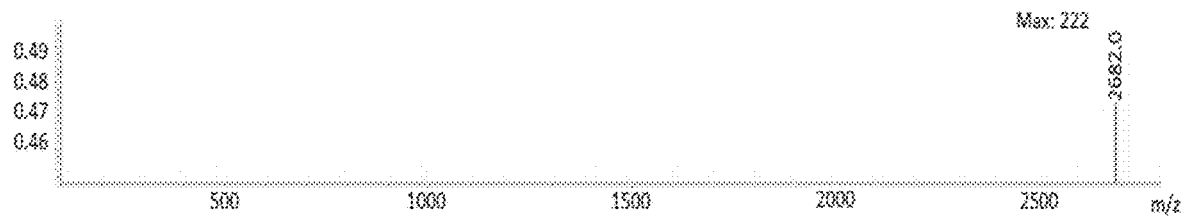

Synthesis of NIR conjugate JL-L1-S0456: S0456 dye containing the maleimide was synthesized as described in the Scheme 1. 1 equivalence of 50456-maleimide and JL-L1 were dissolved in anhydrous DMSO, followed by addition of 5 equivalences of DIPEA. The reaction mixture was stirred under argon atmosphere for 1 h. The completion of the reaction was monitored by using LC-MS. Crude JL-L1-S0456 was purified by using RP-HPLC [A=2 Mm ammonium acetate buffer (pH 7.0), B=acetonitrile, solvent gradient 0% B to 80% B in 35 min] to yield the requisite product. The LCMS characterization of JL-L1-S0456 was as follows. LRMS-LC/MS (m/z): [M+H]$^+$ calcd for $C_{89}H_{99}F_2N_{10}Na_3O_{22}S_3$, 1863; found 1864. LRMS-LC/MS trace of JR-L1-S0456 is shown in FIG. 1.

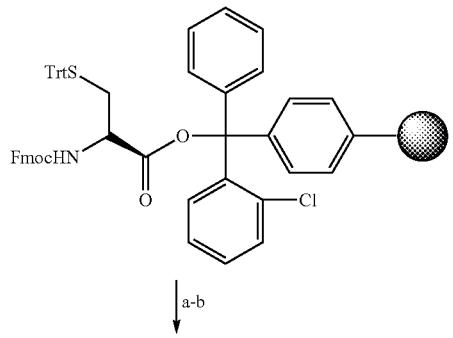

-continued
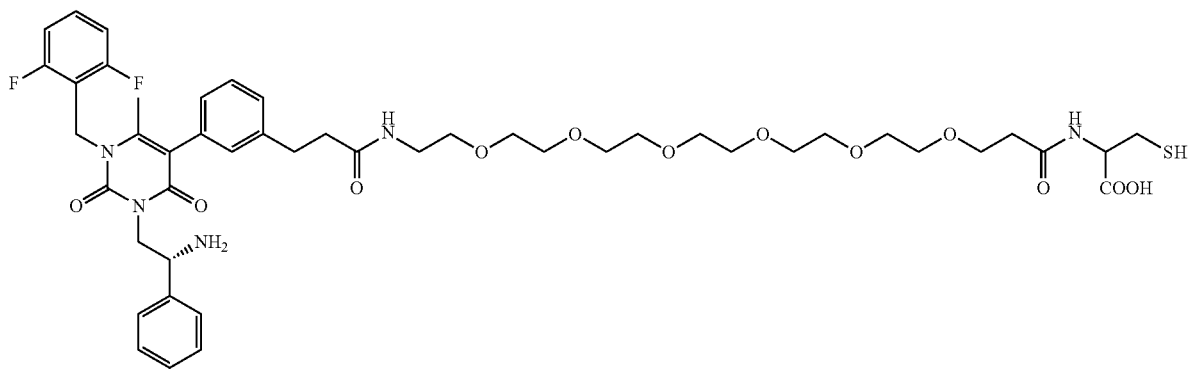
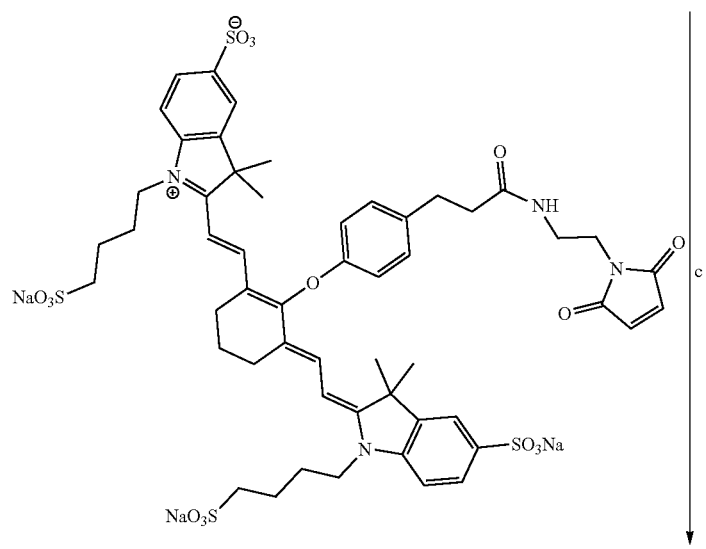
JL-L2
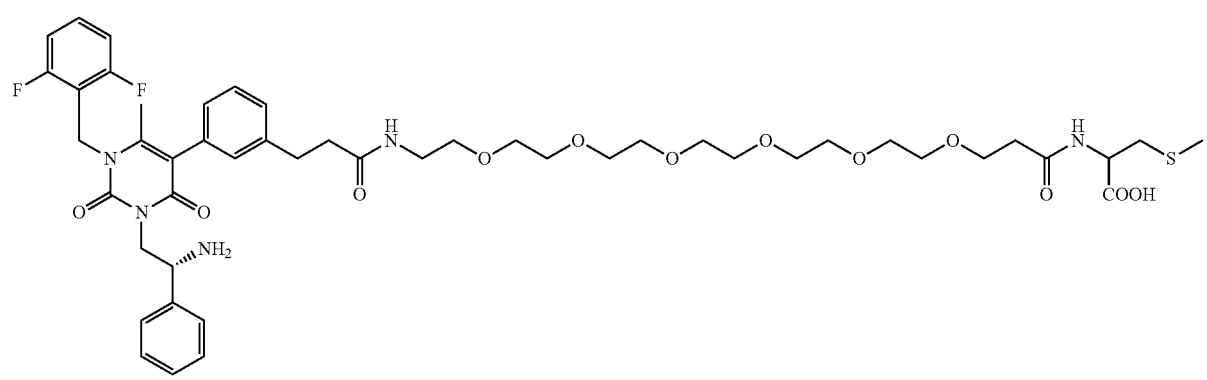

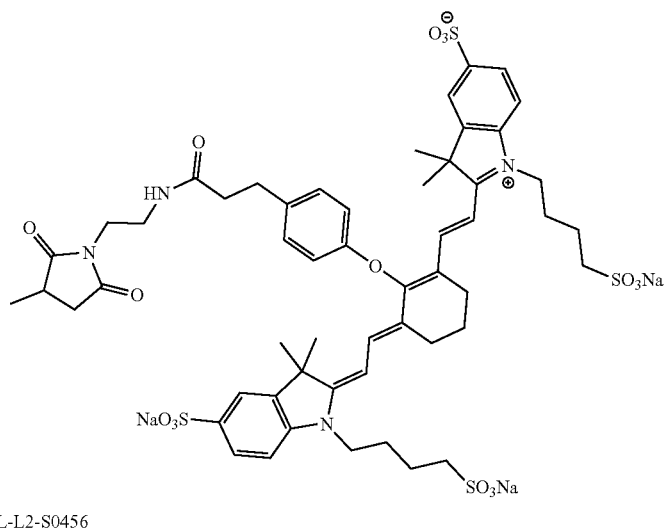

JL-L2-S0456

Scheme 2. Synthesis of JL-L2-50456, Reagents and conditions: (a) (i) 20% piperidine/DMF, rt, (ii) Fmoc-N-amido-dPEG$_6$-acid, PyBop, DMF, DIPEA, (b) (i) 20% piperidine/DMF, rt, 10 min (ii) JL, PyBop, DMF, DIPEA, (iii) TFA/H$_2$O/TIPS/EDT (92.5:2.5:2.5:2.5), 1 h, (c) JL-L2, S0456 maleimide, anhydrous DMSO, DIPEA, rt.

Synthesis of JL-L2: As described in Scheme 2, the linker was prepared by the standard solid phase peptide synthesis. JL was then coupled to the linker on the solid phase. The final product was cleaved from the H-Cys(Trt)2-chlorotrityl resin using the standard cocktail solution of TFA:Water:TIPS:Ethanedithiol (95%: 2.5%: 2.5%: 2.5%). Crude JL-L2 was purified by using RP-HPLC [A=2 Mm ammonium acetate buffer (pH 5.0), B=acetonitrile, solvent gradient 0% B to 80% B in 35 min] to yield the requisite product. LRMS-LC/MS (m/z): [M+H]$^+$ calcd for C$_{47}$H$_{61}$F$_2$N$_5$O$_{12}$S, 958.08; found 959.

Synthesis of NIR conjugate JL-L2-S0456: 50456 dye containing the maleimide was synthesized as described in the scheme 2. 1 equivalence of 50456-maleimide and JL-L2 were dissolved in anhydrous DMSO, followed by addition of 5 equivalences of DIPEA. The reaction mixture was stirred under argon atmosphere for 1 h. The completion of the reaction was monitored by using LC-MS. Crude JL-L2-S0456 was purified by using RP-HPLC [A=2 Mm ammonium acetate buffer (pH 7.0), B=acetonitrile, solvent gradient 0% B to 80% B in 35 min] to yield the requisite product. JL-L3 S0456 were synthesized and purified by the same procedure as JL-L1-S0456. The LCMS characterization of JL-L2-S0456 was as follows. LRMS-LC/MS (m/z): [M+H]$^+$ calcd for C$_{100}$H$_{115}$F$_2$N$_9$Na$_3$O$_{28}$S$_5$, 2161.35; found 2162. LRMS-LC/MS trace of JR-L2-S0456 is shown in FIG. 2.

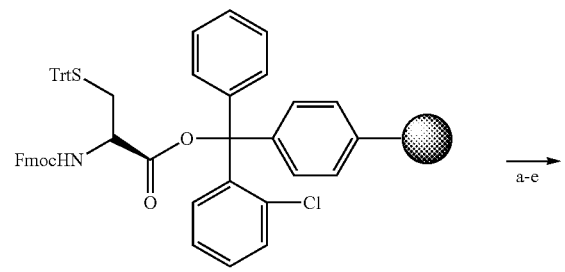

65
66
-continued
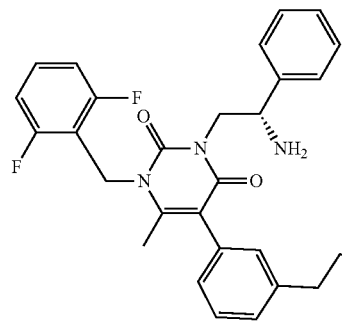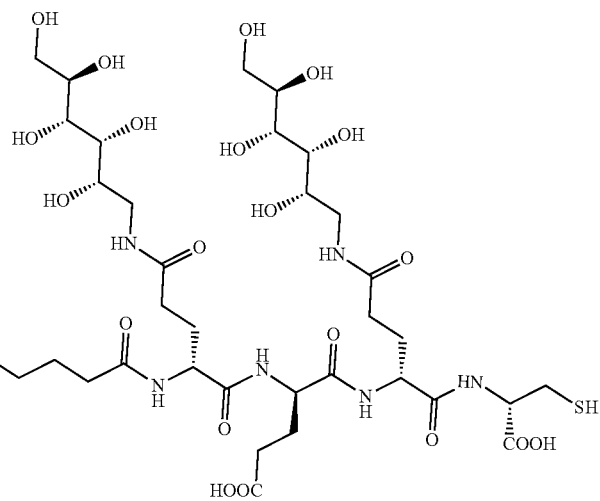
JL-L3
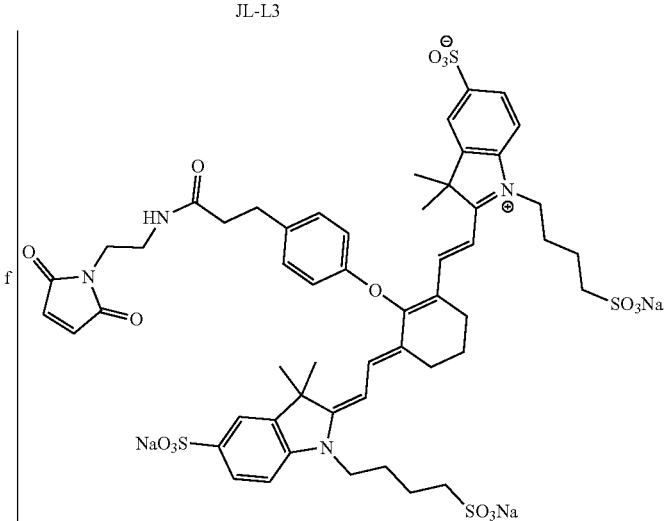
f
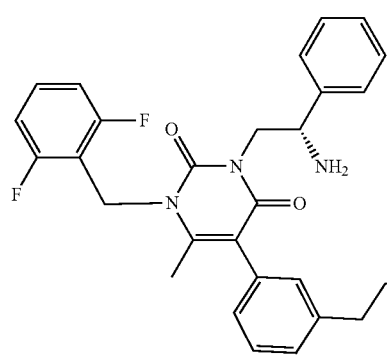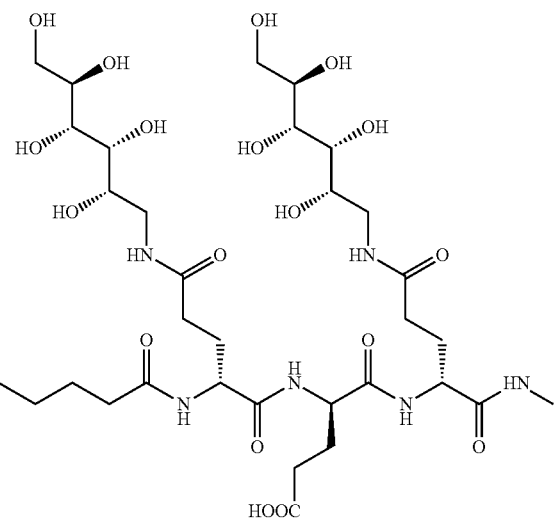

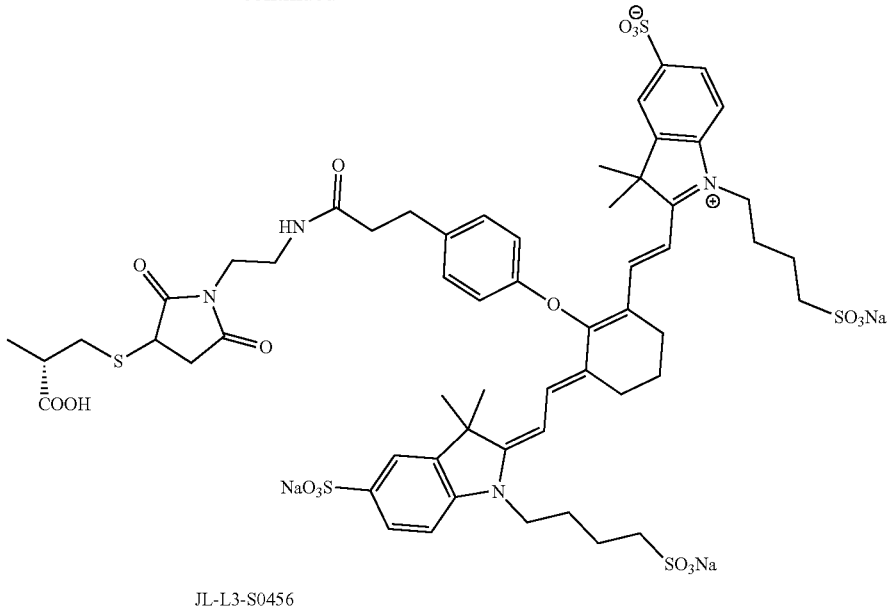

JL-L3-S0456

Scheme 3. Synthesis of JL-L3-50456, Reagents and conditions: (a) (i) 20% piperidine/DMF, rt, (ii) 3,4,5,6-di-isopropylidene-1-amino-deoxy(Fmoc-Glu-OH)-D-glucitol, PyBop, DMF, DIPEA, (b) (i) 20% piperidine/DMF, rt, 10 min (ii) Fmoc-Glu(OtBu)-OH, PyBop, DMF, DIPEA, (c) (i) 20% piperidine/DMF, rt, (ii) 3,4,5,6-di-isopropylidene-1-amino-deoxy(Fmoc-Glu-OH)-D-glucitol, PyBop, DMF, DIPEA, (d) (i) 20% piperidine/DMF, rt, 10 min (ii) Fmoc-8-amino-octanoic acid, PyBop, DMF, DIPEA, (e) (i) 20% piperidine/DMF, rt, 10 min (ii) JL, PyBop, DMF, DIPEA, (iii) TFA/H$_2$O/TIPS/EDT (92.5:2.5:2.5:2.5), 1 h, (f) JL-L2, S0456 maleimide, anhydrous DMSO, DIPEA, rt.

Synthesis of JL-L3: As described in Scheme 3, the linker was prepared by the standard solid phase peptide synthesis. The peptidoglycan subunit was synthesized as described elsewhere. JL was then coupled to the linker on the solid phase. The final product was cleaved from the H-Cys(Trt) 2-chlorotrityl resin using the standard cocktail solution of TFA:Water:TIPS: Ethanedithiol (95%: 2.5%: 2.5%: 2.5%). Crude JL-L3 was purified by using RP-HPLC [A=2 Mm ammonium acetate buffer (pH 5.0), B=acetonitrile, solvent gradient 0% B to 80% B in 35 min] to yield the requisite product. LRMS-LC/MS (m/z): [M+H]$^+$ calcd for C$_{67}$H$_{94}$F$_2$N$_{10}$O$_{23}$S, 1477; found 1478.

Synthesis of NIR conjugate JL-L3-S0456: 50456 dye containing the maleimide was synthesized as described in the Scheme 3. 1 equivalence of 50456-maleimide and JL-L3 were dissolved in anhydrous DMSO, followed by addition of 5 equivalences of DIPEA. The reaction mixture was stirred under argon atmosphere for 1 h. The completion of the reaction was monitored by using LC-MS. Crude JL-L3-S0456 was purified by using RP-HPLC [A=2 Mm ammonium acetate buffer (pH 7.0), B=acetonitrile, solvent gradient 0% B to 80% B in 35 min] to yield the requisite product. The LCMS characterization of JL-L3-S0456 was as follows. LRMS-LC/MS (m/z): [M+H]$^+$ calcd for C$_{120}$H$_{115}$F$_2$N$_{14}$Na$_3$O$_{39}$S$_5$, 2680.85; found 2682. LRMS-LC/MS trace of JR-L3-S0456 is shown in FIG. 3.

Compound Example 2. JL-L1A, JL-L2A, JL-L3A

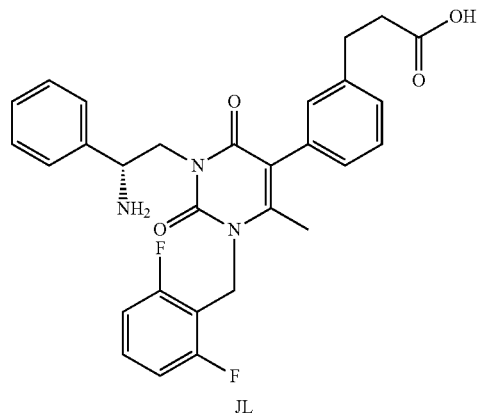

JL

-continued
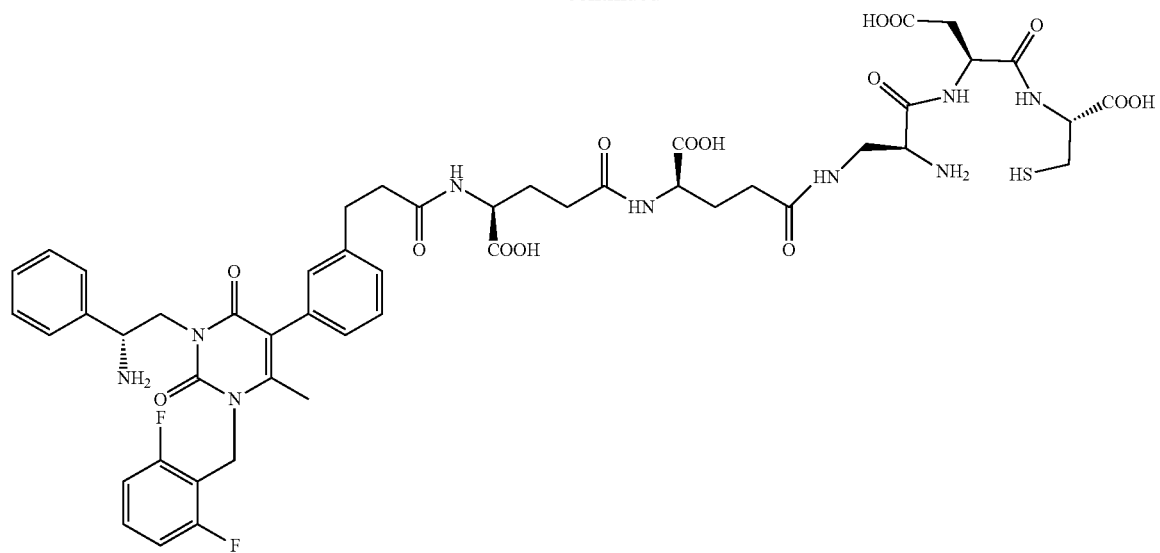
JL-L1A
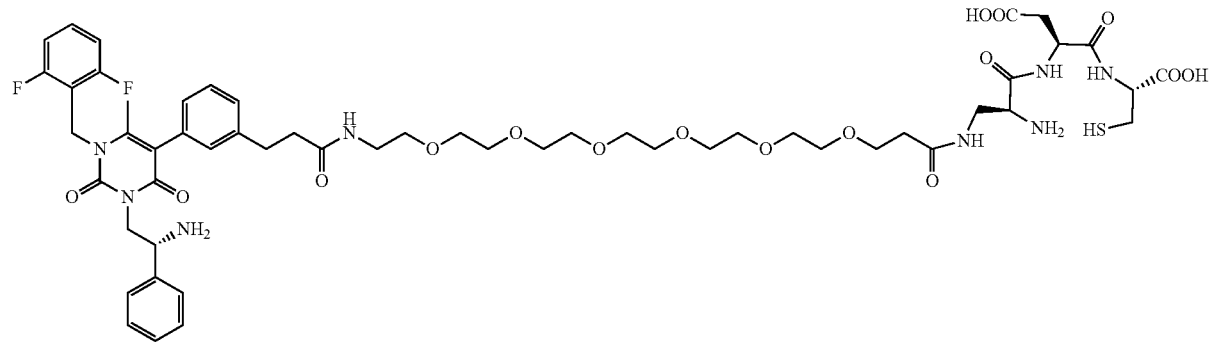
JL-L2A
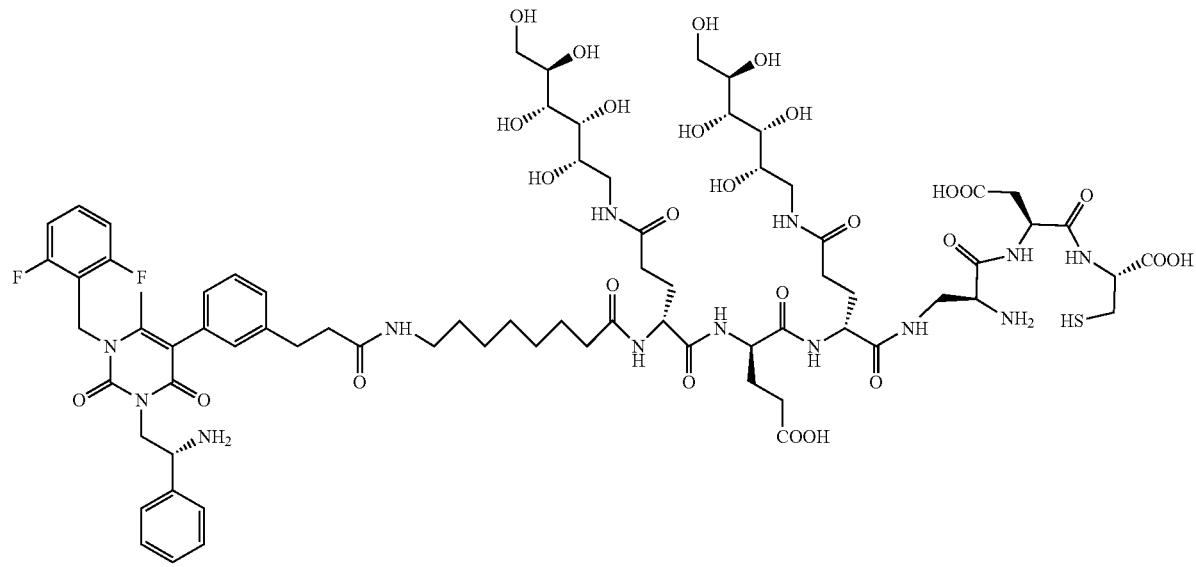
JL-L3A

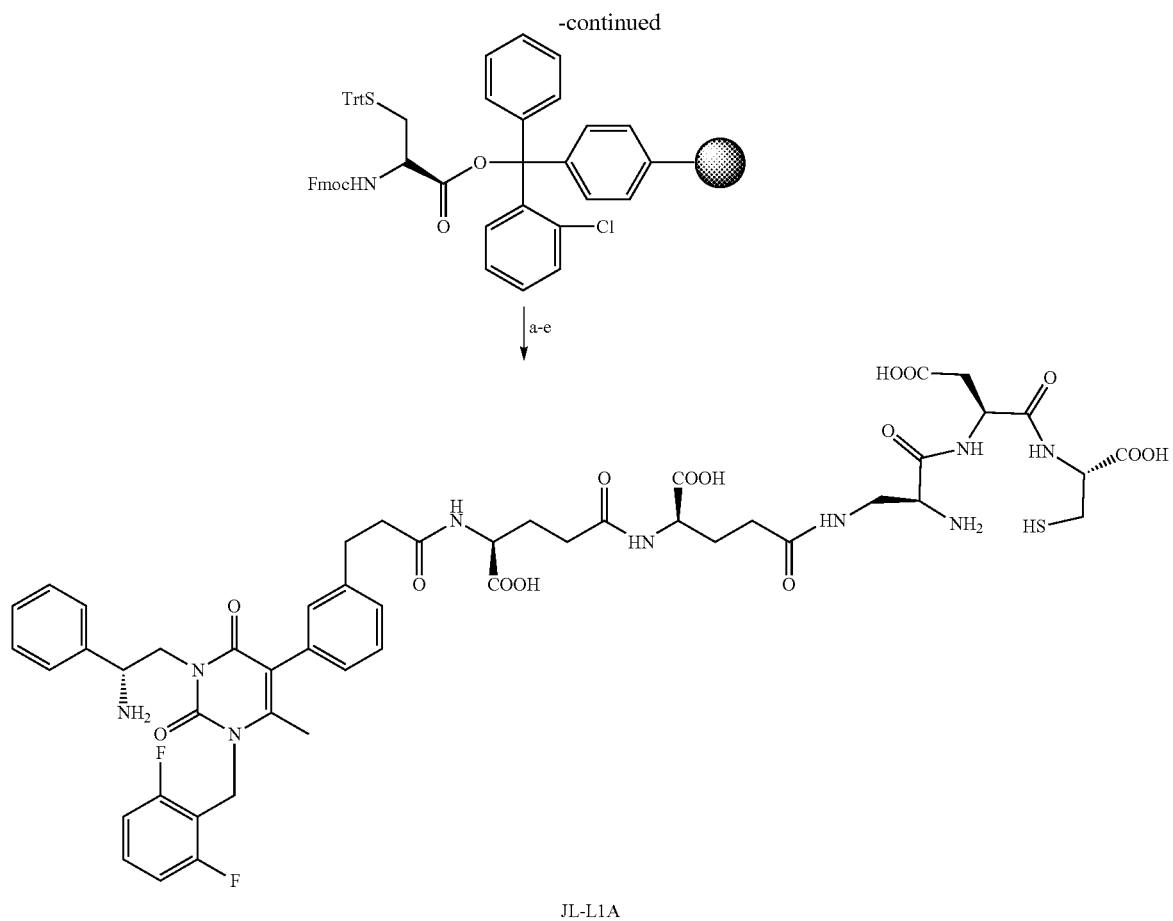

JL-L1A

Scheme 4. Synthesis of JL-L1A, Reagents and conditions: (a) (i) 20% piperidine/DMF, rt, (ii) Fmoc-Asp(OtBu), PyBop, DMF, DIPEA, (b) (i) 20% piperidine/DMF, rt, 10 min (ii) Fmoc-diaminopropionic (DAP) acid, PyBop, DMF, DIPEA, (c) (i) 20% piperidine/DMF, rt, 10 min (ii) N-Fmoc-L-glutamic acid alpha-tert-butyl ester, PyBop, DMF, DIPEA, (d) (i) 20% piperidine/DMF, rt, 10 min (ii) N-Fmoc-L-glutamic acid alpha-tert-butyl ester, PyBop, DMF, DIPEA, (e) (i) 20% piperidine/DMF, rt, 10 min (ii) JL, PyBop, DMF, DIPEA, (iii) TFA/H$_2$O/TIPS/EDT (92.5:2.5:2.5:2.5), 1 h.

Synthesis of JL-L1A. LHRH-R targeting ligand was synthesized according to the published procedure in Tucci, F. C., et al. Journal of medicinal chemistry, 48(4), 1169-1178 which is incorporated by reference herein. The parent molecule was modified to replace the ether functionality of the molecule with a carboxylic acid group. The modified ligand is referred to herein as JL. Synthesis of all the conjugates was performed by standard solid phase peptide synthesis. The components of the conjugate were built on the H-Cys (Trt)2-chlorotrityl resin. The standard cocktail solution of TFA:Water:TIPS:Ethanedithiol (95%: 2.5%: 2.5%: 2.5%) was used to cleave the final conjugate from the resin. Crude product was purified by using RP-HPLC [A=2 Mm ammonium acetate buffer (pH 5.0), B=acetonitrile, solvent gradient 0% B to 80% B in 35 min] to yield the requisite product. LRMS-LC/MS (m/z): [M+H]$^+$ calcd for $C_{49}H_{57}F_2N_9O_{15}S$, 1082.1; found 1083.

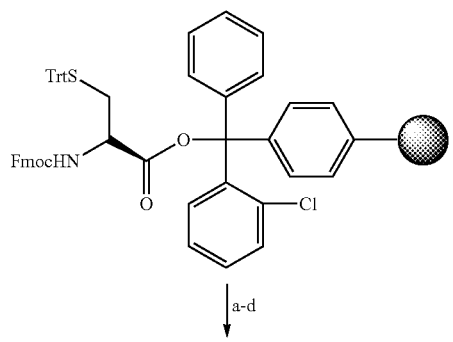

-continued

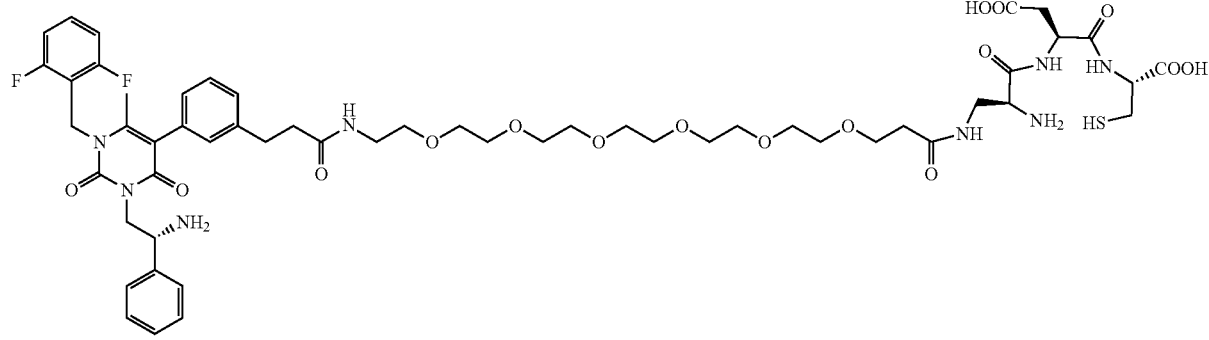

JL-L2A

Scheme 5. Synthesis of JL-L2A, Reagents and conditions: (a) (i) 20% piperidine/DMF, rt, (ii) Fmoc-Asp(OtBu), PyBop, DMF, DIPEA, (b) (i) 20% piperidine/DMF, rt, 10 min (ii) Fmoc-diaminopropionic (DAP) acid, PyBop, DMF, DIPEA, (c) (i) 20% piperidine/DMF, rt, (ii) Fmoc-N-amido-dPEG$_6$-acid, PyBop, DMF, DIPEA, (d) (i) 20% piperidine/DMF, rt, 10 min (ii) JL, PyBop, DMF, DIPEA, (iii) TFA/H$_2$O/TIPS/EDT (92.5:2.5:2.5:2.5), 1 h.

Synthesis of JL-L2A. LHRH-R targeting ligand was synthesized according to the published procedure in Tucci, F. C., et al. Journal of medicinal chemistry, 48(4), 1169-1178 which is incorporated by reference herein. The parent molecule was modified to replace the ether functionality of the molecule with a carboxylic acid group. The modified ligand is referred to herein as JL. Synthesis of all the conjugates was performed by standard solid phase peptide synthesis. The components of the conjugate were built on the H-Cys (Trt)2-chlorotrityl resin. The standard cocktail solution of TFA:Water:TIPS:Ethanedithiol (95%: 2.5%: 2.5%: 2.5%) was used to cleave the final conjugate from the resin. Crude product was purified by using RP-HPLC [A=2 Mm ammonium acetate buffer (pH 5.0), B=acetonitrile, solvent gradient 0% B to 80% B in 35 min] to yield the requisite product. LRMS-LC/MS (m/z): [M+H]$^+$ calcd for C$_{54}$H$_{72}$F$_2$N$_8$O$_{16}$S, 1159.27; found 1160.

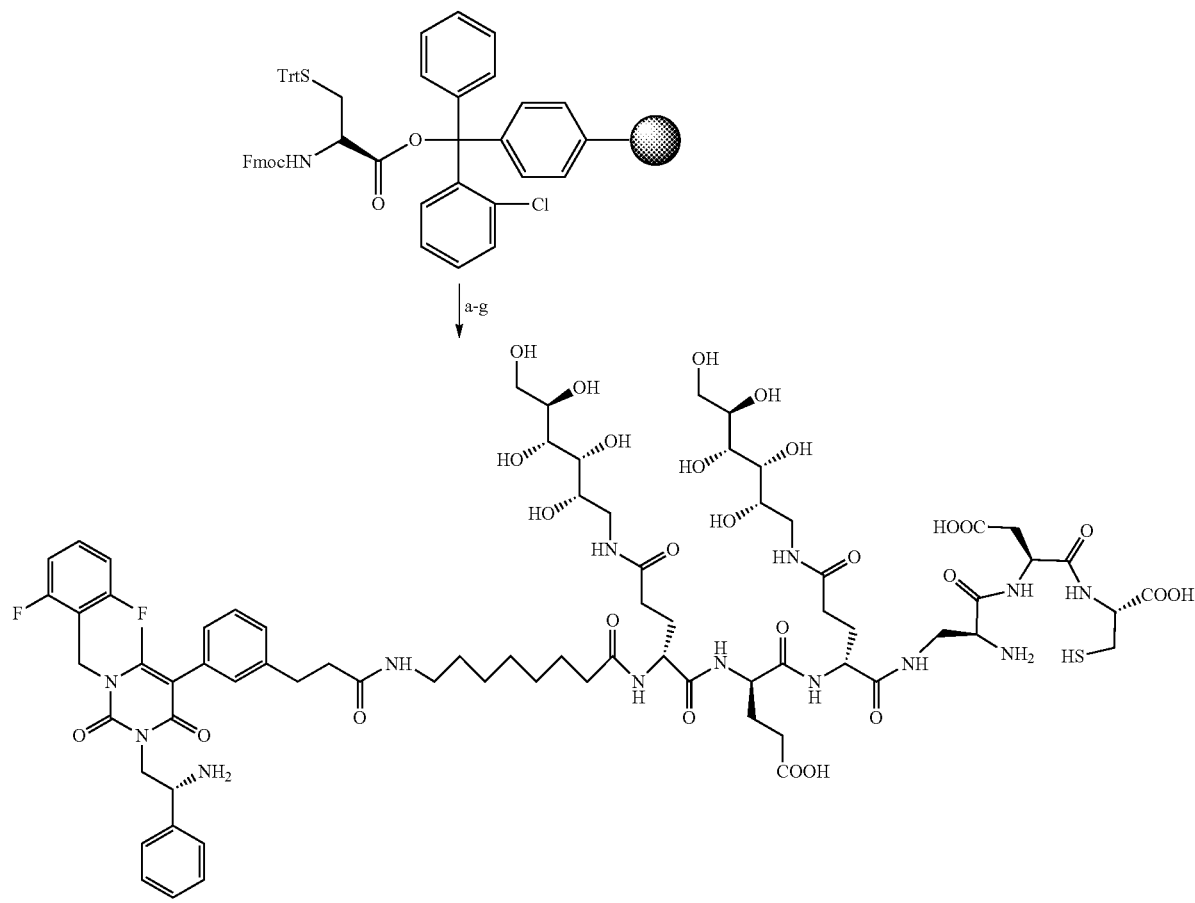

JL-L3A

Scheme 6. Synthesis of JL-L3A, Reagents and conditions: (a) (i) 20% piperidine/DMF, rt, (ii) Fmoc-Asp(OtBu), PyBop, DMF, DIPEA, (b) (i) 20% piperidine/DMF, rt, 10 min (ii) Fmoc-diaminopropionic (DAP) acid, PyBop, DMF, DIPEA, (c) (i) 20% piperidine/DMF, rt, (ii) 3,4,5,6-di-isopropylidene-1-amino-deoxy(Fmoc-Glu-OH)-D-glucitol, PyBop, DMF, DIPEA, (d) (i) 20% piperidine/DMF, rt, 10 min (ii) N-Fmoc-L-glutamic acid alpha-tert-butyl ester, PyBop, DMF, DIPEA, (e)) (i) 20% piperidine/DMF, rt, (ii) 3,4,5,6-di-isopropylidene-1-amino-deoxy(Fmoc-Glu-OH)-D-glucitol, PyBop, DMF, DIPEA, (f) (i) 20% piperidine/DMF, rt, 10 min (ii) Fmoc-8-amino-octanoic acid, PyBop, DMF, DIPEA, (e) (i) 20% piperidine/DMF, rt, 10 min, (g)) (i) 20% piperidine/DMF, rt, 10 min (ii) JL, PyBop, DMF, DIPEA, (iii) TFA/H$_2$O/TIPS/EDT (92.5:2.5:2.5:2.5), 1 h.

Figure 4A:
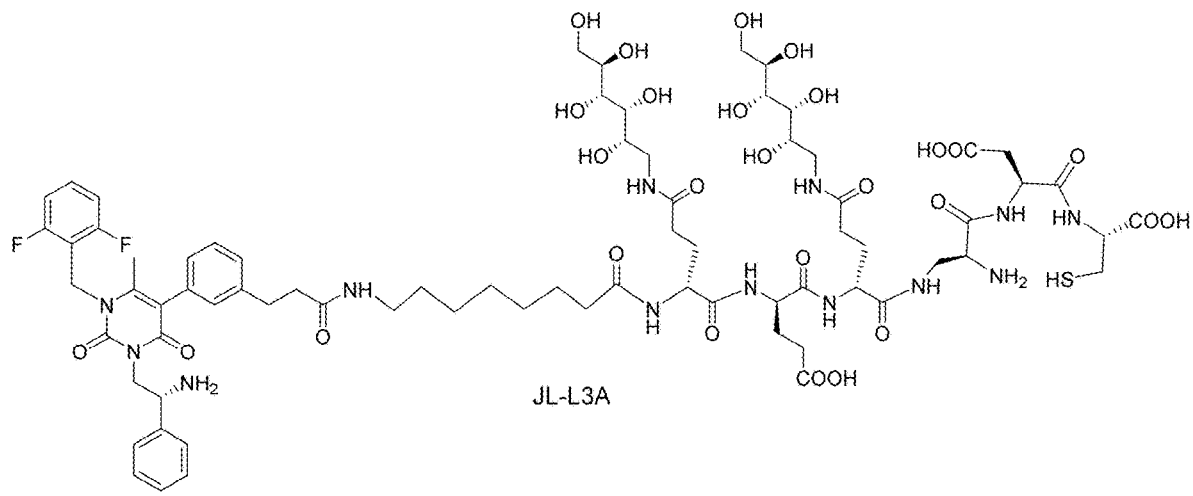
FIGS. 4A-4B show the chemical structure (FIG. 4A) and a radioactive HPLC profile (FIG. 4B) for JR-L3-A. Parameters: Column=Sunfire C18, 2.5 μm, 3.0×50 mm; A=0.1% TFA in water; B=Acetonitrile; Colmun Temperature=25° C.; Gradient=15% B to 50% B in 10 min.; Flow Rate=0.6 mL/min. Peak Results: Peak 1, RT=0.500, Area=13269, Height=2360, % Area=1.31; Peak 2, RT=6.061, Area=12561, Height=1110, % Area=1.24; Peak 3, RT=6.461, Area=470343, Height=68900, % Area=46.40; Peak 4, RT=6.561, Area=517424, Height=65540, % Area=51.05; Sum Area=1013595.7.
Figure 4B:
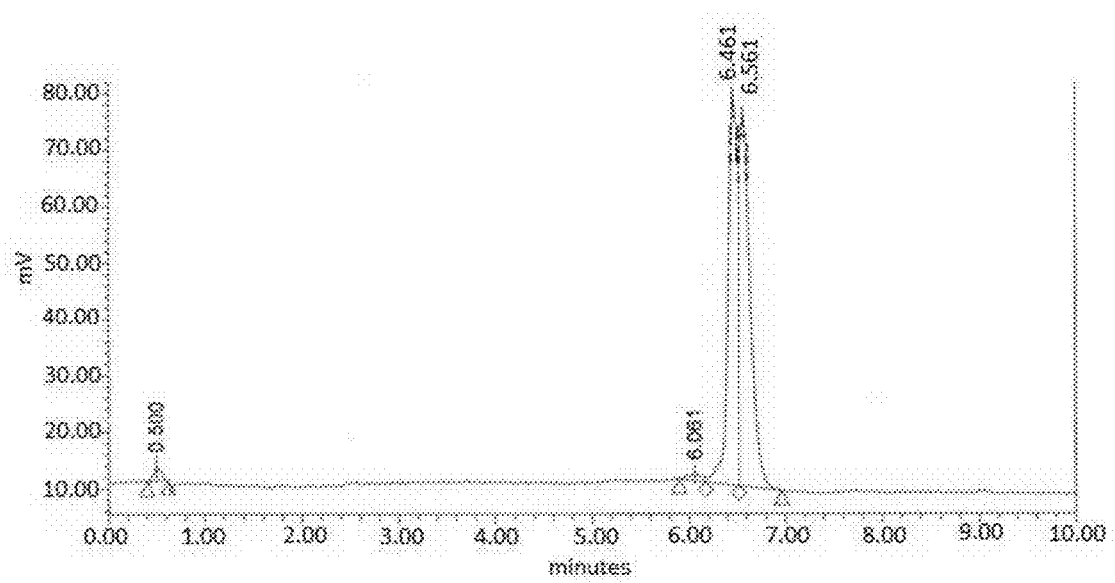

Synthesis of JL-L3A. LHRH-R targeting ligand was synthesized according to the published procedure in Tucci, F. C., et al. Journal of medicinal chemistry, 48(4), 1169-1178 which is incorporated by reference herein. The parent molecule was modified to replace the ether functionality of the molecule with a carboxylic acid group. The modified ligand is referred to herein as JL. Synthesis of all the conjugates was performed by standard solid phase peptide synthesis. The components of the conjugate were built on the H-Cys (Trt)2-chlorotrityl resin. The standard cocktail solution of TFA:Water:TIPS:Ethanedithiol (95%: 2.5%: 2.5%: 2.5%) was used to cleave the final conjugate from the resin. Crude product was purified by using RP-HPLC [A=2 Mm ammonium acetate buffer (pH 5.0), B=acetonitrile, solvent gradient 0% B to 80% B in 35 min] to yield the requisite product. LRMS-LC/MS (m/z): [M+H]$^+$ calcd for C$_{74}$H$_{105}$F$_2$N$_{13}$O$_{27}$S, 1678.77; found 1678. JL-L3A radioactive HPLC Profile is shown in FIG. 4.

Formulation of non-radioactive JL-L1A, JL-L2A and JL-L3A vials. Prior to radiolabeling with $^{99m}$Tc the conjugates were formulated according to procedure published in Leamon, C. P., et al. Bioconjugate chemistry, 13(6), 1200-1210, which is incorporated by reference herein. The 0.1 mg of JL-L1A, 80 mg of sodium α-D-glucoheptonate, and 10 mg of tin (II) hydrochloride, were dissolved in argon purged water. The pH of the solution was adjusted to 6.8±0.2 with sodium hydroxide or hydrochloric acid. The final volume was adjusted to 10 ml and then transferred to 10 vials containing 1 ml each of the above solution and lyophilized. The lyophilized powder was sealed in the vials under argon and stored at -20° C. Same procedure was followed to formulate JL-L2A and JL-L3A.

$^{99m}$Tc labelling of JL-L1A, JL-L2A and JL-L3A. Radiolabeling of the conjugates was performed according to procedure published in Leamon, C. P., et al. Bioconjugate chemistry, 13(6), 1200-1210, which is incorporated by reference herein. To a formulated vial of JL-L1A 1 ml of $^{99m}$Tc sodium pertechnetate was added and heated for ~18 min at 100° C. The chelated solution was allowed to cool to room temperature before using it for in vitro and in vivo studies. The chelation efficiency of the conjugates was confirmed by HPLC. All the three conjugates showed more than 95% chelation efficiency.

Compound Example 3. JL-L2-Rhodamine, JR-L3, JR-L3-TubBH

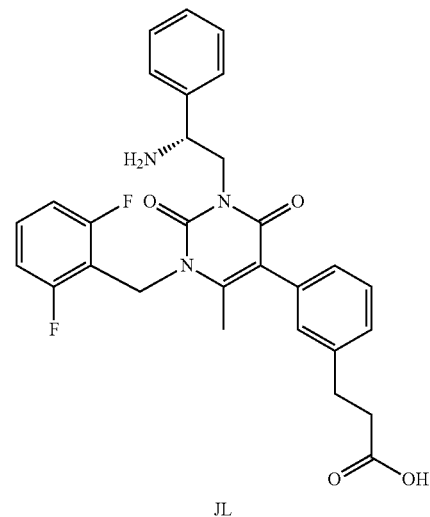

JL

Figure 5A:
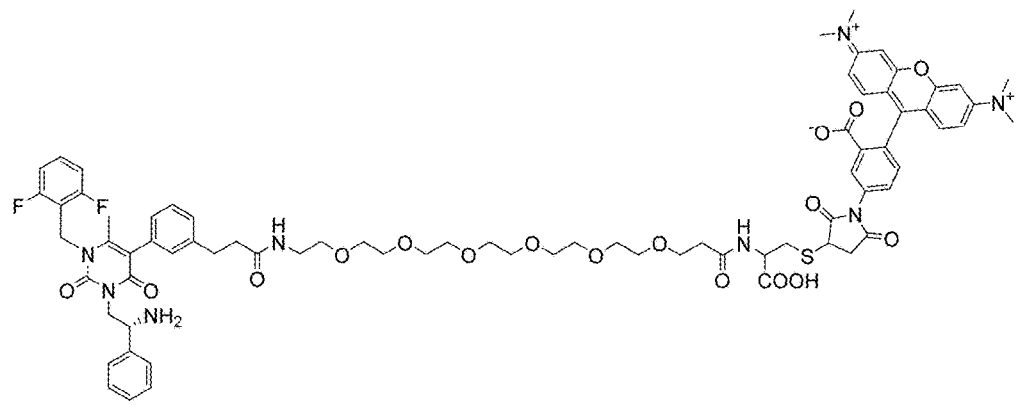
FIGS. 5A-5C show the chemical structure (FIG. 5A) and an LC/MS trace (FIGS. 5B and 5C) for JR-L2-Rhodamine.
Figure 5B:
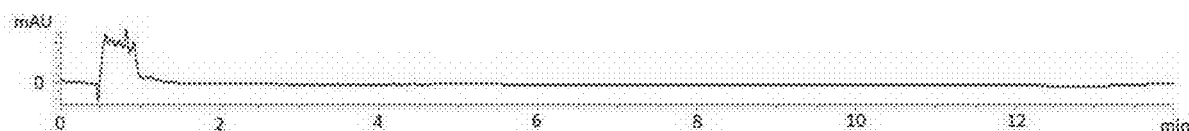
Figure 5C:
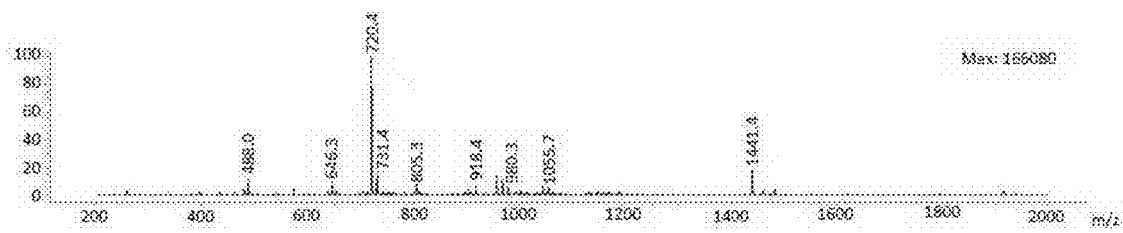

-continued
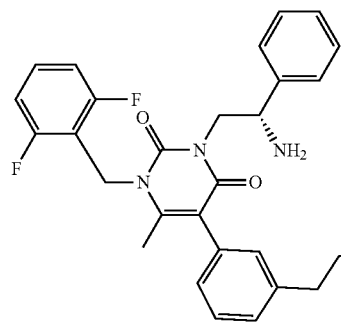
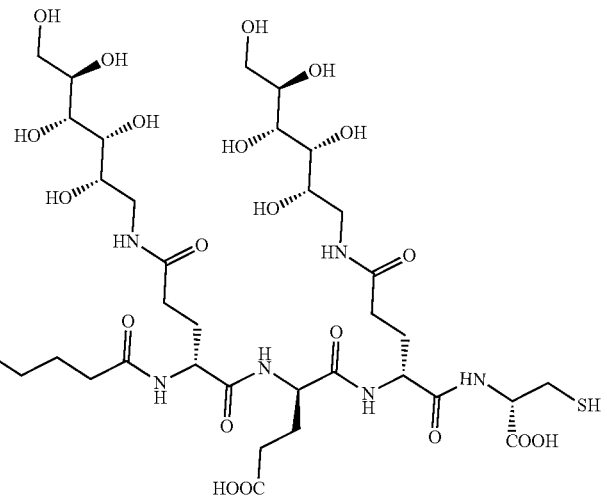
JL-L3
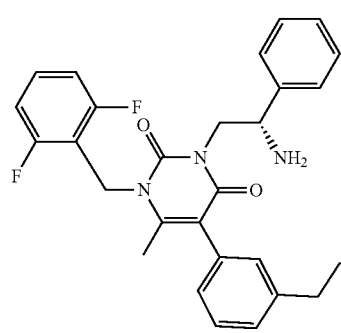
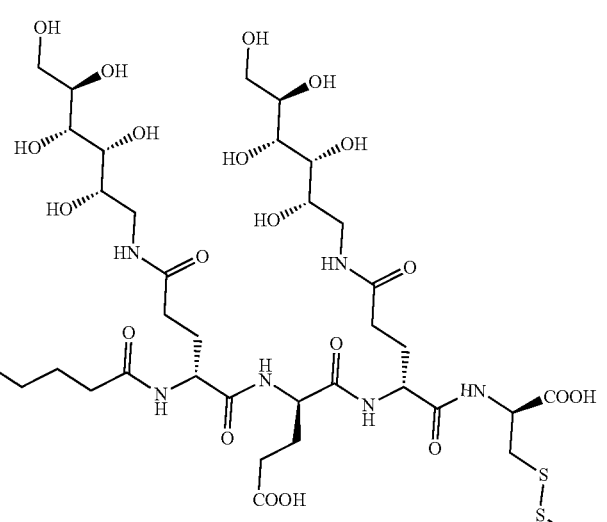
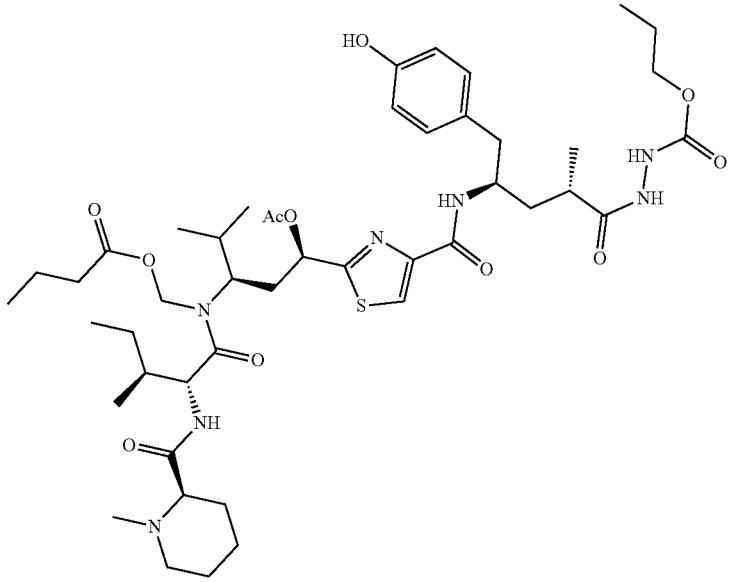
JL-L3-TubBH -continued
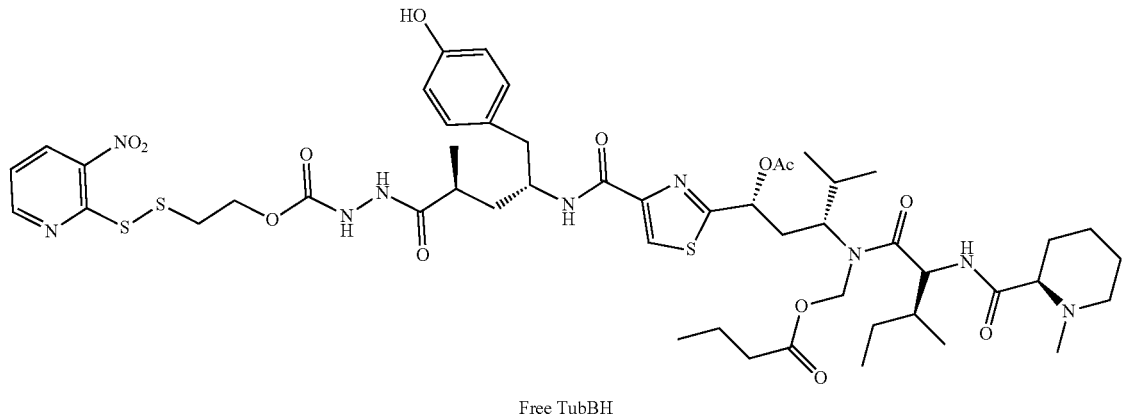
Free TubBH
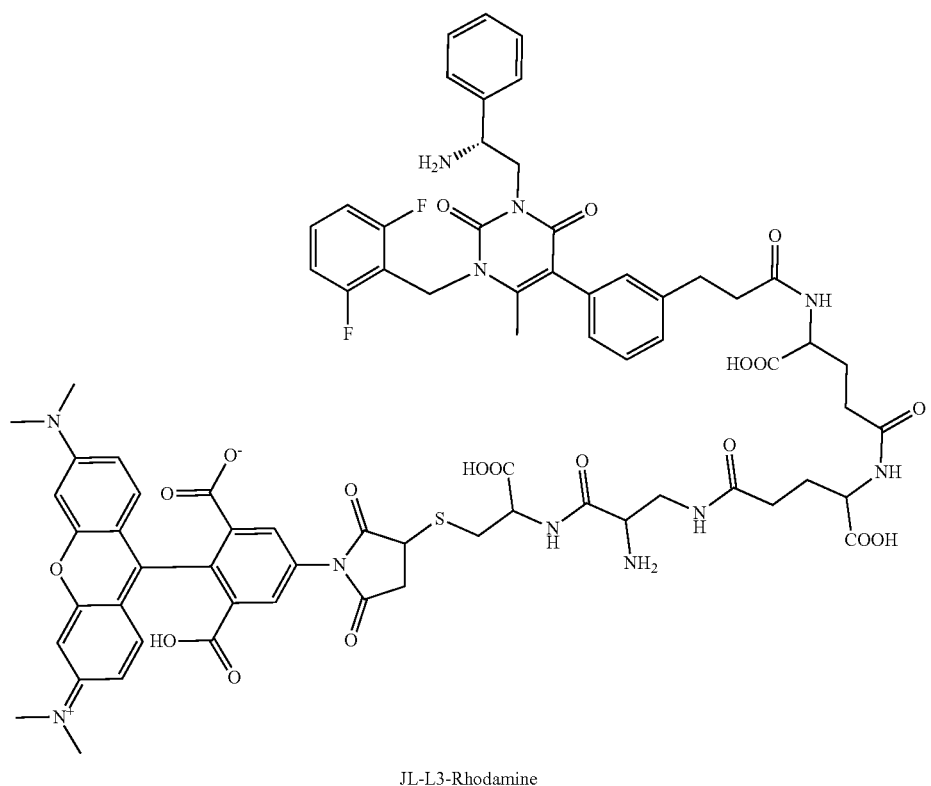
JL-L3-Rhodamine
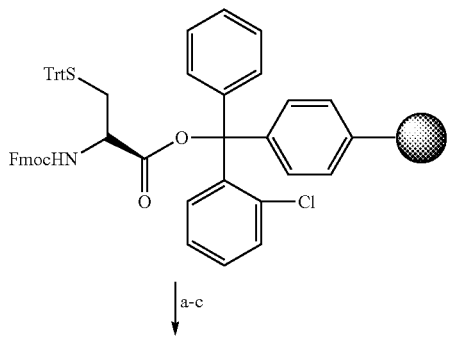
↓ a-c -continued
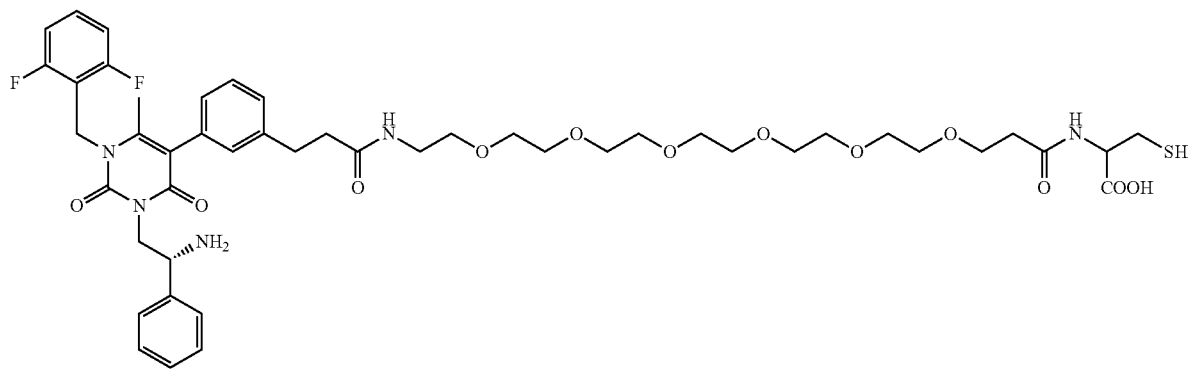
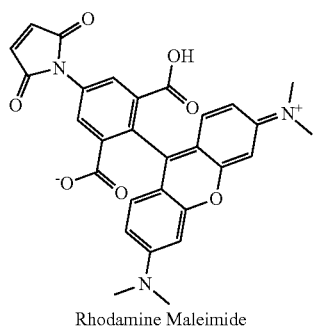
Rhodamine Maleimide
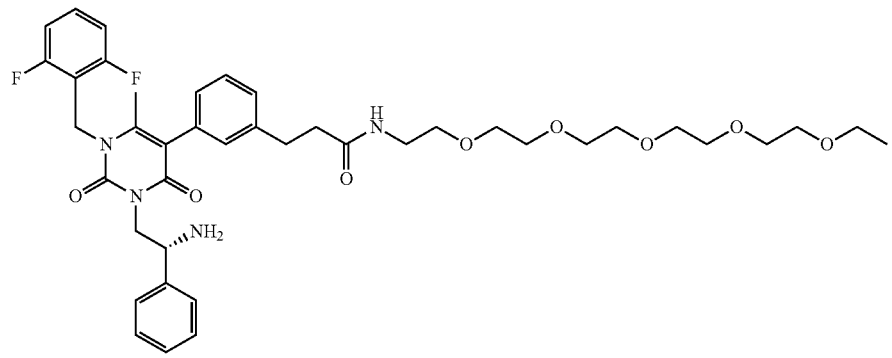
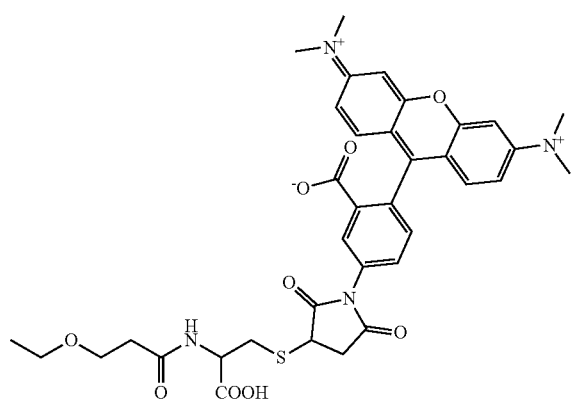
JR-L2-Rhodamine Scheme 7. Synthesis of JR-L2-Rhodamine, Reagents and conditions: (a) (i) 20% piperidine/DMF, rt, (ii) Fmoc-N-amido-dPEG$_6$-acid, PyBop, DMF, DIPEA, (b) (i) 20% piperidine/DMF, rt, 10 min (ii) JL, PyBop, DMF, DIPEA, (c) TFA/H$_2$O/TIPS/EDT (92.5:2.5:2.5:2.5), 1 h, (d) JL-L2, Rhodamine maleimide, anhydrous DMSO, DIPEA, rt product was purified by preparative RP-HPLC [A=2 mM ammonium acetate buffer (pH 7.0), B=acetonitrile, solvent gradient 0% B to 50% B in 35 min] to yield 90% of the desired product. LRMS-LC/MS (m/z): [M+H]$^+$ calcd for, C$_{75}$H$_{84}$F$_2$N$_8$O$_{17}$S, 1439.59; found 1440. LRMS-LC/MS trace of JR-L2-Rhodamine is shown in FIG. 5.

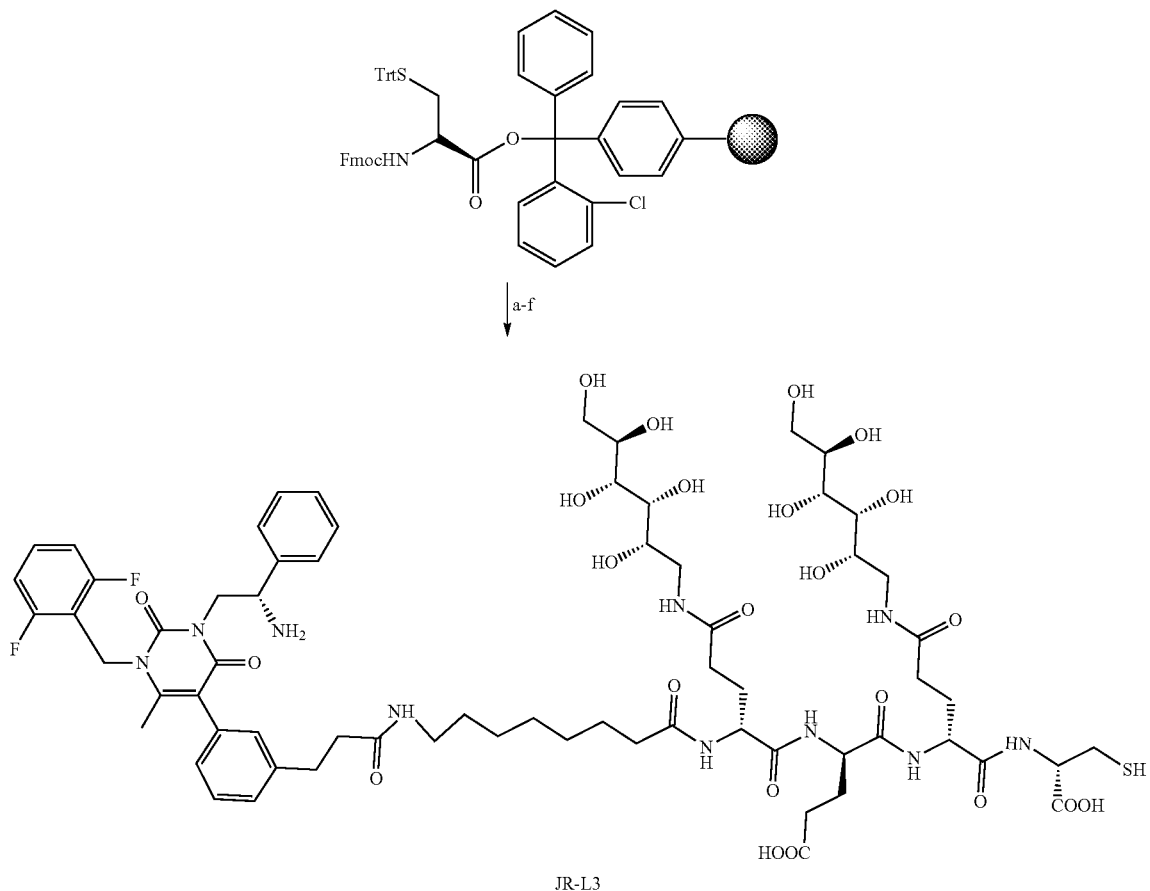

JR-L3

Synthesis of JL-L2: The LHRH-R antagonist (JL) was synthesized according to the previously published procedure[27] except at the last step instead of ether derivative of the reactant, a carboxylic acid derivative was used. This modification was made for the ease of coupling with the linker. The linker was prepared by the standard solid phase peptide synthesis as described in SI FIG. 1. JL was further coupled to the linker on the solid phase. After completion of the coupling the product was cleaved from the resin using the cocktail solution of TFA:Water:TIPS: Ethanedithiol (95%: 2.5%: 2.5%: 2.5%). Crude JL-L2 was purified by using RP-HPLC [A=2 Mm ammonium acetate buffer (pH 5.0), B=acetonitrile, solvent gradient 0% B to 80% B in 35 min] to yield 70% of the desired product. LRMS-LC/MS (m/z): [M+H]$^+$ calcd for C$_{47}$H$_{61}$F$_2$N$_5$O$_{12}$S, 958.08; found 959.

Synthesis of JL-L2-Rhodamine: To synthesize the rhodamine dye conjugate, purified JL-L2 and rhodamine maleimide (1 eq) were dissolved in anhydrous DMSO and DIPEA (2 eq). The reaction mixture was stirred under argon atmosphere at room temperature. (SI FIG. 1) Progress of the reaction was monitored using analytical LRMS-LCMS. After 1 h the reaction was found to reach completion. Crude Scheme 8. Synthesis of JR-L3, Reagents and conditions: (a) (i) 20% piperidine/DMF, rt, (ii) 3,4,5,6-di-isopropylidene-1-amino-deoxy(Fmoc-Glu-OH)-D-lucitol, PyBop, DMF, DIPEA, (b) (i) 20% piperidine/DMF, rt, (ii) Fmoc-Glu(OtBu)-OH, PyBop, DMF, DIPEA, (c) (i) 20% piperidine/DMF, rt, (ii) 3,4,5,6-Di-isopropylidene-1-amino-deoxy (Fmoc-Glu-OH)-D-glucitol, PyBop, DMF, DIPEA, d) (i) 20% piperidine/DMF, rt, (ii) Fmoc-8-amino-octanoic acid, PyBop, DMF, DIPEA, 4 h (e) (i) 20% piperidine/DMF, rt, 10 min (ii) JL, PyBop, DMF, DIPEA, (f) TFA/H$_2$O/TIPS/EDT (92.5:2.5:2.5:2.5), 1 h.

Figure 6A:
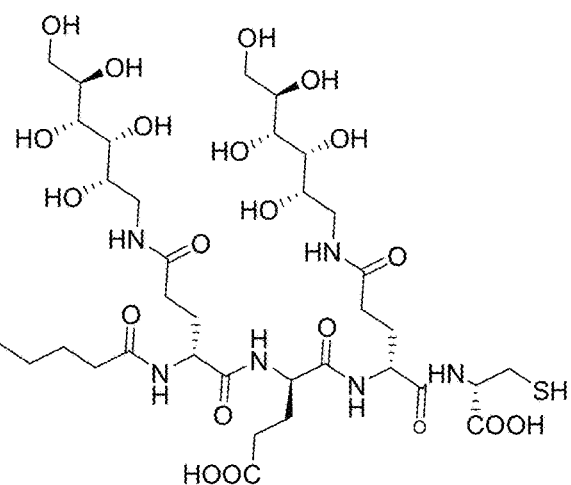
FIGS. 6A-6C show the chemical structure (FIG. 6A) and an LC/MS trace (FIGS. 6B and 6C) for JR-L3.
Figure 6B:
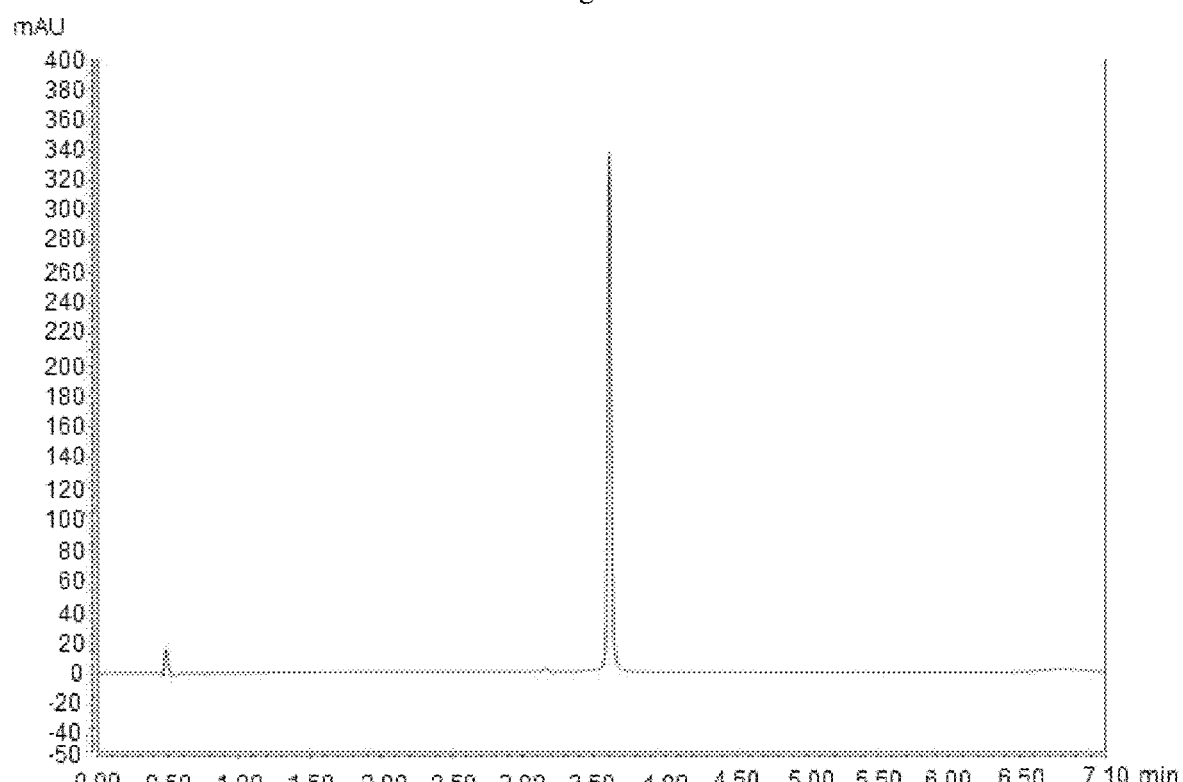
Figure 6C:
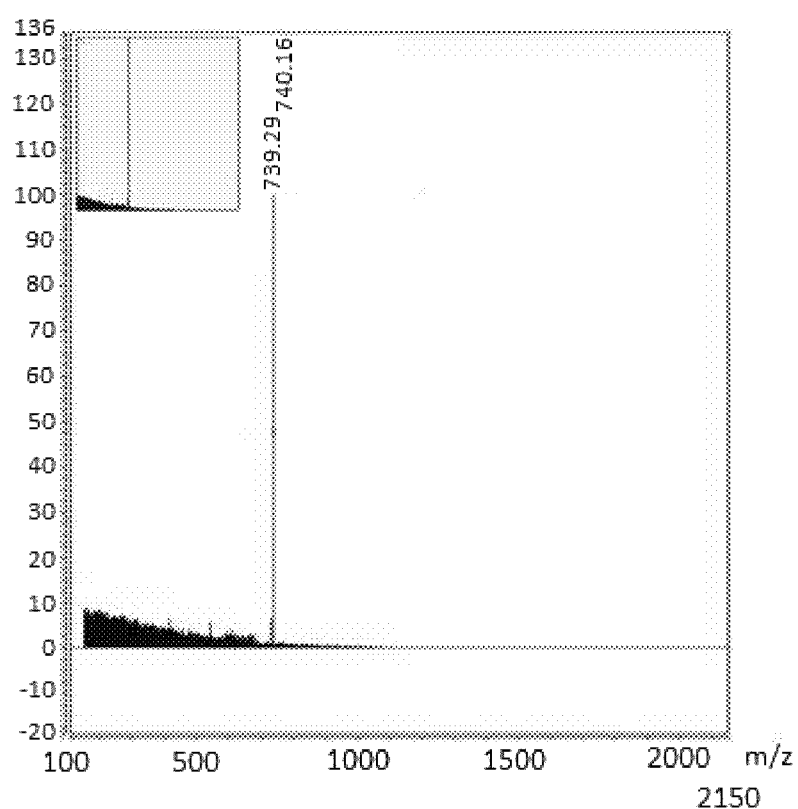

Synthesis of JL-L3: JL-L3 was prepared by the standard solid phase peptide synthesis as described in SI FIG. 2. The final product was cleaved from the resin by using the cocktail solution of TFA:Water:TIPS: Ethanedithiol (95%: 2.5%: 2.5%: 2.5%). Crude JL-L3 was purified by using RP-HPLC [A=2 Mm ammonium acetate buffer (pH 5.0), B=acetonitrile, solvent gradient 0% B to 80% B in 35 min] to yield 80% of the desired product. LRMS-LC/MS (m/z): [M+H]$^+$ calcd for C$_{67}$H$_{94}$F$_2$N$_{10}$O$_{23}$S, 1477.59; found 1478. LRMS-LC/MS trace of JR-L3 is shown in FIG. 6.

85 86
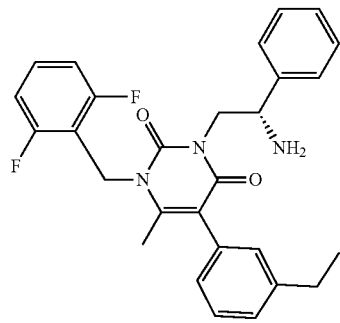
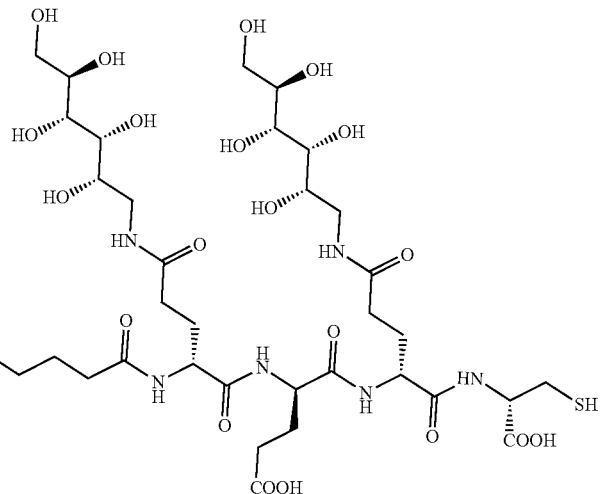
JR-L3
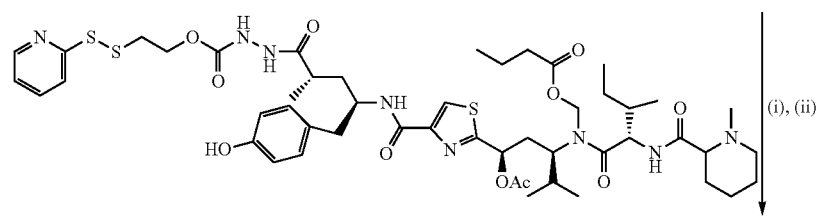
(i), (ii)
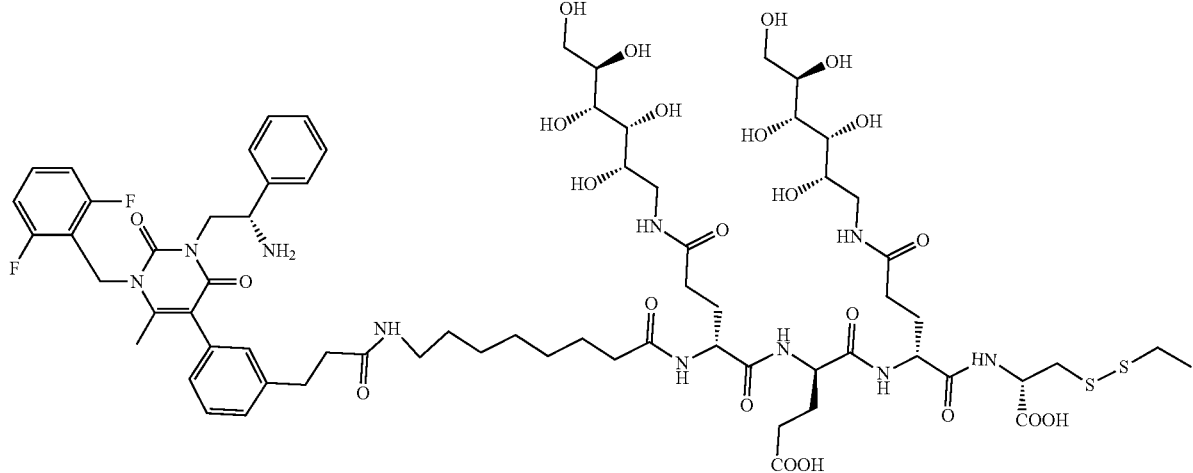
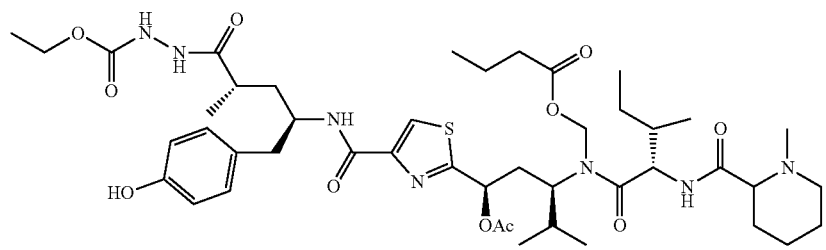
JR-L3-TubBH Scheme 9. Synthesis of JR-L3-TubBH, Reagents and conditions: (i) JL-L3, H$_2$O/NaHCO$_3$ (pH=7.0-7.2), Argon, r.t. (ii) activated TubBH, anhydrous THF, argon, r.t.

Synthesis of JL-L3-TubBH: Tubulysin B hydrazide conjugate was synthesized as described below. Saturated solution of sodium bicarbonate in HPLC grade water was purged with argon for 15 min. JL-L3 was dissolved in HPLC grade argon purged water and the pH was then adjusted to the 7.0 using saturated sodium bicarbonate solution. To this reaction mixture, disulfide activated tubulysin B hydrazide (1 eq) in THF was added. The reaction mixture was allowed to stir at room temperature under argon atmosphere. The progress of the reaction was monitored using analytical LRMS-LCMS. After 30 minutes the reaction was found to reach completion. Crude product was purified by preparative RP-HPLC [A=2 Mm ammonium acetate buffer (pH 7.0), B=acetonitrile, solvent gradient 0% B to 80% B in 35 min] to yield 90% of the desired product. LRMS-LC/MS (m/z): [M+H]$^+$ calcd for C$_{112}$H$_{161}$F$_2$N$_{17}$O$_{34}$S$_3$, 2423.78; found 2424.

Figure 7A:
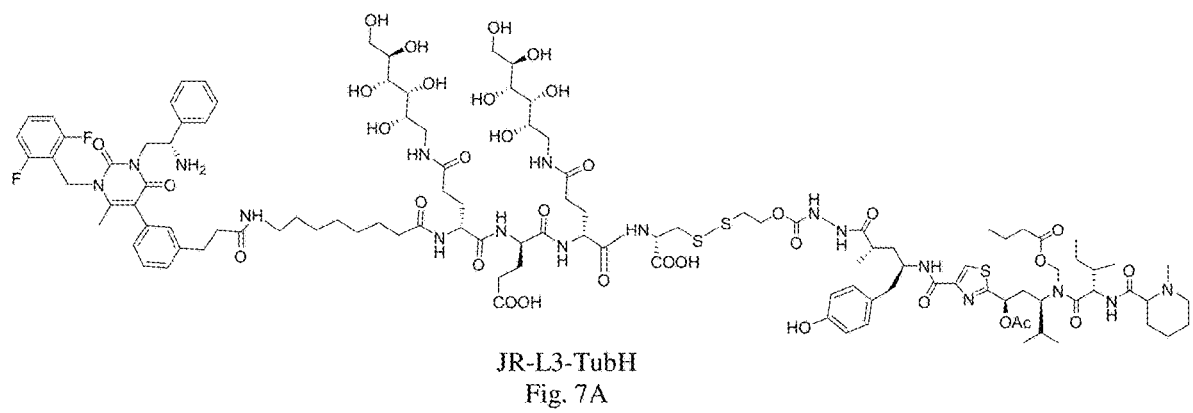
FIGS. 7A-7C show the chemical structure (FIG. 7A) and an LC/MS trace (FIGS. 7B and 7C) for JR-L3-TubBH.
Figure 7B:
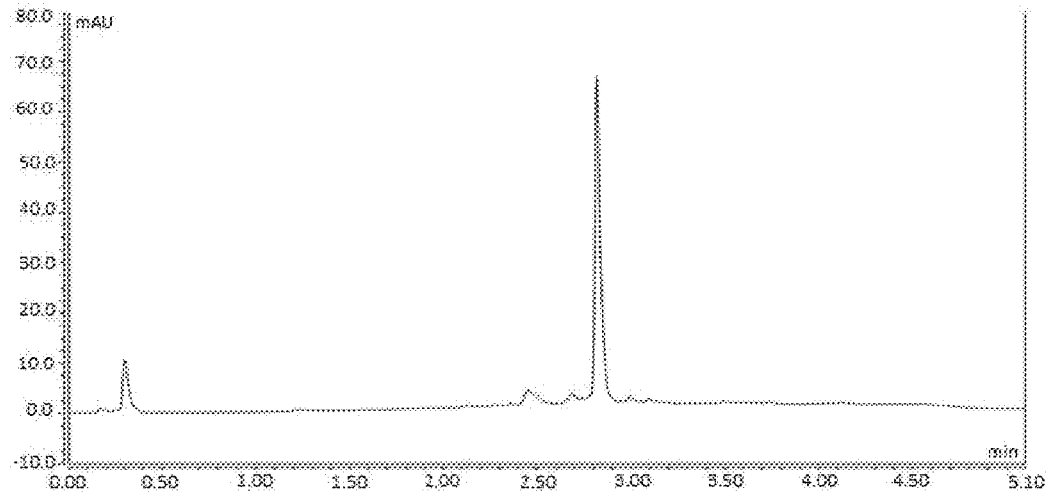
Figure 7C:
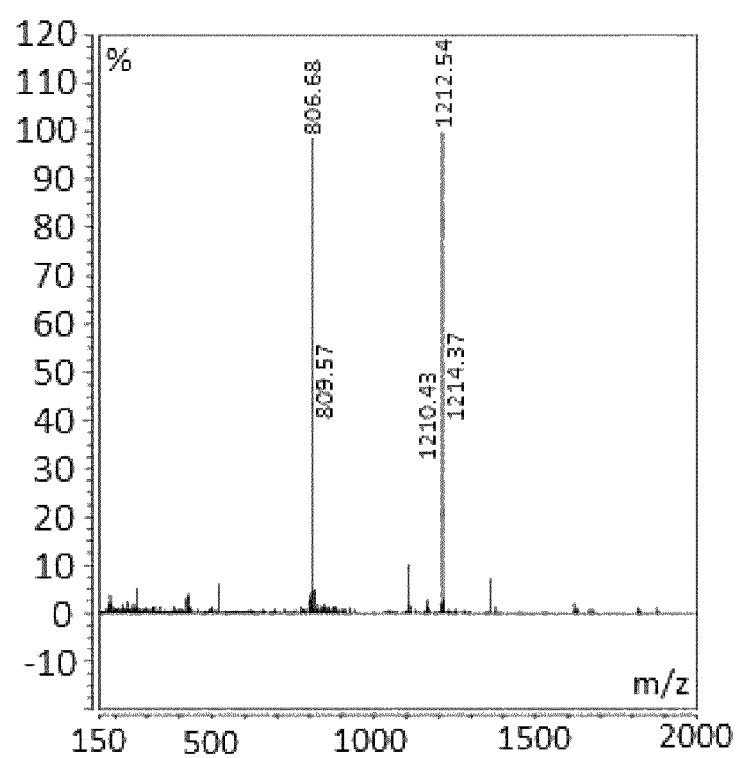
Figure 8A:
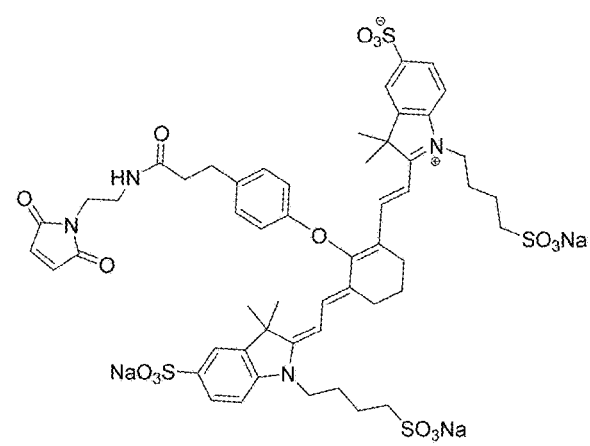
FIGS. 8A-8D show the chemical structure (FIG. 8A) and an LC/MS trace (FIGS. 3B-3D) for S0456 maleimide.
Figure 8B:
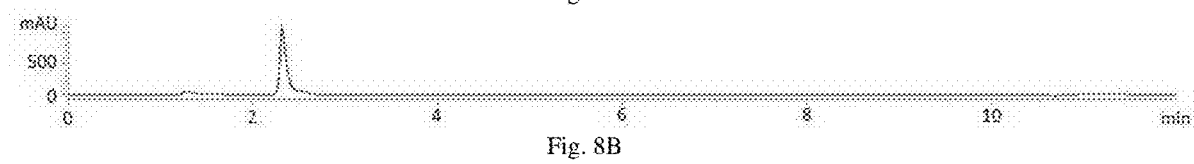
Figure 8C:
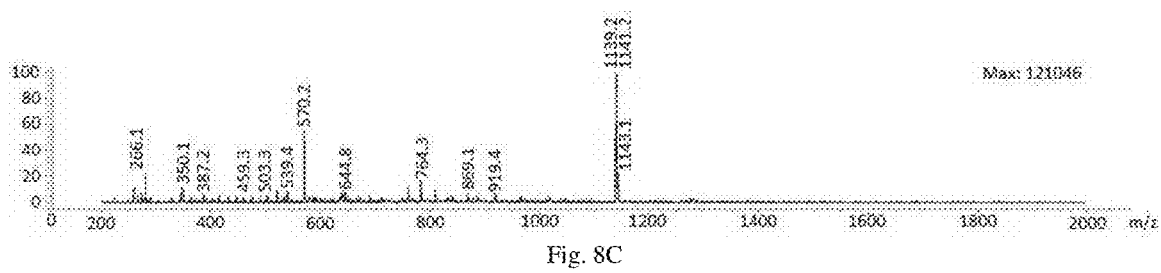
Figure 8D:
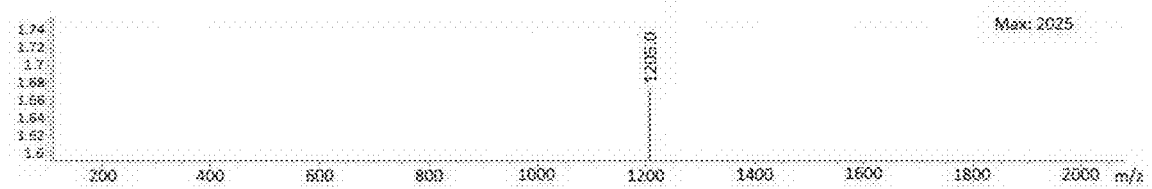

Cell culture: LHRH-R positive breast cancer cell, MDA-MB231 and LHRH-R negative ovarian cancer cells SKVO3 cells lines were cultured in RPMI 1640 medium supplemented with 10% fetal bovine serum and 1% penicillin-streptomycin at 37° C. in a 95% humidified air and 5% CO$_2$ atmosphere. LRMS-LC/MS trace of JR-L3-TubBH is shown in FIG. 7.

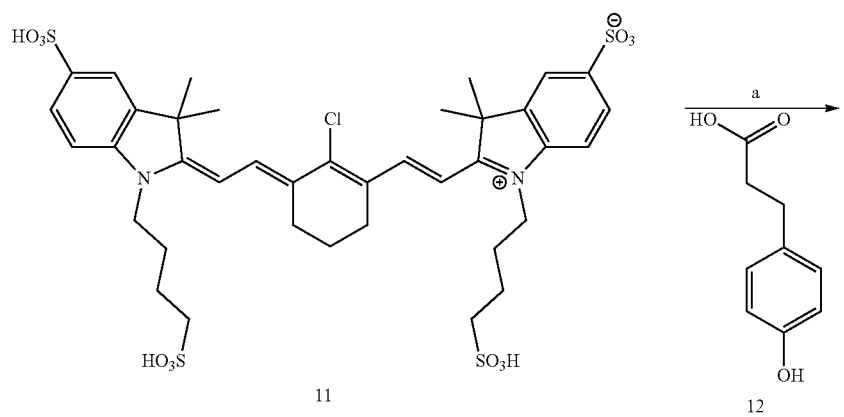

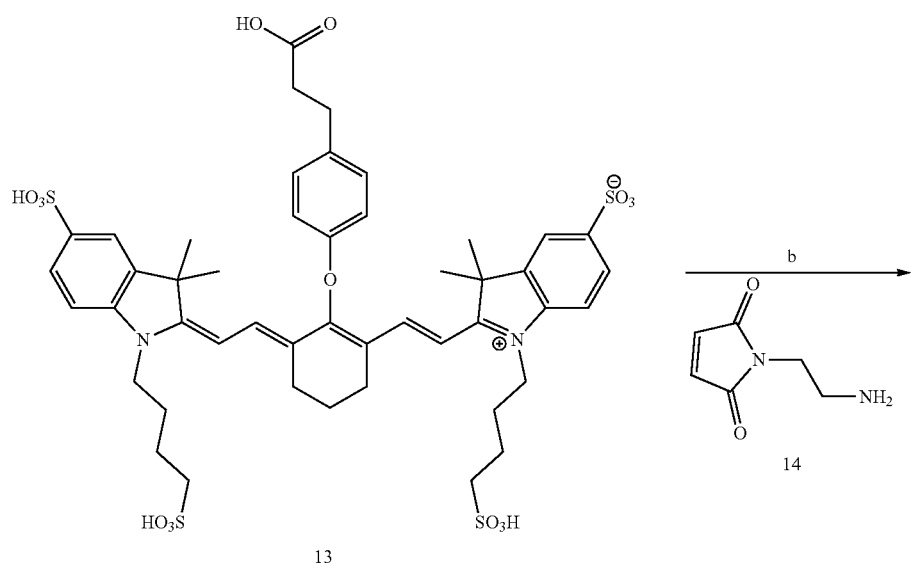

-continued

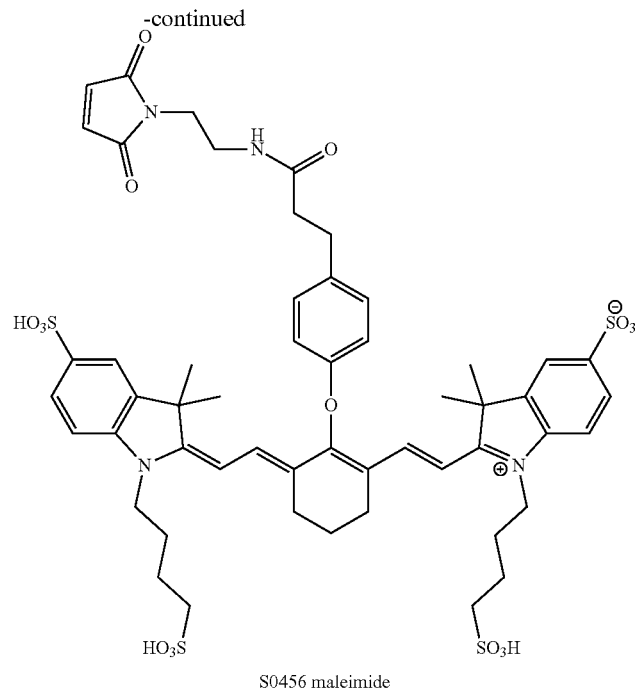

S0456 maleimide

Scheme 10. Synthesis of 50456 maleimide. Reagents and conditions: a) KOH, H$_2$O, rt—100° C.; b) HATU, Anhy. DIPEA, Anhy. DMF, rt. LC/MS trace of 50456 maleimide is shown in FIG. 8.

METHOD EXAMPLES

Method Example 1. JL-L1-S0456, JL-L2-S0456, JL-L3-S0456

Cell Culture: MDA-MB231 breast cancer cells, HEC-1B endometrial cancer cells and OVCAR-3 ovarian cancer cells were cultured as a monolayer in RPMI 1640 medium supplemented with 10% fetal bovine serum, 1% of 2 mM glutamine, and 1% penicillin-streptomycin at 37° C. in a 5% CO2 and 95% humidified atmosphere. MDA-MB231 cells were cultured frozen stock whereas HEC-1B and OVCAR-3 cells were purchased from ATCC.

Fluorescence Microscopy: All the three cells were seeded and allowed to grown into a monolayer in chambered coverglass over 48 hours. The spent medium was replaced with 100 mM concentration of the conjugate either in the presence or absence of an excess of JL-L3 and incubated for 1 h at 37° C. After incubation, the cells were washed three times with fresh medium to remove the unbound fluorescence conjugate. Fresh medium (0.5 ml) was added the cells and the images were acquired by fluorescence microscope (Nikon 90i).

Binding Assay: 100,000 MCF7 cells were seeded into 24 well plate and allowed to grow into monolayer over 48 h. Spent medium was replaced with the fresh medium containing various concentrations of the dye conjugate with either in the presence or absence of an excess of the unlabeled ligand. After incubation for 1 h at 37° C., the cells were washed three times with the fresh medium and dissolved in 0.5% SDS. The fluorescence was measured using a fluorimeter. All final conjugates were purified by HPLC prior to its use in in-vitro and in vivo studies.

Figure 9:
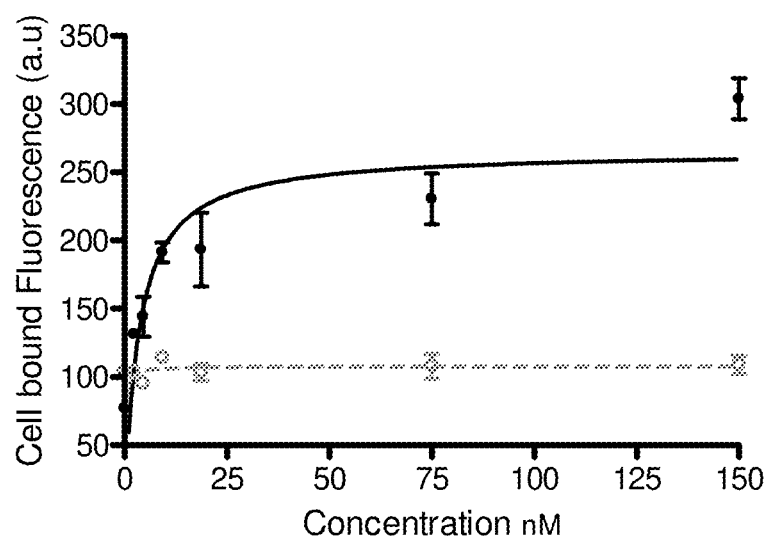
FIG. 9 shows in vitro binding of JL-L3-S0456 for MDA-MB231 breast cancer cells expressing LHRH-R as determined by fluorescence vs. concentration.

In vitro binding affinity: The binding affinity of the fluorescence conjugate (JL-L3-S0456) was determined on the breast cancer cells MDA-MB231. The results of the assay are shown in FIG. 9. The cells were exposed to various concentrations of the NIR dye conjugate (JL-L3-S0456) and the apparent Kd was determined by measuring the cell bound fluorescence. The cells were incubated with to various concentration of the dye conjugate either in the presence or absence of 100-fold excess of the unlabeled conjugate at 37° C. for 1 h. After incubation cells were washed three times and then dissolved in 1% SDS. Cell bound fluorescence was measured by fluorimeter. Apparent $K_d$ of the conjugate was found to be 3.5 nM, whereas the Ki of the parent ligand was reported to be 0.19 nM. This indicates that the introduction of the linker between the ligand and the NIR dye retained the binding affinity of the targeting ligand in the low nanomolar range. The addition of a 100-fold excess of the unlabeled targeting ligand (JL-L3) significantly decreased the cell bound fluorescence intensity of MDA-MB231 with JL-L3-S0456. This confirmed that binding of JL-L3-S0456 to MDA-MB231 cells is receptor-mediated. Therefore, in vitro, JL-L3-S0456 showed low nanomolar binding affinity and specificity for the receptor.

Animal Husbandry: Female athymic nu/nu mice, 5-6 weeks of age were acquired from Harlan Laboratories. The animals were housed in a standard 12 h light-dark cycle and had access to normal rodent chow and water ad libitum. All animal procedures were permitted by the Purdue Animal Care and Use Committee.

In vivo fluorescence imaging and biodistribution. For the development of subcutaneous tumor xenografts, MDA-MB231, OVCAR-3 and HEC-1B 5×10$^6$ cells in 0.2 ml sterile PBS were injected subcutaneously in the right hind flank of the female nu/nu mice. Tumor imaging was initiated once the tumor volume reached between 200 mm$^3$ to 300 mm$^3$. Each tumor-bearing mice was intravenously injected (via tail vein) with the 10 nano moles of fluorescence dye conjugate either in the presence or absence of a 100-fold excess of the unlabeled conjugate. Animals were euthanized two hours post injection using $CO_2$ and the images were acquired using Caliper IVIS Luminal II. After performing the whole body image, the organs of interest were harvested and imaged to inspect the accumulation of the fluorescence in these organs. The image acquisition parameters were as follows: i) lamp level-high, ii) excitation-745 nm, iii) emission-ICG, iv) binning (M) 4M, (v) f-stop-4, (vi) FOV-12.5, (vii) acquisition time, 1 s. All final conjugates were purified by HPLC prior to its use in in-vitro and in vivo studies.

To determine the efficiency of the conjugates to target the receptor positive tumor in vivo female nu/nu athymic nude mice were subcutaneously implanted with either MCF7, MDA-MB231, OVCAR3 or HEC-1B. Once the tumor reached an appropriate volume the mice were injected intravenously with the dye conjugates (10 nmoles) either in the presence or absence of the excess of the unlabeled targeting molecule. Mice were imaged 2 h post injection to investigate the accumulation of the dye conjugates in tumor and other vital organs.

Figure 10A:
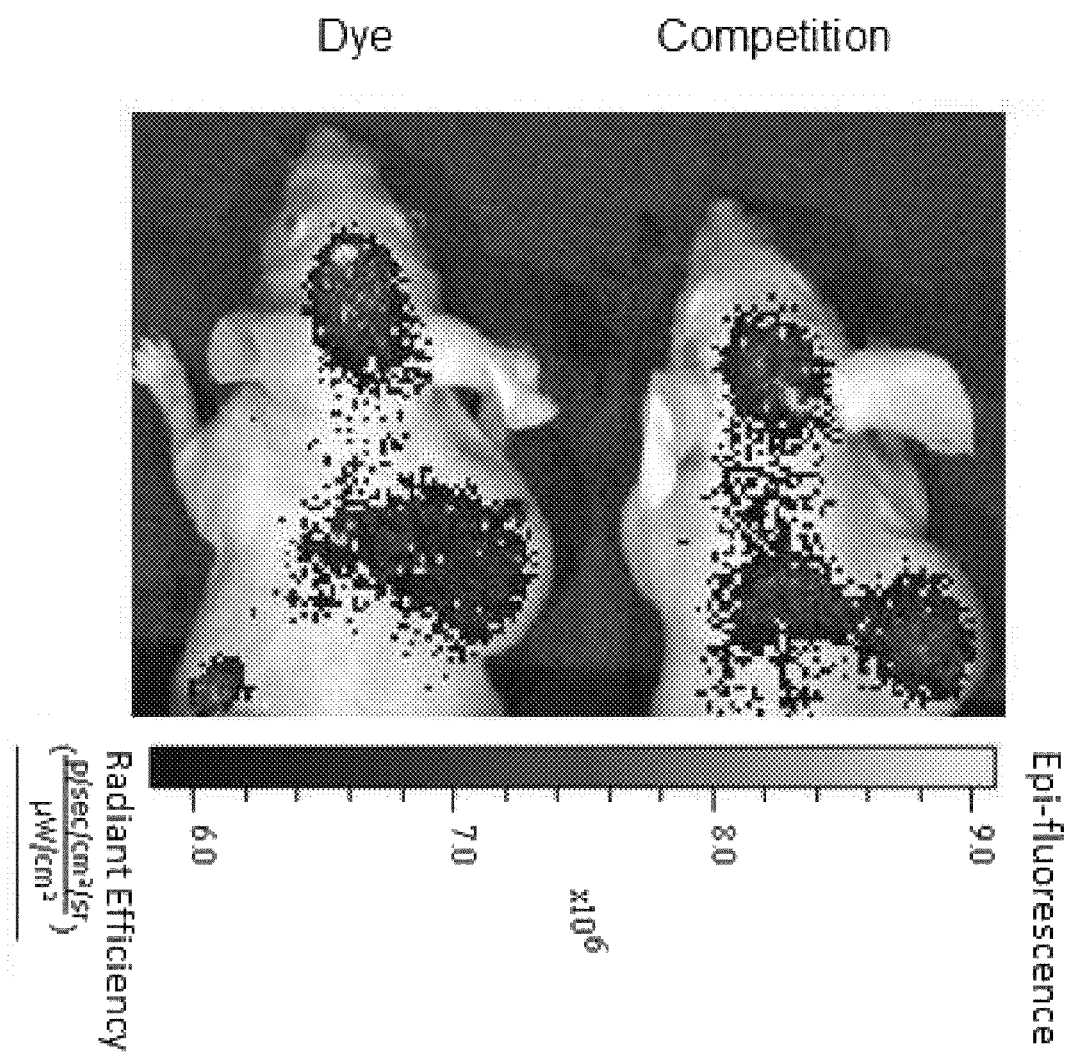
FIG. 10A shows in vivo uptake of the JL-L1-S0456 dye conjugate in MCF-7 tumor xenografts.
Figure 10B:
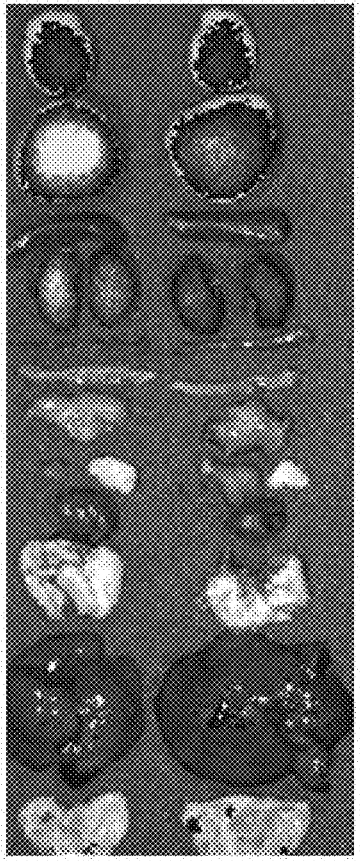
FIG. 10B shows uptake of JL-L1-S0456 by various organs excised from the mice shown in FIG. 10A.
Figure 10B:
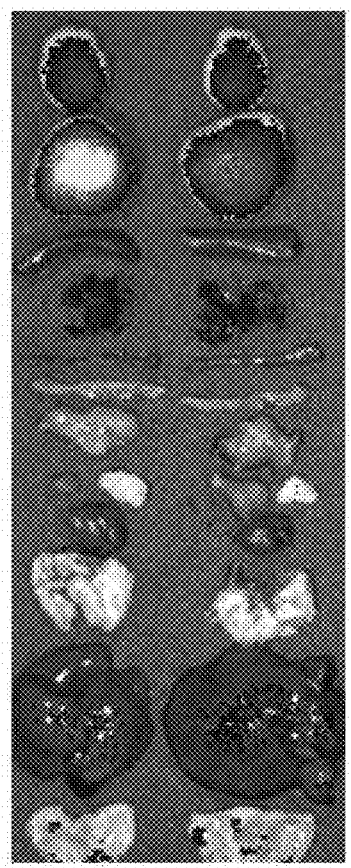
Figure 10B:

FIG. 10A shows in vivo uptake of the JL-L1-S0456 dye conjugate in MCF-7 tumor xenografts. Mice were treated intravenously with the dye conjugate either in the presence or absence of 100-fold excess of the unlabeled conjugates. FIG. 10B shows uptake of JL-L1-S0456 by various organs. All the images were acquired 2 h post injection. List of organs from top to bottom: Brain, tumor, spleen, kidney, small intestine, large intestine, muscle, skin, heart, lungs, liver and stomach.

JL-L1-S0456 dye conjugate did not show any uptake in the tumor or any other organs when excited at 745 nm but upon excitation, at 640 nm the fluorescence was found to be accumulated primarily in the tumor, kidney, and brain which was found to be noncompeting. Without intending to be bound by theory, two reasons were hypothesized for this unexpected behavior of JL-L1-S0456. Under suitable conditions, primary amine can displace the hydroxyl oxygen of the phenolic group of the dye to form a C—N bond between the dye and rest of the molecule. This replacement can result in shifting the excitation of the dye from 745 nm to 640 nm.

Figure 11A:
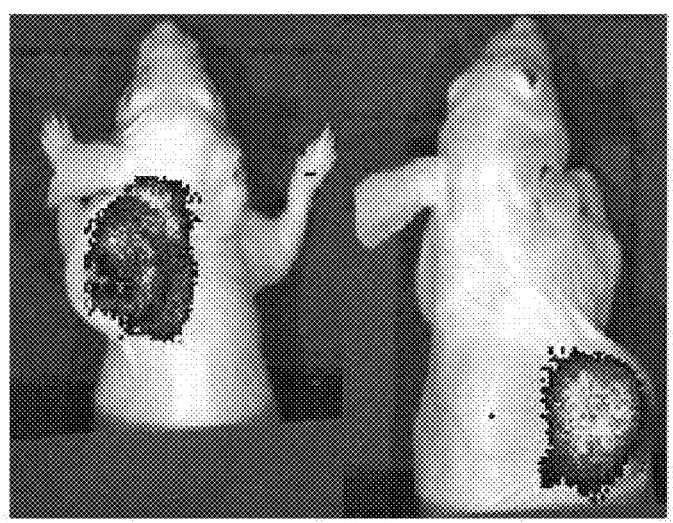
FIG. 11A shows in vivo uptake of the JL-L2-S0456 dye conjugate in MDA-MB231 tumor xenografts.
Figure 11B:
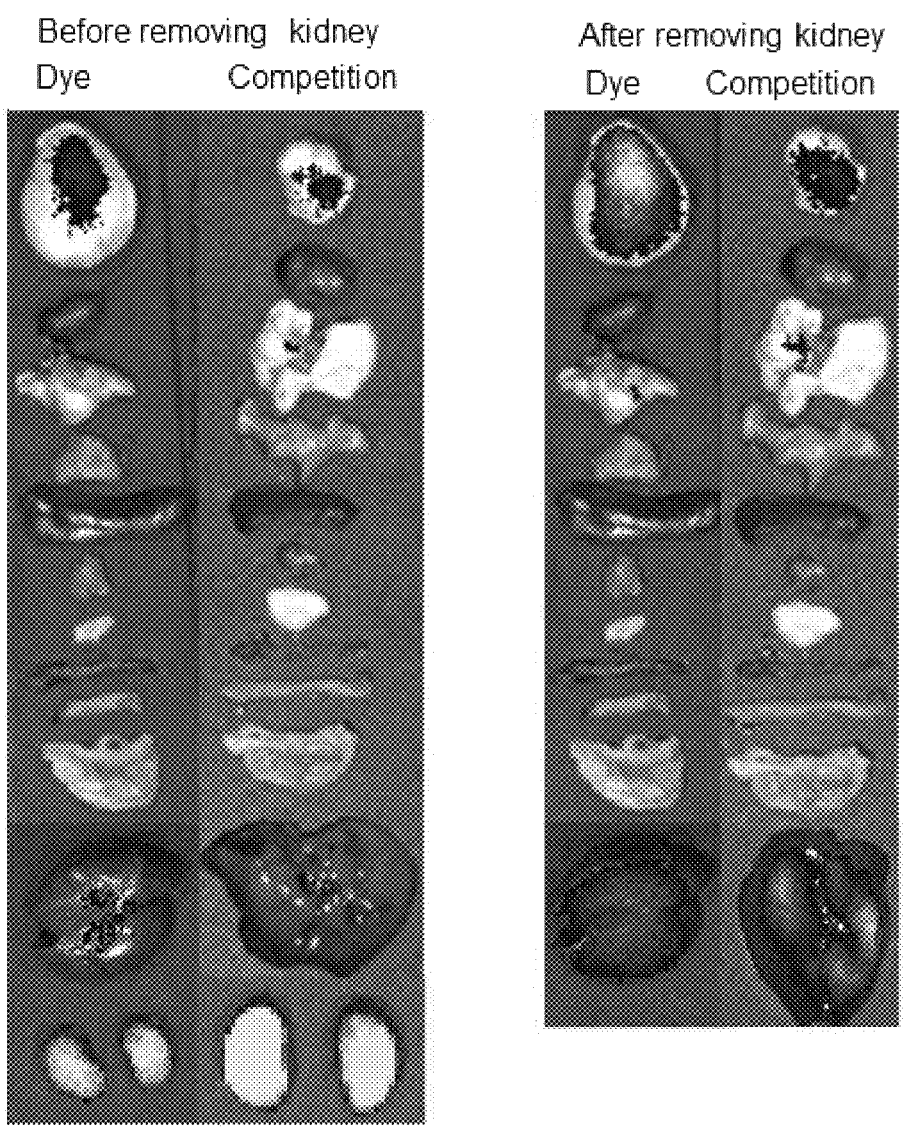
FIG. 11B shows uptake of JL-L2-S0456 by various organs excised from the mice shown in FIG. 11A.

FIG. 11A shows in vivo uptake of the JL-L2-S0456 dye conjugate in MDA-MB231 tumor xenografts. Mice were treated intravenously with the dye conjugate either in the presence or absence of 100-fold excess of the unlabeled conjugates. FIG. 11B shows uptake of JL-L2-S0456 by various organs. All the images were acquired 2 h post injection. List of organs from top to bottom: Tumor, heart, lungs, pancreas, spleen, muscle, skin, small intestine, large intestine, stomach, liver, and kidney.

When tested in vivo JL-L2-S0456 showed receptor-mediated uptake in the breast cancer tumors. Non-specific kidney and liver uptake were also observed. Without intending to be bound by theory, since liver and kidney plays a vital role in excretion, the fluorescence in these organs was due to the clearance of the dye conjugate via the renal and hepatic route.

Figure 12A:
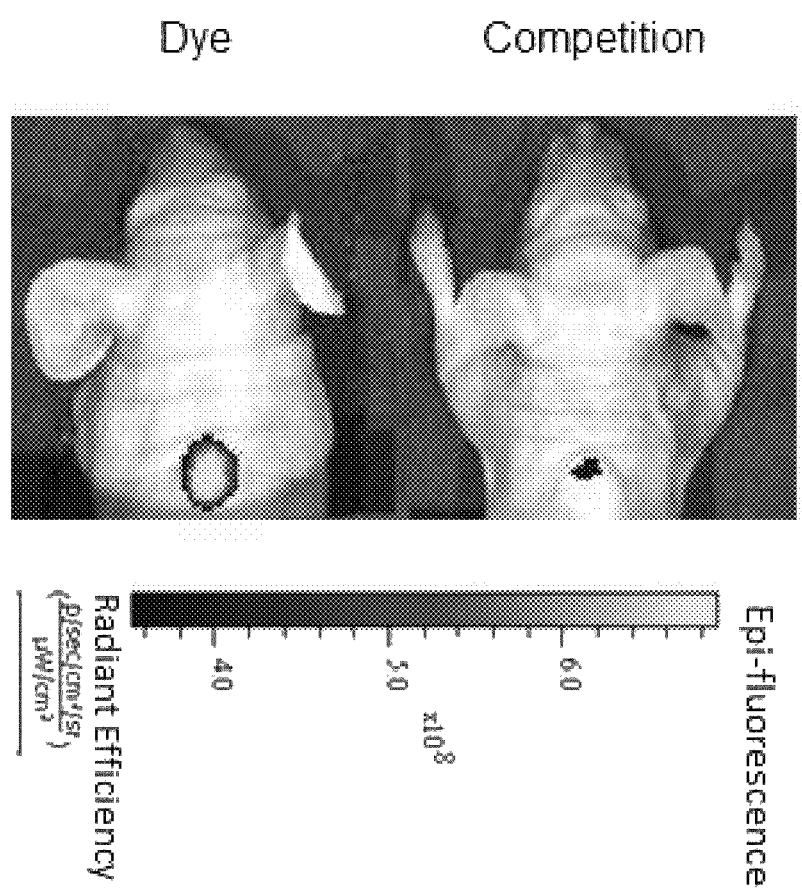
FIG. 12A shows in vivo uptake of the JL-L3-S0456 dye conjugate in MDA-MB231 tumor xenografts.
Figure 12B:
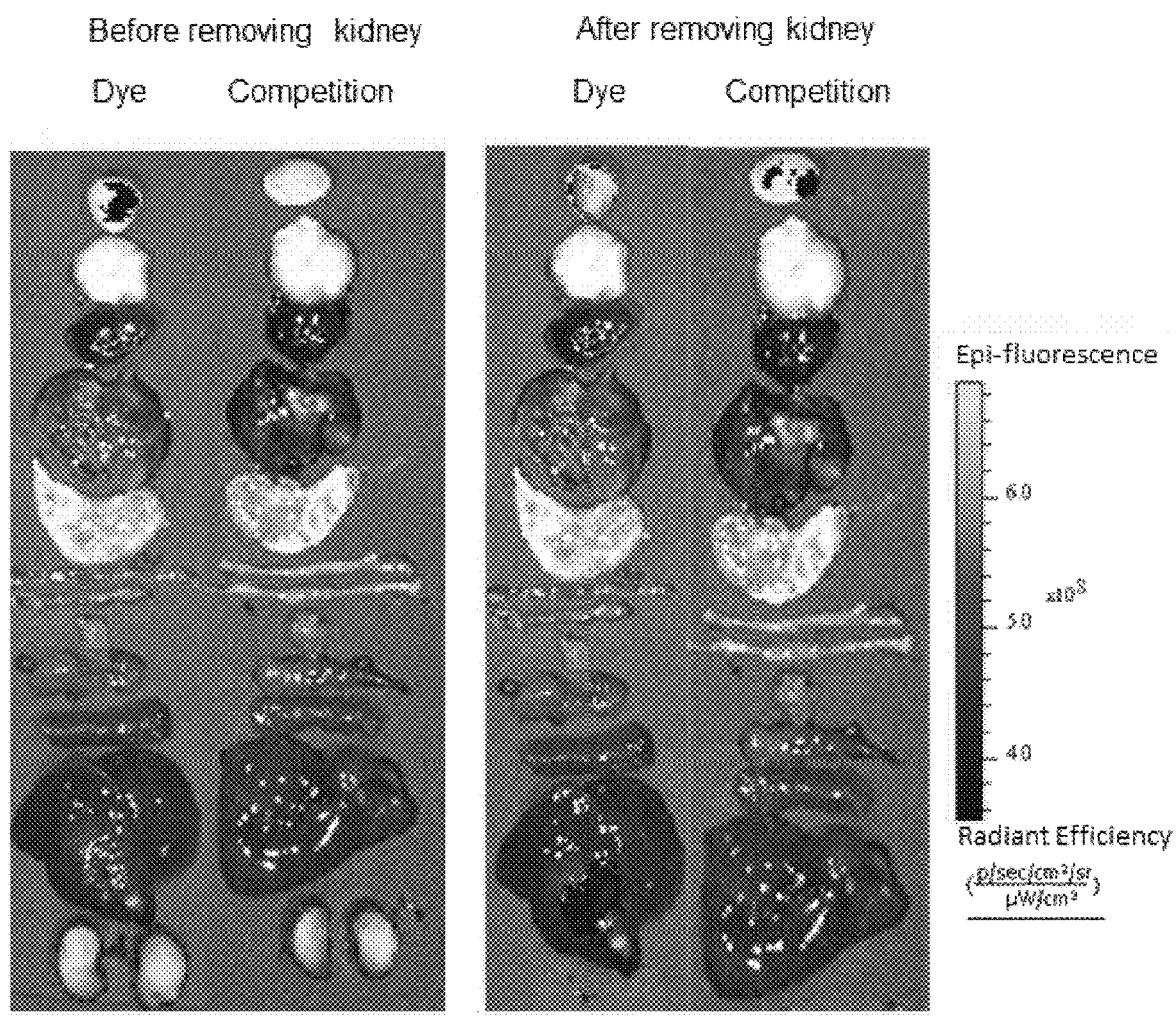
FIG. 12B shows uptake of JL-L3-S0456 by various organs excised from the mice shown in FIG. 12A.

FIG. 12A shows in vivo uptake of the JL-L3-S0456 dye conjugate in MDA-MB231 tumor xenografts. Mice were treated intravenously with the dye conjugate either in the presence or absence of 100-fold excess of the unlabeled conjugates. FIG. 12B shows uptake of JL-L3-S0456 by various organs. All the images were acquired 2 h post injection. List of organs from top to bottom: Tumor, brain, heart, lungs, stomach, small intestine, large intestine, muscle, pancreas, spleen, liver, and kidney.

Figure 13A:
FIG. 13A shows in vivo uptake of the JL-L3-S0456 dye conjugate in HEC-1B tumor xenografts.
Figure 13B:
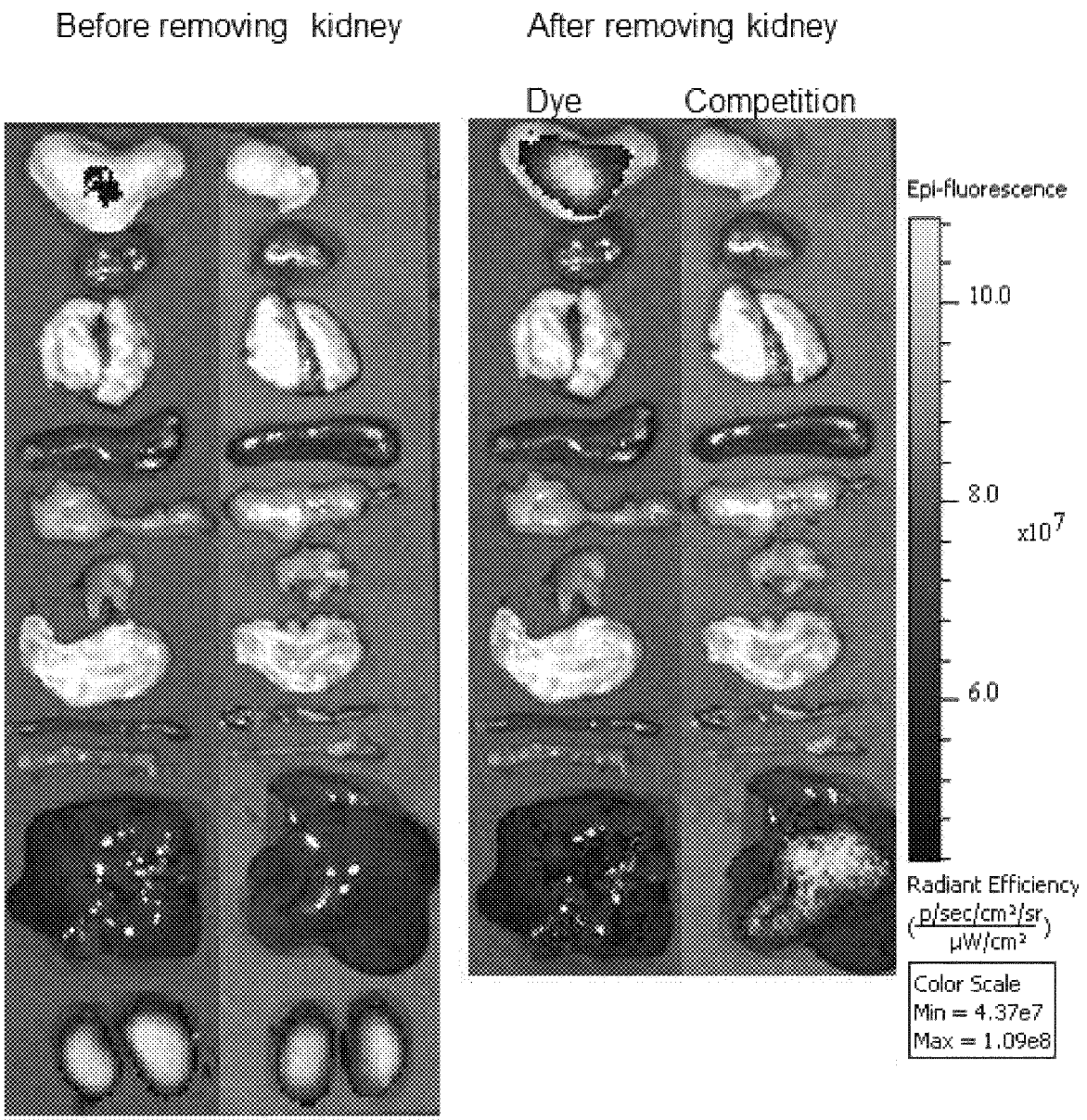
FIG. 13B shows uptake of JL-L3-S0456 by various organs excised from the mice shown in FIG. 13A.

FIG. 13A shows in vivo uptake of the JL-L3-S0456 dye conjugate in HEC-1B tumor xenografts. Mice were treated intravenously with the dye conjugate either in the presence or absence of 100-fold excess of the unlabeled conjugates. FIG. 13B shows uptake of JL-L3-S0456 by various organs. All the images were acquired 2 h post injection. List of organs from top to bottom: Tumor, heart, lungs, spleen, pancreas, muscle, stomach, small intestine, large intestine, liver and kidney.

Figure 14A:
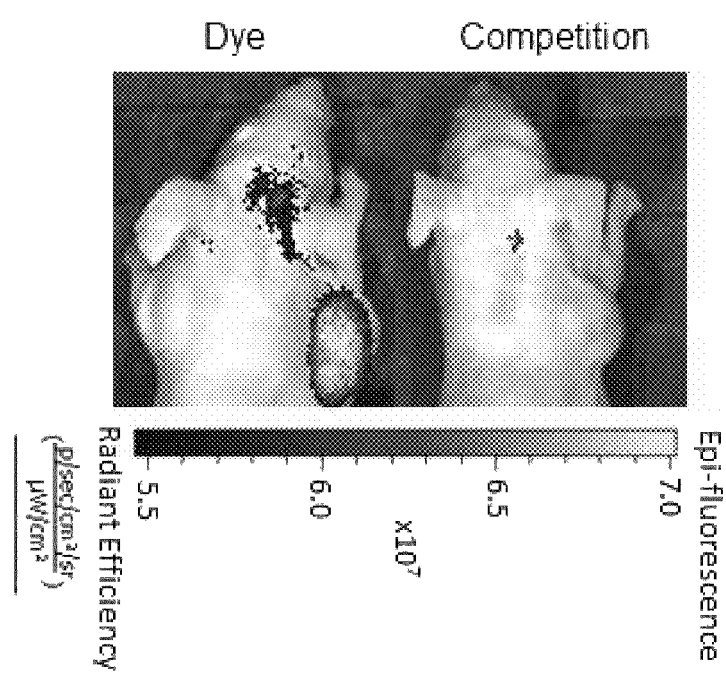
FIG. 14A shows in vivo uptake of the JL-L3-S0456 dye conjugate in OVCAR3 tumor xenografts.
Figure 14B:
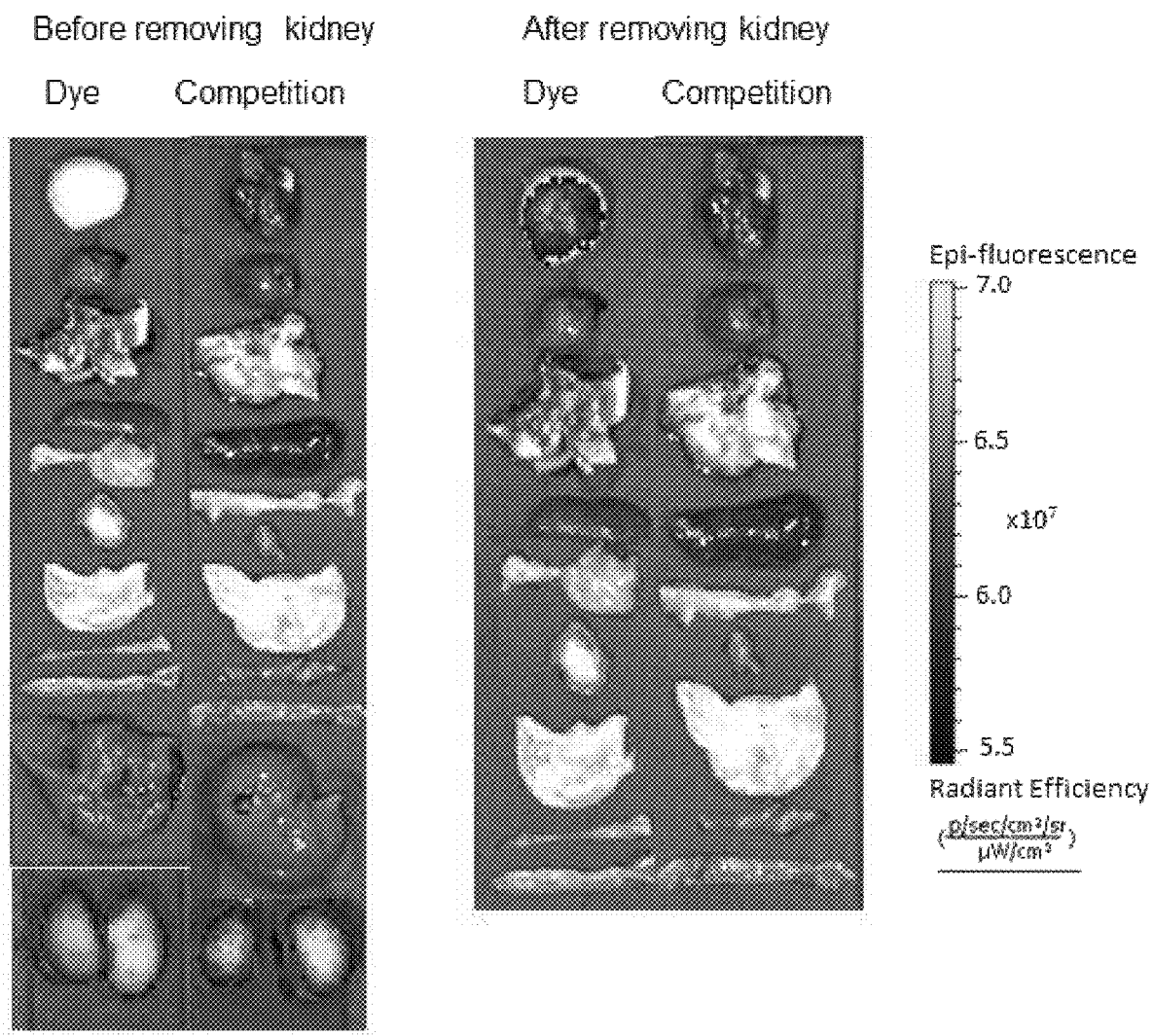
FIG. 14B shows uptake of JL-L3-S0456 by various organs excised from the mice shown in FIG. 14A.

FIG. 14A shows in vivo uptake of the JL-L3-S0456 dye conjugate in OVCAR3 tumor xenografts. Mice were treated intravenously with the dye conjugate either in the presence or absence of 100-fold excess of the unlabeled conjugates. FIG. 14B shows uptake of JL-L3-S0456 by various organs. All the images were acquired 2 h post injection. List of organs from top to bottom: Tumor, heart, lungs, spleen, pancreas, muscle, stomach, small intestine, large intestine, liver, and kidneys.

The PEG linker was further replaced by a linker containing peptidoglycans, JL-L3-S0456. After 2 h post injection, the JL-L3-S0456 was found to be accumulated in the breast cancer tumor. Unlabeled targeting conjugate (JL-L3) was able to compete the tumor uptake of JL-L3-S0456. The bio distribution study showed that other than the tumor, the kidney also exhibited high fluorescence. The fluorescence intensity of the tumor was lower than the kidney but the accumulation of the dye conjugate in tumor was receptor-mediated whereas that of the kidney was due to the excretion of the dye conjugate via renal route. Either none or very minimal fluorescence was observed in the liver.

Time course study. The effectiveness of JL-L3-S0456 to accumulate in the receptor-positive tumors were further inspected by injection the dye conjugate in ovarian cancer and endometrial xenografts. In both these models, JL-L3-S0456 showed receptor-mediated uptake and was found to excrete through renal route. Other than tumor and kidney other organs showed little to no signal. To investigate the retention time of the dye conjugate in the tumor a time-course study was performed. Mice were injected with 10 nmoles of the dye conjugates and imaged at 2 h, 8 h, and 12 h. Even after 12 h post injection, the fluorescence intensity of the tumor was found to be high and only a very slight decrease in the intensity was observed when compared to the image taken 2 h post injection.

Figure 15A:
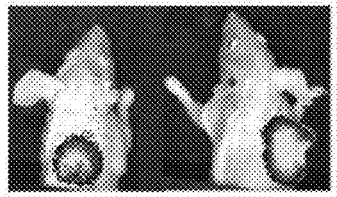
FIG. 15A shows in vivo uptake of the JL-L3-S0456 dye conjugate in MDA-MB231 tumor xenografts 2 h post injection.
Figure 15B:
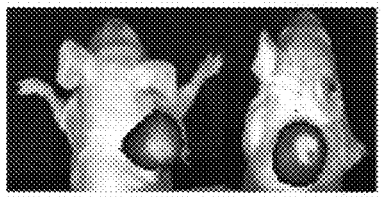
FIG. 15B shows in vivo uptake of the JL-L3-S0456 dye conjugate in MDA-MB231 tumor xenografts 8 h post injection.
Figure 15C:
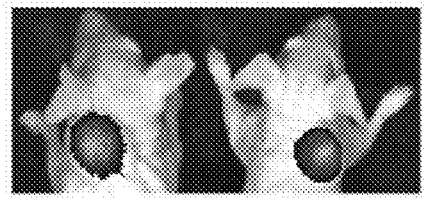
FIG. 15C shows in vivo uptake of the JL-L3-S0456 dye conjugate in MDA-MB231 tumor xenografts 12 h post injection.
Figure 15D:
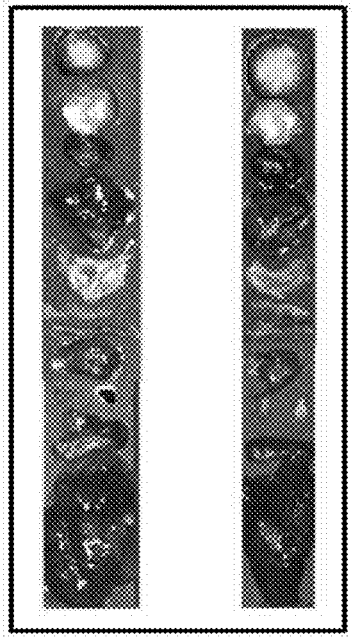
FIG. 15D shows uptake of JL-L3-S0456 by various organs excised from the mice shown in FIG. 15A.
Figure 15E:
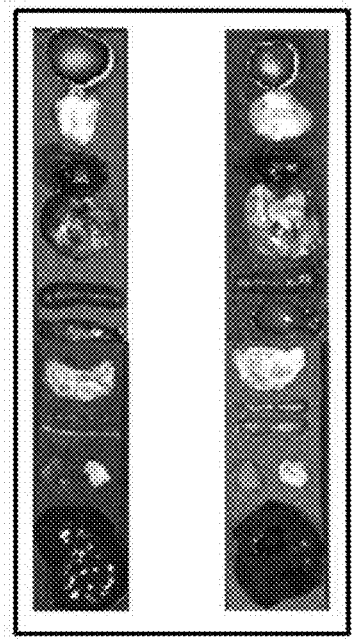
FIG. 15E shows uptake of JL-L3-S0456 by various organs excised from the mice shown in FIG. 15B.
Figure 15F:
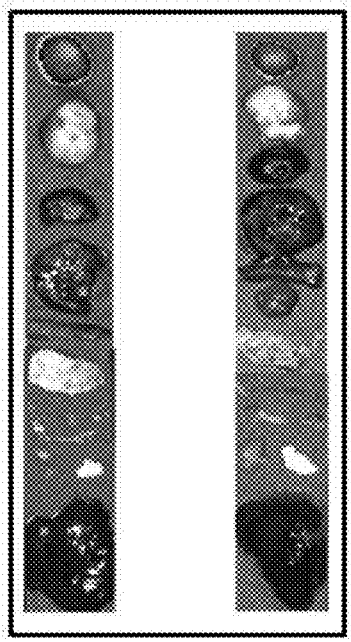
FIG. 15F shows uptake of JL-L3-S0456 by various organs excised from the mice shown in FIG. 15C.

Results of time course imaging of MDA-MB231 tumor with JL-L3-S0456 are shown in FIG. 15A. The images were taken at 2 h, 8 h, 12 h and 24 h post injection to study the tumor retention of the dye conjugate. FIG. 15B shows uptake of JL-L3-S0456 by various organs was observed at various time points. List of organs from top to bottom: Tumor, brain, heart, lungs, stomach, small intestine, large intestine, spleen, pancreas, muscle, skin, and liver.

The dye conjugate showed receptor mediated uptake in the tumor whereas the uptake in the kidney was not receptor-mediated and was due to excretion of the conjugate via renal route. In addition, NIR dye also has higher tissue penetration which can further assist effective resection of the tumor mass. Overall the in vivo results in the mouse models support that JR-L3-S0456 for fluorescence guided surgery in humans to dissect the cancer cells expressing the LHRH-R.

The conjugate was further evaluated the tumor targeting efficiency of the radioactive conjugate in vivo in human triple negative breast cancer xenografts.

Method Example 2. JL-L1A, JL-L2A, JL-L3A

Cell Culture. Breast cancer MDA-MB231 cells were grown as a monolayer in a RPMI medium supplemented with 10% fetal bovine serum, 1% penicillin-streptomycin and 2 mm 1% Glutamine. Cells were kept at 37° C. in a 5% $CO_2$ and 95% air-humidified atmosphere.

Animal Husbandry and in vivo tumor implantation. Female athymic nu/nu mice were purchased from Harlan laboratories. The animals were housed in a sterile environment and kept in 12 h light/day cycle. The animals have free access to rodent chow and water. $2 \times 10^6$ MDA-MB23 cells were suspended in 100 microliters of sterile phosphate buffer saline and injected subcutaneously into the right flank of each mouse.

Figure 16:
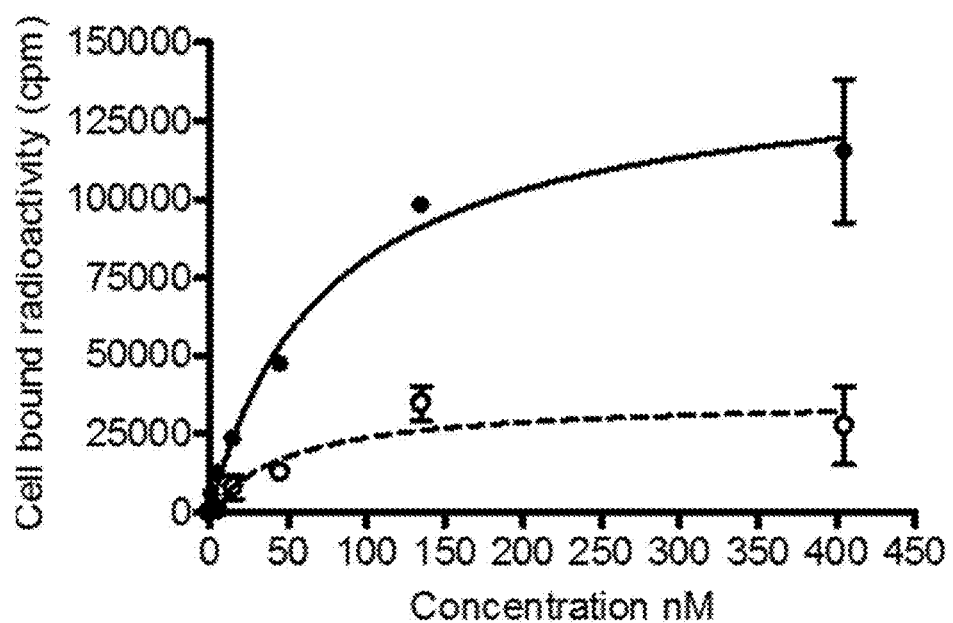
FIG. 16 shows in vitro binding of JL-L3A to MDA-MB231 breast cancer cells expressing LHRH-R as determined by radioactivity vs. concentration.

In vitro binding assay. MDA-MB231 cells were seeded in 24 well plate and allowed to form a monolayer. The spent medium was replaced with serum free medium containing various concentrations of the radioactive conjugate (JL-L1A or JL-L2A, or JL-L3A) either in the presence or absence of excess of the unlabeled conjugates. The cells were incubated for 2 h at 37° C. and then rinsed three times with medium. After rinsing cells were dissolved by adding 0.5 ml of 0.25N NaOH to each well for 20 minutes. The cell bound radioactivity measured by using Packcard gamma counter and the $K_d$ was calculated using the graphpad prism by plotting the cell bound radioactivity against the concentration of radiotracer. As show in FIG. 16, MDA-MB231 cells were incubated with various concentrations of the radioactive conjugate either in the presence or absence of the excess of the unlabeled conjugate. Solid circle indicates $^{99m}Tc$ chelated conjugates whereas open circle indicates competition.

In vivo imaging and biodistribution. All the animal experiments were conducted in accordance to the guidelines approved by Purdue Animal Care and Use Committee. The experiment was initiated once the tumor volume reached approximately 300-400 $mm^3$. Tumor volume was measured as $0.5 \times L \times W_2$, where L is the longest axis and W is an axis perpendicular to L in mm. In the lateral tail vein, the mice were injected with 150 µCi of the radioactive conjugates (either in the presence or absence of excess of the unlabeled conjugates.) in 100 µl of sterile phosphate buffer saline For imaging mice were euthanized 2 h post injection by $CO_2$ asphyxiation and imaged using Kodak Imaging Station. After imaging necroscopy was performed on animals to remove selected tissue and weighted. Tissue bound radioactivity was quantified by using gamma counter (Packard Gamma Counter) For time course study, the animals were sacrificed at following time points post injections: 2 h, 4 h, 6 h, and 8 h. Tissue of interest was weighed and the tissue bound radioactivity was counted by using gamma counter. Count per minute values of tissues bound radioactivity was decay corrected and converted into percentage injected dose per gram if the tissue (% ID/g). The data was analyzed by using GraphPad Prism.

Without intending to be bound by theory, all the three linkers contributed to i) the hydrophilicity and solubility of the final compounds ii) to diminish the non-specific passive diffusion of the conjugates in to the cells lacking the targeting receptor. iii) prevent the interference of the $^{99m}Tc$ chelating group with the binding of the targeting ligand. All the three conjugates showed more than 95% chelation efficiency.

To determine the binding affinity, the MDA-MB231 cells were incubated with various concentrations of the radioactive conjugate JL-L1A either in the presence or absence of the unlabeled conjugate for 2 h at 37° C. The conjugate JL-L3A displayed low nanomolar binding affinity for LHRH-R ($K_d$=14.39 nM). This indicated that as a result of conjugation to a spacer the binding affinity of the parent compound ($K_i$=0.4 nM) was not intensely effected and was still maintained in the low nanomolar range. Without intending to be bound by theory, in the presence of the excess of competing ligand the cell-bound radioactivity diminished which suggest that binding of JL-L3A to MDA-MB231 cell is receptor mediated.

Figure 17A:
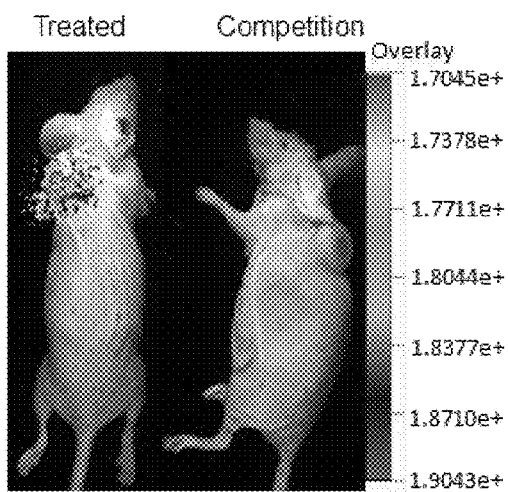
FIG. 17A shows in vivo uptake of JL-L1A in treated and competition mice.
Figure 17B:
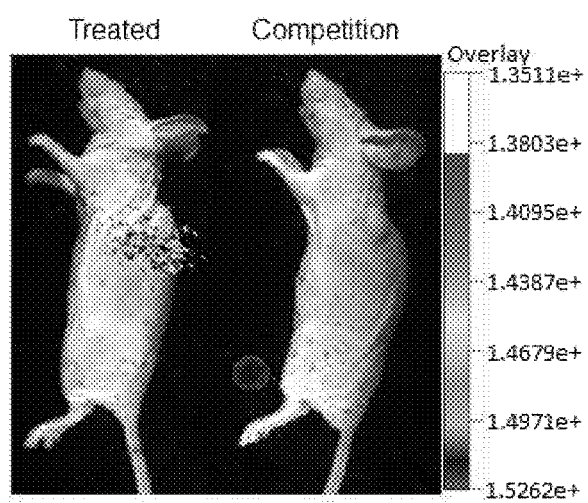
FIG. 17B shows in vivo uptake of JL-L2A in treated and competition mice.
Figure 17C:
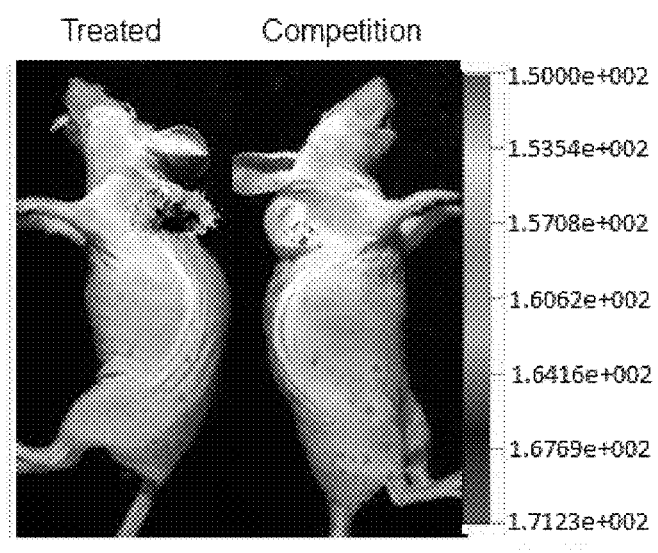
FIG. 17C shows in vivo uptake of JL-L3A in treated and competition mice.

In vivo whole body imaging and biodistribution of JL-L1A, JL-L2A and JL-L3A. In order to investigate the uptake of radioactive conjugates in LHRH-R positive tumors all the three conjugates (150 µCi) were injected the lateral vein of mice with MDA-MB231 tumors. For competition studies the mice were additional injected with 100-fold excess of the unlabeled conjugates. MDA-MB231 tumor bearing mice were injected with the $^{99m}Tc$ chelated conjugates in their lateral tail vein (mice labeled as treated). Another group of mice were injected with the $^{99m}Tc$ labeled molecules but in the presence of excess of the unlabeled conjugates. Images were taken 2 h post injections. FIG. 17A represents whole body imaging of JL-L1A whereas FIG. 17B and FIG. 17C represents the whole body imaging of JL-L2A and JL-L3A respectively. (n=5). All the three radioactive conjugates showed receptor mediated uptake in the tumor. JL-L1A showed highest uptake in the tumor but also showed uptake in other vital organs. On the contrary JL-L2A and JL-L3A showed highest uptake in the kidney but this was not competed by the coadministration of the unlabeled conjugate. The non-specific uptake in the kidney and liver uptake of the conjugates suggested the elimination of the molecules via the renal and hepatic route. In addition to kidney, liver and tumor, JL-L2A also showed significant non-specific uptake in the spleen but only minimal activity was observed with administration of JL-L3A.

Figure 18A:
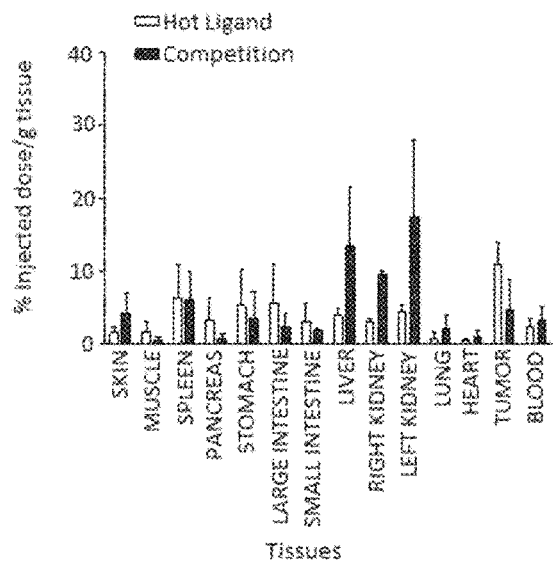
FIG. 18A shows in vivo biodistribution of JL-L1A in MDA-MB231 tumor xenografts 2 h and 4 h post injection.
Figure 18B:
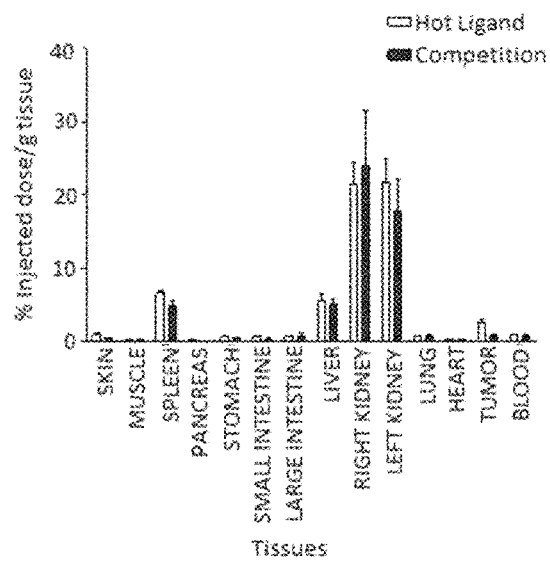
FIG. 18B shows in vivo biodistribution of JL-L2A in MDA-MB231 tumor xenografts 2 h and 4 h post injection.
Figure 18C:
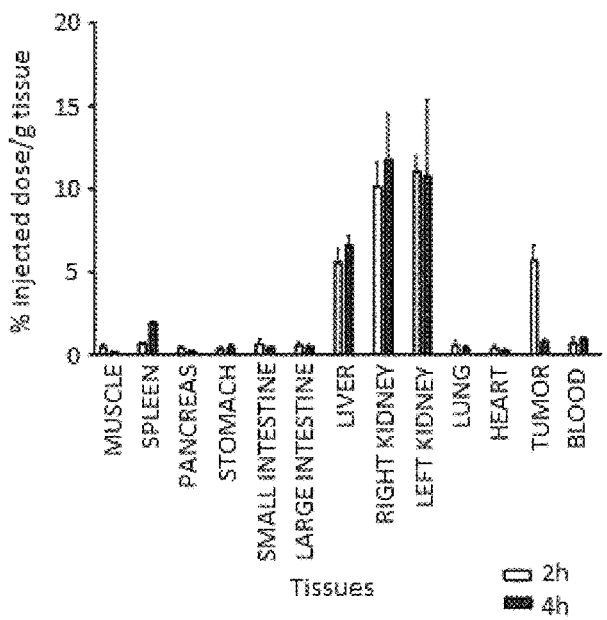
FIG. 18C shows in vivo biodistribution of JL-L3A in MDA-MB231 tumor xenografts 2 h and 4 h post injection.

The further investigate the retention of 99mTc chelated JL-L3A, the radioactive conjugate was injected in mice with MDA-MB231 xenografts. After euthanizing the. Animals at 2 h, 4 h and 8 h post injection they were imaged and radioactivity associated with organs of interest was counted. The time-dependent imaging showed that 8 h post-injection radioactivity intensity of the tumor reduced to less than half of the intensity at 2 h post-injection. Time dependent biodistribution at 4 h was similar to the biodistribution 2 h post injection as shown in FIG. 18. MDA-MB231 tumor bearing mice were injected with the $^{99m}Tc$ chelated conjugates in their lateral tail vein (mice labeled as treated). Another group of mice were injected with the $^{99m}Tc$ labeled molecules but in the presence of excess of the unlabeled conjugates. Radioactivity of all the major organs and blood were determined 2 h post injection and the percentage injected dose per gram of the tissue was plotted. FIG. 18A represents biodistribution of JL-L1A whereas FIG. 18B and FIG. 18C represents the biodistribution of JL-L2A and JL-L3A respectively (n=5). Error bar indicates standard deviation.

Figure 19A:
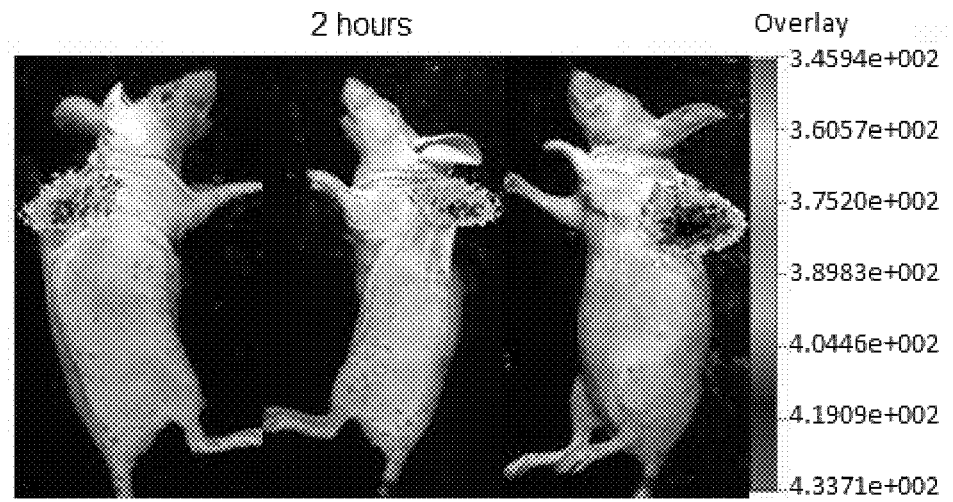
FIG. 19A shows in vivo uptake of the JL-L1A conjugate in MDA-MB231 tumor xenografts 2 h post injection.
Figure 19B:
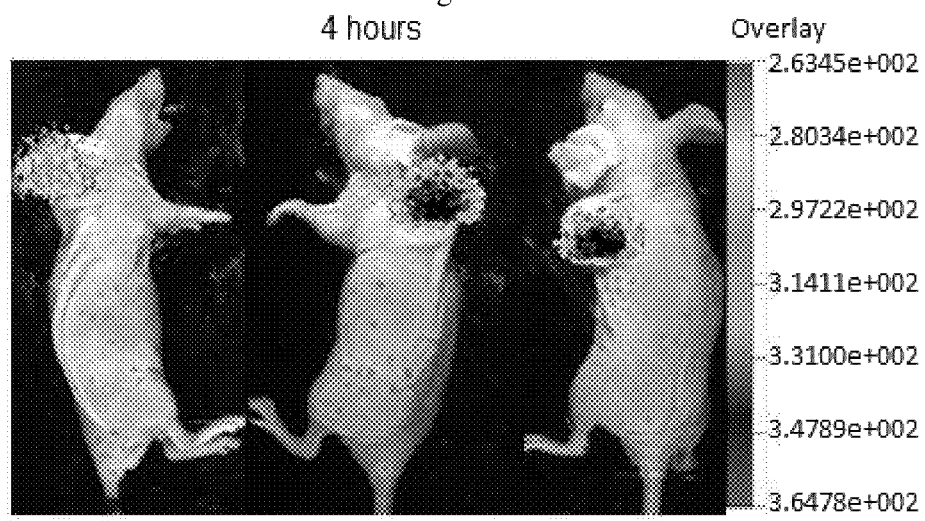
FIG. 19B shows in vivo uptake of the JL-L2A conjugate in MDA-MB231 tumor xenografts 4 h post injection.
Figure 19C:
FIG. 19C shows in vivo uptake of the JL-L3A conjugate in MDA-MB231 tumor xenografts 8 h post injection.
Figure 19D:
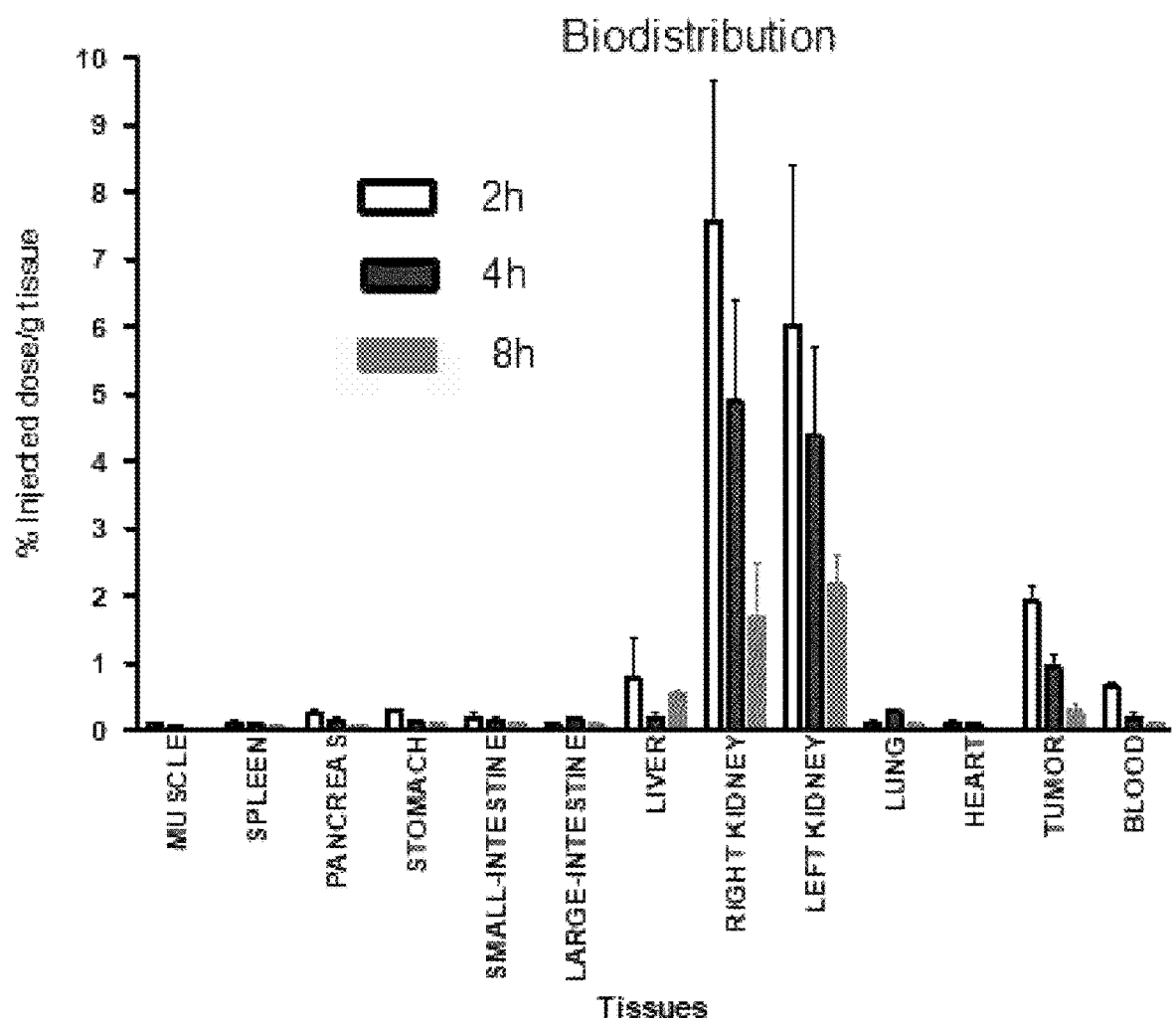
FIG. 19D shows the percentage injected dose/g tissue for the respective organs are 2 h, 4 h, and 8 h.

FIGS. 19A, B, and C show in vivo whole body imaging and biodistribution of JL-L1A at 2 h, 4 h and 8 h post injection, respectively. The mice bearing a MDA-MB231 tumor were injected with 150 µCi of 99mTc chelated JL-L1A via tail vein injection. Mice were euthanized 2 h, 4 h and 8 h post injection and imaged. For biodistribution, the organs of interest were dissected and radioactivity was counted using gamma scintillation counter. As shown in FIG. 19D percentage injected dose/g of tissue was plotted against respective organs. The error bar indicates standard deviation.

A time-dependent decrease in radioactivity was observed in all the organs. All the three conjugates exhibited receptor-mediated accumulation in the tumor but JL-L3A displayed the most favorable biodistributions 2 h post injected. Tissue distribution of JL-L3A at 4 h and 8 h post injection showed the same pattern as 2 h post injection. The kidney and liver uptake of the conjugate were non-specific and were a result of the renal and hepatic clearance of the molecule. JL-L3A possess superior chemical stability, ease of synthesis and site-specific radiolabeling properties when compared to the LHRH-R targeting peptides.

Method Example 3. JL-L2-Rhodamine, JR-L3, JR-L3-TubBH

Confocal microscopy: 50,000 MDA-MB231 and SKVO3 human cancer cells were seeded into each well of chambered coverglass plates and allowed to grow to confluence over 48 h. Spent medium was replaced ith 0.5 mL of FBS fresh medium and incubated with 100 nM of rhodamine dye conjugate (JL-L2-Rhodamine) either in the presence or absence of 100-fold excess of JL-L2. After incubation for 1 h the cells were washed with incubation solution for three times and then replaced with 0.5 ml of culture medium. Images were acquired using Olympus confocal microscopy.

In vitro determination of cell viability. MDA-MB231 and SKVO3 cells were seeded at a concentration of 10,000 cells per well on a 24 well plate and allowed to grow in monolayers. The spent medium is removed and the cells were incubated with various concentrations of JL-L3-TubBH either in the presence or absence of 100-fold excess of JL-L3 in FBS free medium. After incubating for 2 h at 37° C., cells were rinsed three times with fresh medium and then incubated in 0.5 ml fresh medium for an additional 66 h at 37° C. Sent medium was then replaced with 0.5 ml of medium containing $^3$H-thymidine and incubated for additional 4 h. Cells were then again washed three times with the fresh medium and then incubated with 0.5 ml of 2.5% trichloroacetic acid for 10 min at room temperature. After removing the trichloroacetic acid, cells were dissolved in 0.25 N NaOH. Cell viability was determined by counting the incorporation of $^3$H-thymidine in cells using scintillation counter (Packard, Packard Instrument Company). The $IC_{50}$ value was derived from a plot of the percent of $^3$H-thymidine incorporation versus log concentration using Graph Pad Prism 4.

Animal Husbandry: Athymic nu/nu mice were purchased from Harlan Laboratories. Mice were housed in a sterile environment on a standard 12-hour light-dark cycle and maintained on normal rodent chow. All animal procedures were approved by the Purdue Animal Care and Use Committee in accordance with National Institutes of Health guidelines.

Tumor model and therapy: 5-6 weeks old female nu/nu athymic nude mice were subcutaneously injected with 5.0× $10^6$ breast cancer cells MDA-MB231 and ovarian cancer cells SKVO3 into their shoulders. Tumors were measured in two perpendicular directions 3 times per week with Vernier calipers, and their volumes were calculated as $0.5×L×W^2$, where L is the longest axis (in millimeters), and W is the axis perpendicular to L (in millimeters). Treatment was initiated once the tumor volume reached ~100 mm³. Dosing solutions were prepared in sterile saline and injected intravenously. Each mouse received 2 μmol/kg of JL-L3-TubBH either in the presence or absence of 100-fold excess of JL-L3 or saline. Mice were administered with the test agents 3 times per week for 3 weeks and as a measure of gross toxicity mice were simultaneously weighed at each dosing.

Binding and Internalization of rhodamine dye conjugate: LHRH-R targeted rhodamine conjugate was tested in MDA-MB231 and SKVO3 cells to evaluate the binding and internalization of the dye conjugate. For this, the cancer cells were incubated for 1 h with various concentration of the rhodamine dye conjugate (JL-L2-Rhodamine) either in the presence or absence of excess of JL-L2. After washing off the excess dye conjugate, the cells were examined by confocal microscopy.

Figure 20:
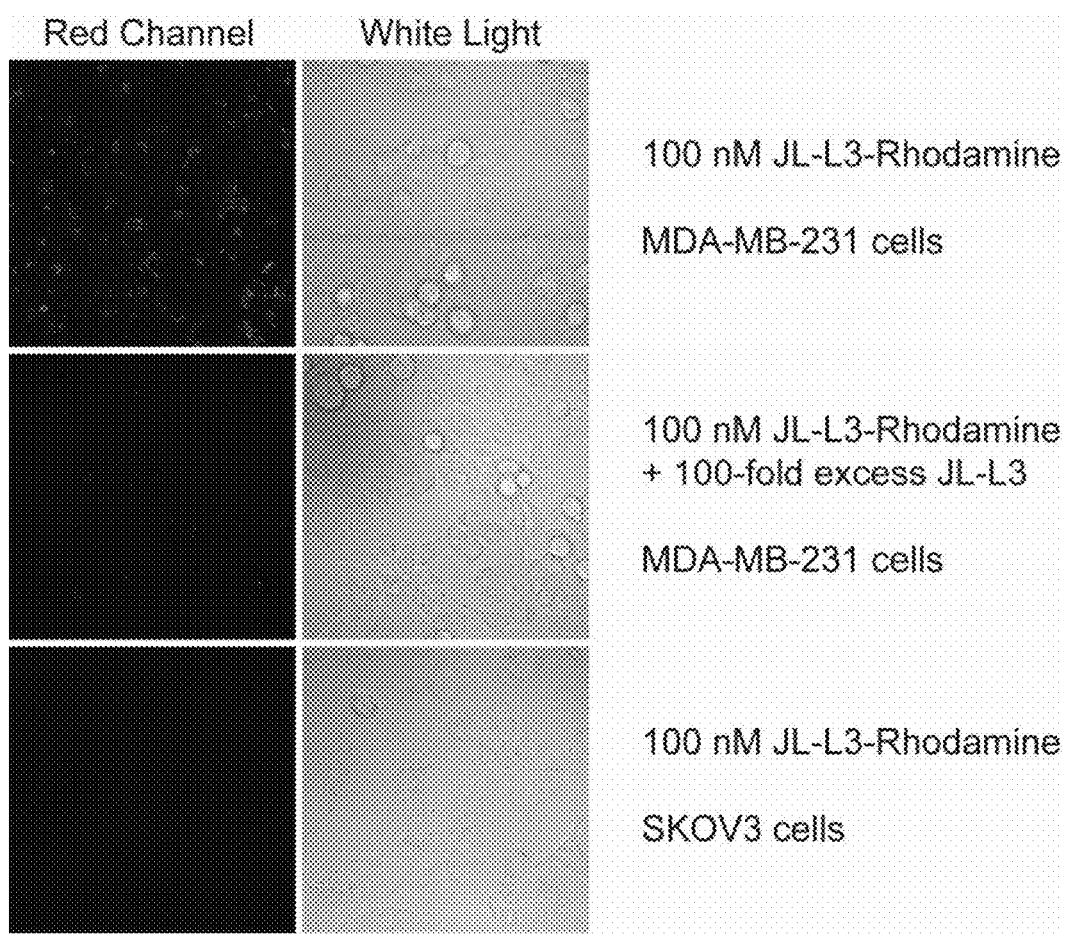
FIG. 20 shows confocal imaging showing in vitro binding of JL-L3-Rhodamine conjugate to MDA-MB-231 (receptor positive) and SKVO3 (receptor negative) cells.

Cells were incubated with 100 nM of the JL-L3-Rhodamine for in the presence or absence of 100-fold excess of JL-L3. After 1 h the cells were washed three times and the white light and fluorescence images were taken by using the confocal microscope. Rhodamine conjugate was observed to be present in both inside and on the surface of the cells in MDA-MB231 cells whereas no uptake was observed in SKOV3 cells, as shown in FIG. 20.

Figure 21A:
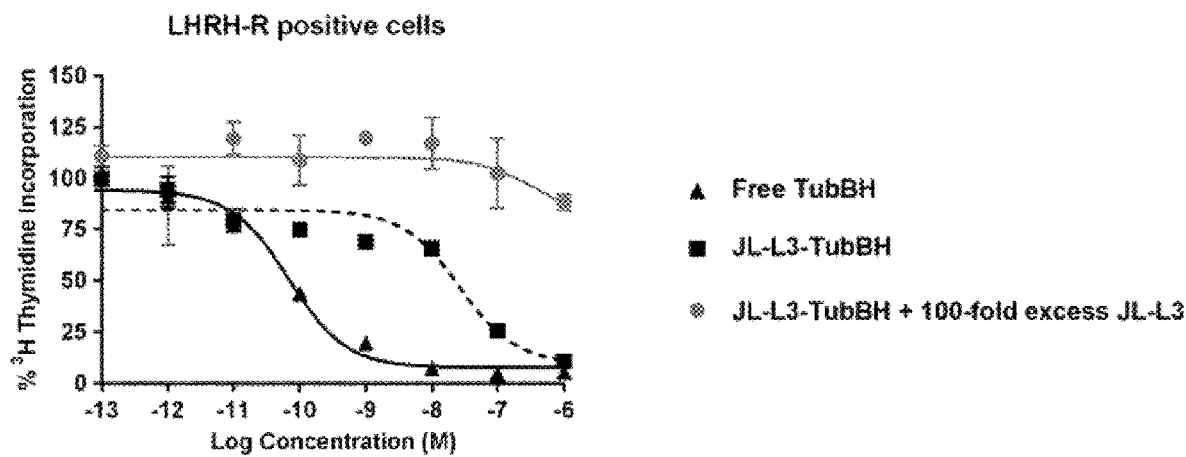
FIG. 21A shows in vitro binding of TubBH and JL-L3-TubBH to LHRH-R positive cells (MDA-MB-231) JL-L3-S0456 as determined by $^3$H thymidine incorporation vs. concentration.
Figure 21B:
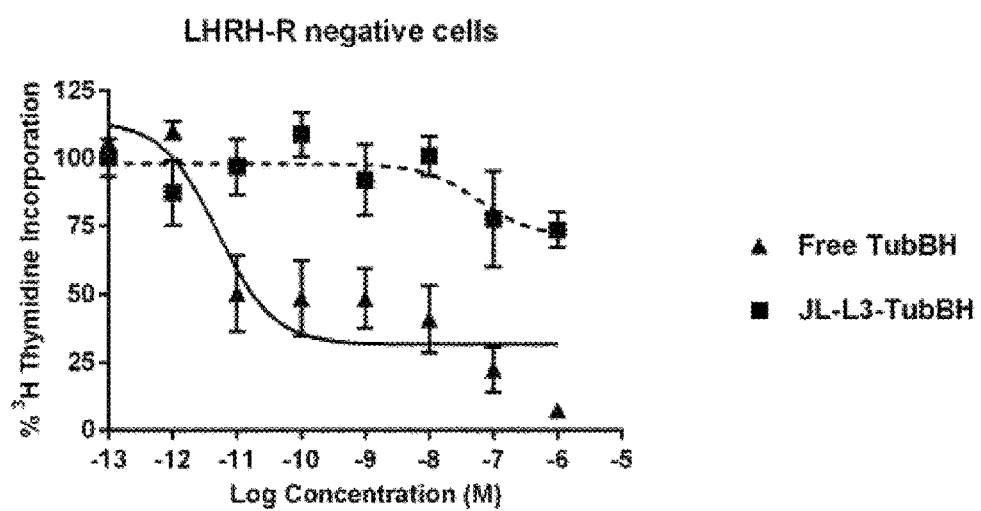
FIG. 21B shows in vitro binding of TubBH and JL-L3-TubBH to LHRH-R negative cells (SKOV3) JL-L3-S0456 as determined by $^3$H thymidine incorporation vs. concentration.

In vitro cytotoxicity of tubulysin B hydrazide conjugate: To inspect the killing efficiency of the therapeutic conjugate, MDA-MB231 and SKOV3 cancer cells were incubated with various concentrations of JL-L3-TubBH either in the presence or absence of excess JL-L3, for 2 h at 37° C. After washing off the excess conjugate, the cells were incubated in fresh media for an additional 66 h followed by incubation with media containing $^3$H-thymidine to assess cell viability. Radioactivity was counted using PerkinElmer's scintillation counter. The same procedure was repeated after exposing the cells to the free tubulysin B hydrazide. Both the cancer cell lines MDA-MB231 and SKOV3 were found to be sensitive to free tubulysin B hydrazide demonstrating $IC_{50}$ value of 67 pM and 5 pM respectively as shown in FIG. 21. In the receptor positive MDA-MB231 cells, targeted conjugate (JL-L3-TubBH) exhibited an IC50 value of 26 nM, whereas in the presence of an excess of competition ligand the potency intensely dropped to 382 nM. The receptor mediated cell killing ability of the targeted conjugate was further confirmed when the $IC_{50}$ values obtained from receptor negative cell line was found to be similar to the MDA-MB231 competition (608 nM).

Figure 22A:
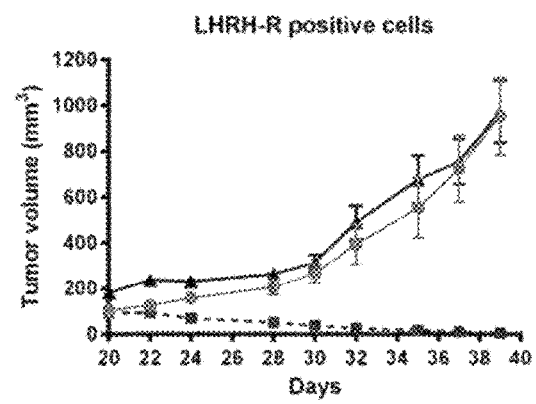
FIG. 22A shows therapeutic efficacy of JL-L3-TubBH against LHRH-R positive cells as determined by tumor volume over time.
Figure 22C:
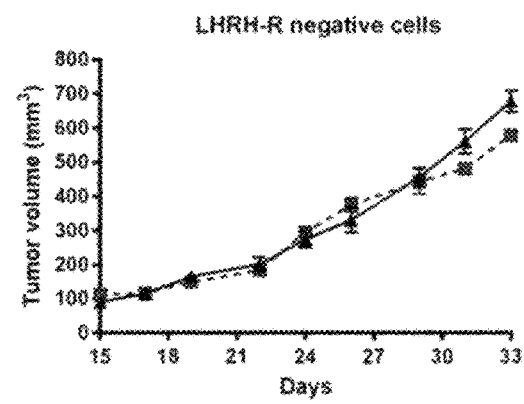
FIG. 22C shows toxicity of JL-L3-TubBH against LHRH-R positive cells as determined by weight change over time.
Figure 22B:
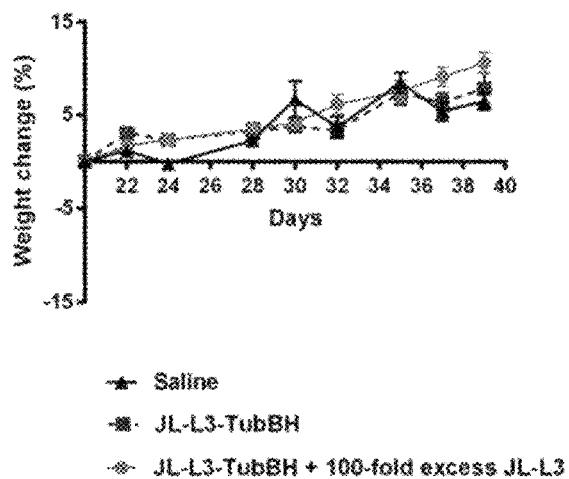
FIG. 22B shows therapeutic efficacy of JL-L3-TubBH against LHRH-R negative cells as determined by tumor volume over time.
Figure 22D:
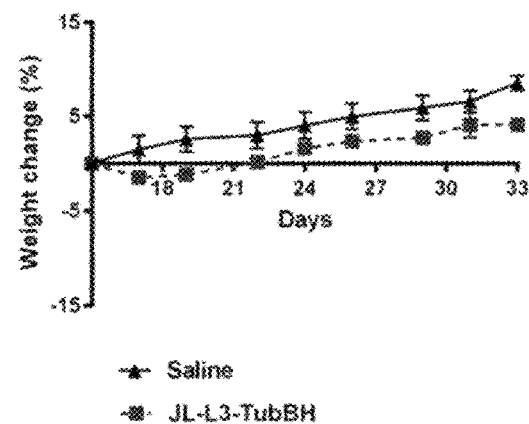
FIG. 22D shows toxicity of JL-L3-TubBH against LHRH-R positive cells as determined by tumor volume over time.

In vivo efficacy of tubulysin B hydrazide conjugate: To investigate the efficacy of JL tubulysin conjugate nu/nu athymic nude bearing LHRH-R positive tumors (MDA-MB-231, breast cancer) were randomly divided into three groups: saline control, targeted, and competition and were then treated with test agents 3 days per week for 3 weeks. LHRH-R positive (MDA-MB-231) and negative (SKOV3) cancer cells were s.c implanted in to nu/nu athymic mice and treatment was initiated once the tumor volume reached ~100 mm³. Mice were randomized into several groups with 5 mice in each group. Mice in control group received saline, whereas mice in the competition and treatment group received 2 μmol/kg of JL-L3-TubBH either in the presence or absence of 100-fold excess of JL-L3 respectively for 3 times per week for 3 weeks. All the test agents were administered intravenously through tail vein. The mice in control and competition group were euthanized after the last doing whereas the mice in treatment group were continuously monitored for recurrence of tumor and weight loss. MD-MB-231 tumor bearing mice that received targeted tubulysin B hydrazide conjugate (JL-L3-TubBH) showed complete elimination of the tumor whereas the mice that received saline did not show any anti-tumor effect. Likewise, the mice in the competition group did not show any decline in tumor growth compared to the control group. (FIG. 22A, The dotted vertical line indicates the day of final dosing (day 36)) Without intending to be bound by theory, this further confirmed that the efficacy of targeted tubulysin B hydrazide conjugate is receptor mediated. Moreover, to comprehensively test the anti-tumor efficacy of targeted conjugate (JL-L3-TubBH), mice bearing LHRH-R negative tumors (SKOV3, ovarian cancer) were divided into similar groups as MDA-MB-231 tumor bearing mice and a similar treatment regimen was followed. There was no reduction in tumor volume was observed in targeted and control group of mice bearing receptor negative tumors. (FIG. 22C) Without intending to be bound by theory, these data further reinforced that the cytotoxicity induced by JL-L3-TubBH is receptor mediated. None of the mice either bearing MDA-MB-231 or SKVO3 experiences significant weight loss. (FIGS. 22B & 22D)

Figure 23A:
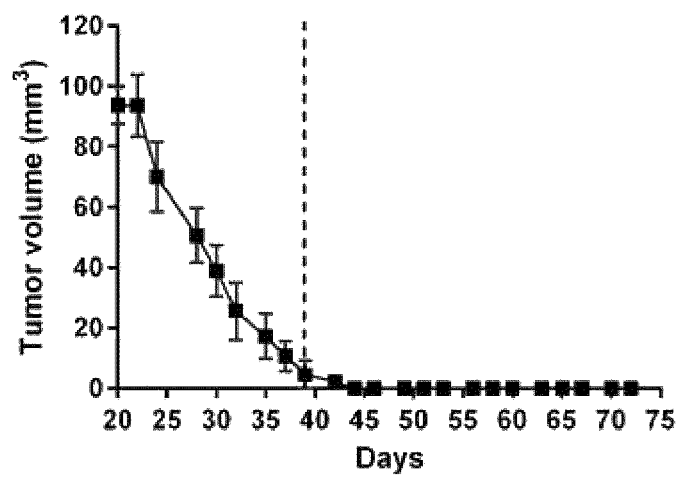
FIG. 23A shows therapeutic efficacy of JL-L3-TubBH against subcutaneous LHRH-R positive MDA-MB231 tumor growth as determined by tumor volume over time.
Figure 23B:
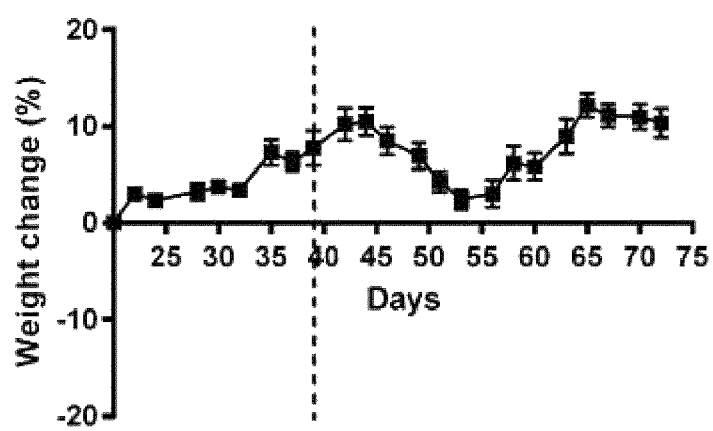
FIG. 23B shows toxicity of JL-L3-TubBH against subcutaneous LHRH-R positive MDA-MB231 tumor growth as determined by weight change over time.

After completion of the treatment the mice in MDA-MB-231 targeted group were monitored and kept on regular chow diet for next five weeks. During this time period the tumor volume and weight was monitored three time a week. (FIG. 23) Mice were treated with the LHRH-R targeted tubulysin B hydrazide conjugate (JR-L3-TubBH) for thrice a week for 3 weeks (n=5). After completion of the study tumor volume and weight of mice was continuously monitored till 75 days post tumor implantation. The dotted vertical line specifies the last day of dosing. None of the mice showed any indication of tumor growth and weight loss. This data indicates that LHRH-R targeted tubulysin B hydrazide conjugate (JL-L3-TubBH) may treat cancers expressing LHRH-R.

In summary, the current study demonstrates the efficacy of the cytotoxic drug conjugated to the non-peptidic small molecule ligand for LHRH-R. The targeted conjugate was able to eliminate the receptor positive tumor and no recurrence of the tumor was observed for at least five weeks after the last dose of the drug. No tumor efficacy was observed in the mice in competition or control group. Receptor negative tumor did not show any reduction in the tumor volume when treated with the LHRH-R targeted tubulysin conjugate. Without intending to be bound by theory, the efficacy of the targeted tubulyisn B conjugate is believed to be receptor mediated. During the course of therapy, no observable weight loss was observed which suggests that side-effects associated with the free drug can be drastically reduced by conjugating it to an appropriate targeting ligand. Thus, the result of this study provides data supporting use of LHRH-R targeted cytotoxic conjugates for the treatment of cancers expressing LHRH-R.

The entire contents of each and every patent publication, non-patent publication, and reference text cited herein are hereby incorporated by reference, except that in the event of any inconsistent disclosure or definition from the present specification, the disclosure or definition herein shall be deemed to prevail.

It is to be understood that use of the indefinite articles "a" and "an" in reference to an element does not exclude the presence, in some embodiments, of a plurality of such elements.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

What is claimed is:

1. A conjugate of the formula B-L-A, wherein B is an LHRH-R binding antagonist of the formula

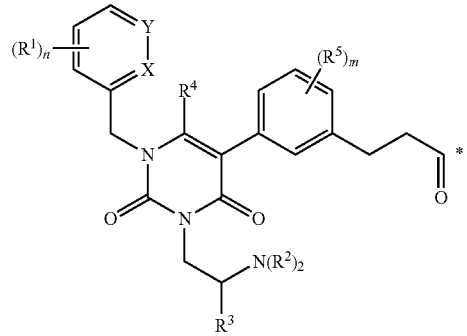

wherein
  each $R^1$ is independently halogen, $C_1$-$C_6$ alkyl or —$OC_1$-$C_6$ alkyl;
  each $R^2$ is independently H, $C_1$-$C_6$ alkyl or $C_3$-$C_6$ cycloalkyl;
  $R^3$ is $C_1$-$C_6$ alkyl, $C_3$-$C_6$ cycloalkyl, $C_6$-$C_{10}$ aryl or $C_1$-$C_6$ alkyl-($C_6$-$C_{10}$ aryl);
  $R^4$ is $C_1$-$C_6$ alkyl;
  each $R^5$ is independently selected from the group consisting of halogen, $C_1$-$C_6$ alkyl, —$OC_1$-$C_6$ alkyl, —$SC_1$-$C_6$ alkyl and —$OC_6$-$C_{10}$ aryl;
  X and Y are each independently N, CH or $CR^1$; provided that when X is N, Y is CH or $CR^1$, and when Y is N, X is CH or $CR^1$;
  m is an integer from 0 to 4;
  n is an integer from 0 to 3; and
  * represents a covalent bond to L;
  L is a linker; and
  A is an imaging agent;
or a pharmaceutically acceptable salt thereof.

2. The conjugate of claim 1, or a pharmaceutically acceptable salt thereof, wherein the imaging agent is selected from the group consisting of a rhodamine dye, a fluorescein dye, a PET imaging agent, or a radiolabeled agent.

3. The conjugate of claim 1, or a pharmaceutically acceptable salt thereof, wherein the imaging agent is selected from the group consisting of 50456, 5-carboxytetramethylrhodamine (5-TAMRA), rhodamine B, rhodamine 6G, TRITC, Texas Red, rhodamine 123, sulforhodamine 101, fluorescein, 5-amino-fluorescein, 6-amino-fluorescein, fluorescein isocyanate (FITC), NHS-fluorescein, Oregon Green, Tokyo Green, Singapore Green, and Philadelphia Green.

4. The conjugate of claim 1, or a pharmaceutically acceptable salt thereof, wherein the imaging agent is a radioactive isotope coordinated to a chelating group.

5. The conjugate of claim 4, or a pharmaceutically acceptable salt thereof, wherein the chelating group is of the formula

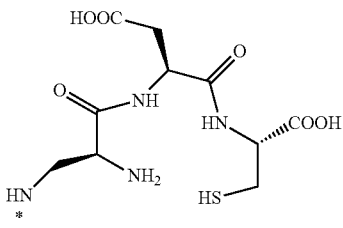

wherein * represents a covalent bond to the rest of the conjugate.

6. The conjugate of claim 4, or a pharmaceutically acceptable salt thereof, wherein the chelating group comprises a radioactive metal isotope selected from the group consisting of an isotope of technetium, rhenium, gallium, gadolinium, indium and copper coordinated thereto.

7. The conjugate of claim 4, or a pharmaceutically acceptable salt thereof, wherein the chelating group comprises a radioactive metal isotope selected from the group consisting of $^{111}$In, $^{99m}$Tc, $^{64}$Cu, $^{67}$Cu, $^{67}$Ga and $^{68}$Ga coordinated thereto.

8. The conjugate of claim 1, or a pharmaceutically acceptable salt thereof, wherein the imaging agent comprises a radioactive isotope.

9. The conjugate of claim 8, or a pharmaceutically acceptable salt thereof, wherein the radioactive isotope is an isotope of hydrogen, an isotope of carbon, an isotope of chlorine, an isotope of fluorine, an isotope of iodine, an isotope of nitrogen, an isotope of oxygen, an isotope of phosphorous, or an isotope of sulfur.

10. The conjugate of claim 8, or a pharmaceutically acceptable salt thereof, wherein the radioactive isotope is selected from the group consisting of $^3$H, $^{11}$C, $^{14}$C, $^{36}$Cl, $^{18}$F, $^{123}$I, $^{125}$I, $^{13}$N, $^{15}$O, $^{32}$P, and $^{35}$S.

11. The conjugate of claim 10, or a pharmaceutically acceptable salt thereof, wherein the radioactive isotope is $^{18}$F or $^{125}$I.

12. The conjugate of claim 1, or a pharmaceutically acceptable salt thereof, wherein the imaging agent comprises a positron emitting isotope.

13. The conjugate of claim 12, or a pharmaceutically acceptable salt thereof, wherein the positron emitting isotope is selected from the group consisting of $^{11}$C, $^{18}$F, $^{13}$N, $^{15}$O, and $^{68}$Ga.

14. The conjugate of claim 1, selected from the group consisting of

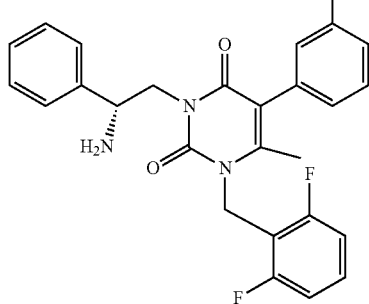

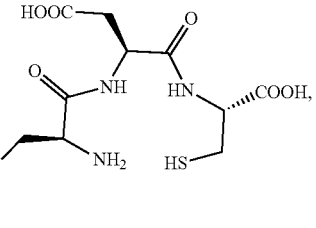

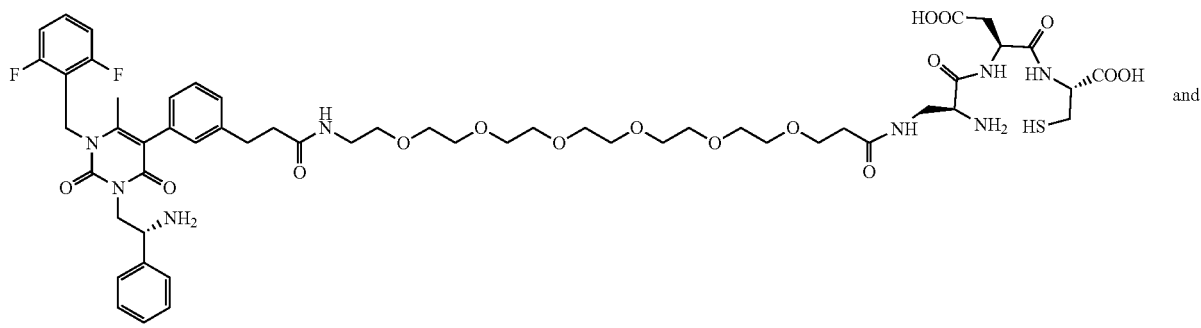

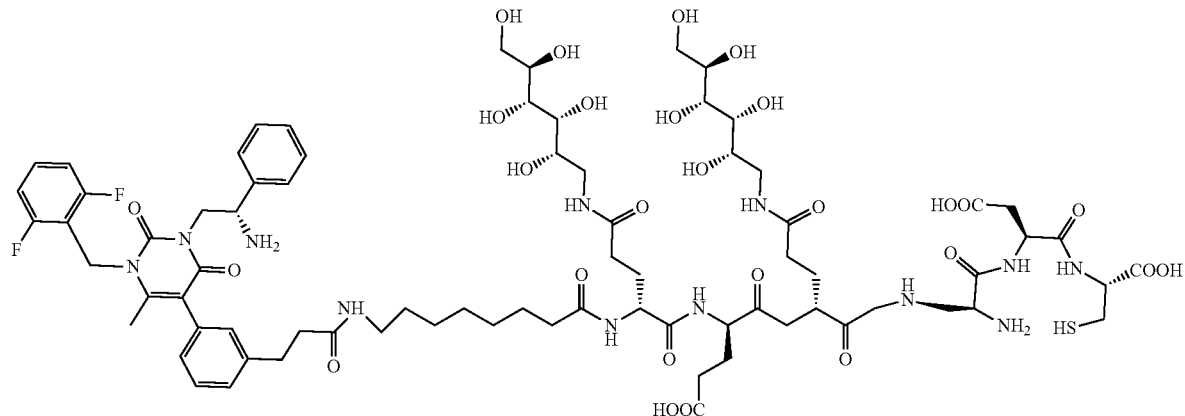

or a pharmaceutically acceptable salt thereof.

15. The conjugate of claim 14, or a pharmaceutically acceptable salt thereof, wherein the conjugate comprises a radioactive metal isotope selected from the group consisting of $^{111}$In, $^{99m}$Tc, $^{64}$Cu, $^{67}$Cu, $^{67}$Ga and $^{68}$Ga coordinated thereto.

16. The conjugate of claim 15, or a pharmaceutically acceptable salt thereof, wherein the radioactive metal isotope is $^{99m}$Tc.

17. The conjugate of claim 1, selected from the group consisting of

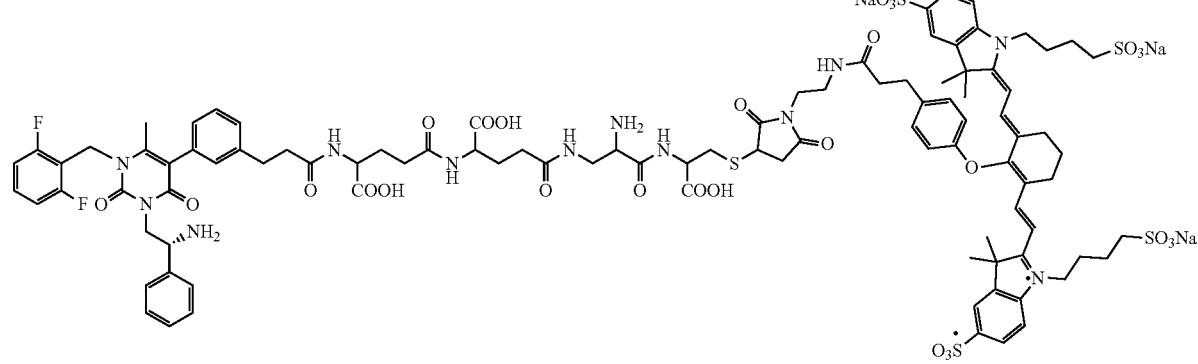

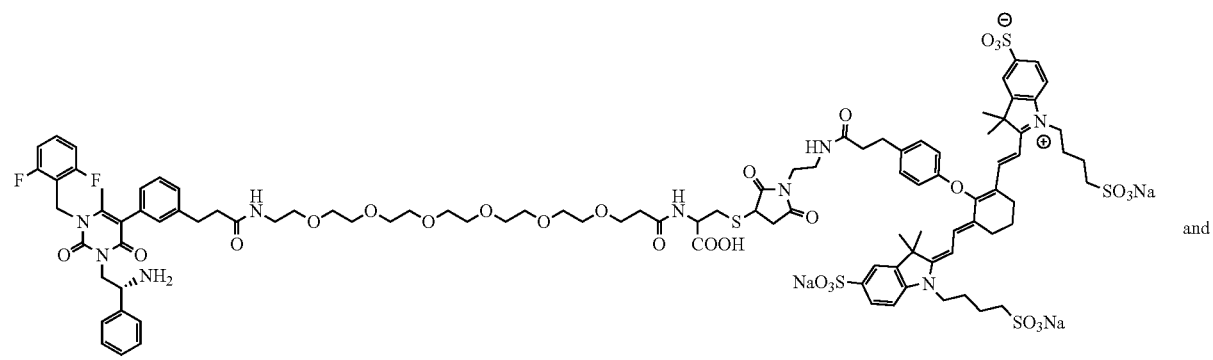

and

-continued

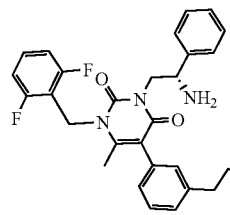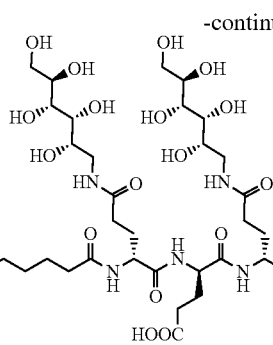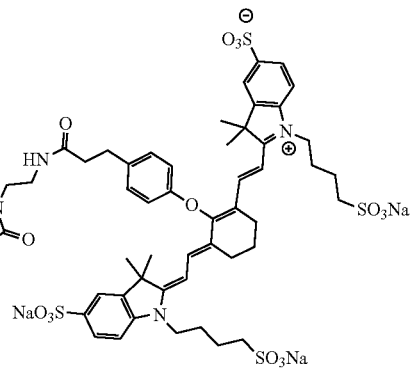

or a pharmaceutically acceptable salt thereof.

18. A pharmaceutical composition comprising a conjugate of claim 1, or a pharmaceutically acceptable salt thereof, and optionally at least one pharmaceutically acceptable excipient.

19. The conjugate of claim 1, or a pharmaceutically acceptable salt thereof, wherein the imaging agent is a radioactive isotope of a metal coordinated to a chelating group.

* * * * *